US 8,344,128 B2
Jan. 1, 2013

(54) SHORT INTERFERING RIBONUCLEIC ACID (SIRNA) FOR ORAL ADMINISTRATION

(75) Inventors: Francois Jean-Charles Natt, Hesingue (FR); Eric Billy, Chatenois (FR); Juerg Hunziker, Aarau (CH); Christian Rene Schnell, Hegenhein (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/218,941

(22) Filed: Aug. 26, 2011

(65) Prior Publication Data

US 2012/0029053 A1    Feb. 2, 2012

Related U.S. Application Data

(62) Division of application No. 12/299,396, filed as application No. PCT/EP2007/003867 on May 2, 2007, now Pat. No. 8,084,600.

(30) Foreign Application Priority Data

May 4, 2006  (GB) .................................. 0608838.9

(51) Int. Cl.
*C07H 21/04* (2006.01)
*C12N 15/11* (2006.01)

(52) U.S. Cl. ..................................... 536/24.5; 514/44 A

(58) Field of Classification Search ................ 514/44 R; 536/24.5

See application file for complete search history.

(56) References Cited

U.S. PATENT DOCUMENTS

| | | | |
|---|---|---|---|
| 5,670,633 A | 9/1997 | Cook et al. | |
| 5,898,031 A | 4/1999 | Crooke | |
| 5,976,567 A | 11/1999 | Wheeler et al. | |
| 5,998,203 A | 12/1999 | Matulic-Adamic et al. | |
| 6,005,087 A | 12/1999 | Cook et al. | |
| 6,033,909 A | 3/2000 | Uhlmann et al. | |
| 6,107,094 A | 8/2000 | Crooke | |
| 6,211,349 B1 | 4/2001 | Dale et al. | |
| 6,476,205 B1 | 11/2002 | Buhr et al. | |
| 6,506,559 B1 | 1/2003 | Driver et al. | |
| 6,531,584 B1 | 3/2003 | Cook et al. | |
| 6,815,432 B2 | 11/2004 | Wheeler et al. | |
| 6,858,225 B2 | 2/2005 | Semple et al. | |
| 7,056,704 B2 | 6/2006 | Tuschl et al. | |
| 7,078,196 B2 | 7/2006 | Tuschl et al. | |
| 7,138,517 B2 | 11/2006 | Cook et al. | |
| 7,432,249 B2 | 10/2008 | Crooke | |
| 7,432,250 B2 | 10/2008 | Crooke | |
| 7,629,321 B2 | 12/2009 | Crooke | |
| 8,097,716 B2 | 1/2012 | Weiler et al. | |
| 2003/0143732 A1 | 7/2003 | Fosnaugh et al. | |
| 2003/0148507 A1 | 8/2003 | Fosnaugh et al. | |
| 2003/0175950 A1 | 9/2003 | McSwiggen | |
| 2003/0190635 A1 | 10/2003 | McSwiggen | |
| 2004/0019001 A1 | 1/2004 | McSwiggen | |
| 2004/0152117 A1 | 8/2004 | Giordano et al. | |
| 2004/0219671 A1 | 11/2004 | McSwiggen et al. | |
| 2004/0259247 A1 | 12/2004 | Tuschl et al. | |
| 2005/0107325 A1 | 5/2005 | Manoharan et al. | |
| 2005/0233329 A1 | 10/2005 | McSwiggen et al. | |
| 2005/0261212 A1 | 11/2005 | McSwiggen | |
| 2006/0063731 A1 | 3/2006 | Lewis et al. | |
| 2007/0004667 A1 | 1/2007 | McSwiggen et al. | |
| 2007/0032441 A1 | 2/2007 | McSwiggen et al. | |
| 2009/0215880 A1 | 8/2009 | Li et al. | |
| 2009/0247606 A1 | 10/2009 | McSwiggen et al. | |
| 2009/0281164 A1 | 11/2009 | McSwiggen et al. | |

FOREIGN PATENT DOCUMENTS

| | | |
|---|---|---|
| AU | 2002/326410 B2 | 2/2003 |
| AU | 2003/216324 B2 | 9/2003 |
| AU | 2004/266311 B2 | 3/2005 |
| DE | 100 80 167 B4 | 3/2008 |
| DE | 100 66 235 B4 | 4/2008 |
| EP | 0 552 766 B1 | 7/1993 |
| EP | 0 928 290 B1 | 7/1999 |
| EP | 1 144 623 B1 | 10/2001 |
| EP | 1 214 945 B1 | 6/2002 |
| EP | 1 229 134 A2 | 8/2002 |
| EP | 1 230 375 B1 | 8/2002 |
| EP | 1 309 726 B1 | 5/2003 |
| EP | 1 352 061 B1 | 10/2003 |
| EP | 1 389 637 A1 | 2/2004 |
| EP | 1 407 044 B1 | 4/2004 |
| EP | 1 550 719 B1 | 7/2005 |
| EP | 1 627 061 B1 | 2/2006 |
| JP | 4095895 B2 | 6/2008 |
| WO | WO 00/44914 A1 | 8/2000 |
| WO | WO 00/63364 A2 | 10/2000 |
| WO | WO 02/096927 A2 | 12/2002 |
| WO | WO 03/010180 A1 | 2/2003 |
| WO | WO 03/066649 A1 | 8/2003 |
| WO | WO 03/070895 A2 | 8/2003 |
| WO | WO 03/070918 A2 | 8/2003 |
| WO | WO 2004/015107 A2 | 2/2004 |
| WO | WO 2004/090105 A2 | 10/2004 |

(Continued)

OTHER PUBLICATIONS

Jeong, et al. Bioconjugate Chem. (2009) 20:5-14.*
Soutschek, et al. Nature (2004) 432:173-178.*
Dande et al.; "Improving RNA Interference in Mammalian Cells by 4'-Thio-Modified Small Interfering RNA (siRNA): Effect on siRNA Activity and Nuclease Stability When Used in Combination with 2'-O-Alkyl Modifications"; J. Med. Chem.; 49(5):1624-1634 (2006).
Opalinska et al., Nature, 1:503-514 (2002).
Amarzguioui et al., Nucleic Acids Research, 31(2):589-595 (2003).
EP Office Action for corresponding EP Appln. 09 169 772.2 dated Aug. 19, 2011.
JP Office Action for corresponding JP Appln. 2009-508205 dated Jul. 19, 2012.
Schwarz et al; "Evidence that siRNAs Function as Guides, Not Primers, in the Drosophila and Human RNAi Pathways"; Molecular Cell; 10:537-548 (2002).
Seela et al; "Oligodeoxyribonucleotides containing 1,3-propanediol as nucleoside substitute"; Nucleic Acids Research 15(7):3113-3129 (1987).

(Continued)

*Primary Examiner* — J. E. Angell
(74) *Attorney, Agent, or Firm* — Frank Wu

(57) ABSTRACT

Short interfering ribonucleic acid (siRNA) for oral administration, said siRNA comprising two separate RNA strands that are complementary to each other over at least 15 nucleotides, wherein each strand is 49 nucleotides or less, and wherein at least one of which strands contains at least one chemical modification.

20 Claims, 18 Drawing Sheets

FOREIGN PATENT DOCUMENTS

| | | | |
|---|---|---|---|
| WO | WO 2004/092383 A2 | 10/2004 | |
| WO | WO 2005/019453 A2 | 3/2005 | |
| WO | WO 2005/021749 A1 | 3/2005 | |
| WO | WO 2005/115481 A2 | 12/2005 | |
| WO | WO 2007/128477 A2 | 11/2007 | |

OTHER PUBLICATIONS

Shah et al.; "An ESI-MS method for characterization of native and modified oligonucleotides used for RNA interference and other biological applications"; Nature Protocols; 3(3):351-356 (2008).

Shen et al.; "Suppression of ocular neovascularization with siRNA targeting VEGF receptor 1"; Gene Therapy; 13(3):225-234 (2005).

Sioud; "Ribozymes and siRNAs: From Structure to Preclinical Applications"; HEP [Published by Springer-Verlag Berlin Heidelberg]; 173:223-242 (2006).

Song et al; "The crystal structure of the Argonaute2 PAZ domain reveals an RNA binding motif in RNAi effector complexes"; Nature Structural Biology 10(12):1026-1032 (2003).

Takeshita et al; "Oligodeoxynucleotides Containing Synthetic Abasic Sites"; The Journal of Biological Chemistry 262 (21):10171-10179 (1987).

Takahashi et al.; "Synthesis and characterization of 2'-modified-4'-thioRNA: a comprehensive comparison of nuclease stability"; Nucleic Acids Research; 37(4):1353-1362 (2009).

Thomas et al; "Capping of bcr-abl Antisense Oligonucleotides Enhances Antiproliferative Activity Against Chronic Myeloid Leukemia Cell Lines"; Leukemia Research 18(6):401-408 (1994).

Tavernarakis et al.; "Heritable and inducible genetic interference by double-stranded RNA encoded by transgenes"; Nature Genetics; 24:180-183 (2000).

Terrazas et al.; "RNA major groove modifications improve siRNA stability and biological activity"; Nucleic Acids Research; 37(2):346-353 (2009).

Ueno et al.; "Synthesis and properties of siRNAs containing 5'-amino-2',5'-dideoxy-2'alpha-fluororibonucleosides"; Tetrahedron; 64:11328-11334 (2008).

Ullu et al.; "RNA interference: advances and questions"; Phil. Trans. R. Soc. Lond. B; 357:65-70 (2002).

Wang et al.; "Subsection E Methods of RGS Protein Inhibition: [15] Ribozyme- and siRNA-Mediated Suppression of RGS-Containing RhoGEF Proteins"; Methods in Enzymology; 389:244-265 (2004).

Watts et al.; "Chemically modified siRNA: tools and applications"; Drug Discovery Today; 13(19/20):842-855 (2008).

Yan et al; "Structure and conserved RNA binding of the PAZ domain"; Letters to Nature 426:469-475 (2003).

Zendegui et al; "In vivo stability and kinetics of absorption and disposition of 3' phosphopropyl amine oligonucleotides"; Nucleic Acids Research 20(2):307-314 (1992).

Zhang et al.; "RNA interference in mammalian cells by siRNAs modified with morpholino nucleoside analogues"; Bioorganic & Medicinal Chemistry; 17:2441-2446 (2009).

Zhao et al; "Comparison of Cellular Binding and Uptake of Antisense Phosphodiester, Phosphorothioate, and Mixed Phosphorothioate and Methylphosphonate Oligonucleotides"; Antisense Research and Development 3:53-66 (1993).

Al-Anouti et al.; "Comparative Analysis of Antisense RNA, Double-Stranded RNA, and Delta Ribozyme-Mediated Gene Regulation in Toxoplasma gondii"; Antisense and Nucleic Acid Drug Development; 12:275-281 (2002).

Aubert et al; "Optimized Synthesis of Phosphorothioate Oligodeoxyribonucleotides Substituted With a 5'-Protected Thiol Function and a 3'-Amino Group"; Nucleic Acids Research 28(3):818-825 (2000).

Bass; "The short answer"; Nature—News and Views, RNA Interference; 411:428-429 (2001).

Beaucage et al; "The Functionalization of Oligonucleotides Via Phosphoramidite Derivatives"; Tetrahedron 49 (10):1925-1963 (1993).

Beigelman et al.; "Chemical Modification of Hammerhead Ribozymes"; The Journal of Biological Chemistry; 270(43):25702-25708 (1995).

Biessen et al; "Targeted delivery of oligodeoxynucleotides to parenchymal liver cells in vivo"; Biochem. J. 340:783-792 (1999).

Biessen et al; "Targeted Delivery of Antisense Oligonucleotides to Parenchymal Liver Cells in Vivo"; Methods in Enzymology 314:324-342 (1999).

Braasch et al.; "Novel Antisense and Peptide Nucleic Acid Strategies for Controlling Gene"; Biochemistry—Current Topics; 41(14):4503-4510 (2002).

Braasch et al.; "RNA Interference in Mammalian Cells by Chemically-Modified RNA"; Biochemistry; 42:7967-7975 (2003).

Bramsen et al.; "A large-scale chemical modification screen identifies design rules to generate siRNAs with high activity, high stability and low toxicity"; Nucleic Acids Research; 37(9):2867-2881 (2009).

Bramsen et al.; "A large-scale chemical modification screen identifies design rules to generate siRNAs with high activity, high stability and low toxicity [Supplemental Figures]"; Nucleic Acids Research; 37(9):2867-2881 (2009).

Chiu et al; "RNAi in Human Cells: Basic Structural and Functional Features of Small Interfering RNA"; Molecular Cell 10:549-561 (2002).

Chiu et al.; "siRNA function in RNAi: A chemical modification analysis"; RNA; 9:1034-1048 (2003).

Chiu et al; "Visualizing a Correlation between siRNA Localization, Cellular Uptake, and RNAi in Living Cells"; Chemistry & Biology; 11:1165-1175 (2004).

Corey; "Chemical modification: the key to clinical application of RNA interference?"; The Journal of Clinical Investigation—Review Series; 117(12):3615-3622 (2007).

Crooke et al.; "Metabolism of Antisense Oligonucleotides in Rat Liver Homogenates"; The Journal of Pharmacology and Experimental Therapeutics; 292(1):140-149 (2000).

Czaudema et al; "Structural variations and stabilising modifications of synthetic siRNAs in mammalian cells"; Nucleic Acids Research 31(11):2705-2716 (2003).

Deleavey et al.; "Chemical Modification of siRNA"; Current Protocols in Nucleic Acid Chemistry [Published by John Wiley & Sons, Inc.]; 39:16.3.1-16.3.22 (2009).

Dorsett et al.; "siRNAs: Applications in Functional Genomics and Potential As Therapeutics"; Nature Reviews—Drug Discovery; 3:318-329 (2004).

Elbashir et al.; "Duplexes of 21-nucleotide RNAs mediate RNA interference in cultured mammalian cells"; Nature; 411:494-498 (2001).

Elbashir et al; "Functional anatomy of siRNAs for mediating efficient RNAi in Drosophila melanogaster embryo lysate"; The EMBO Journal 20(23):6877-6888 (2001).

Elbashir et al; "RNA interference is mediated by 21- and 22-nucleotide RNAs"; Genes & Development 15:188-200 (2001).

Fennewald et al; "Inhibition of High Affinity Basic Fibroblast Growth Factor Binding by Oligonucleotides"; The Journal of Biological Chemistry 270(37):21718-21721 (1995).

Guy-Caffey et al; "Novel Polyaminolipids Enhance the Cellular Uptake of Oligonucleotides"; The Journal of Biological Chemistry 270(52):31391-31396 (1995).

Hadwiger et al.; "Chemical modifications to achieve increased stability and sensitive detection of siRNA"; RNA Interference Technology—From Basic Science to Drug Development, Edited by Krishnarao Appasani, Published by Cambridge University Press; 14:194-206 (2005).

Hamada et al; "Effects of RNA Interference in Gene Expression (RNAI) In Cultured Mammalain Cells of Mismatches and the Introduction of Chemical Modifications at the 3'-Ends of SIRNAS"; Antisense & Nucleic Acid Drug Development 12(5):301-309 (2002).

Hamilton et al.; "Two classes of short interfering RNA in RNA silencing"; The EMBO Journal 21(17):4671-4679 (2002).

Harborth et al.; "Sequence, Chemical, and Structural Variation of Small Interfering RNAs and Short Hairpin RNAs and the Effect on Mammalian Gene Silencing"; Antisense and Nucleic Acid Drug Development; 13:83-105 (2003).

Hasan et al.; "VEGF antagonists"; Expert Opin. Biol. Ther.—Review; 1(4):703-718 (2001).

Igloi; "Nonradioactive Labeling of RNA"; Analytical Biochemistry 233:124-129 (1996).

Kawasaki et al.; "World of small RNAs: from ribozymes to siRNA and miRNA"; Differentiation—Review; 72:58-64 (2004).

Kennerdell et al.; "Heritable gene silencing in Drosophila using double-stranded RNA"; Nature Biotechnology; 17:896-898 (2000).

Khan et al.; "Sustained Polymeric Delivery of Gene Silencing Antisense ODNs, siRNA, DNAzymes and Ribozymes: In Vitro and In Vivo Studies"; Journal of Drug Targeting; 12(6):393-404 (2004).

Kim et al.; "Inhibition of Ocular Angiogenesis by SIRNA Targeting Vascular Endothelial Growth Factor Pathway Genes Therapeutic Strategy for Herpetic Stromal Keratitis"; American Journal of Pathology; 165(6):2177-2185 (2004).

Kim et al; "Local and systemic delivery of VEGF siRNA using polyelectrolyte complex micelles for effective treatment of cancer"; Journal of Controlled Release; 129:107-116 (2008).

Klysik et al; "A 15-Base Acridine-Conjugated Oligodeoxynucleotide Forms Triplex DNA with Its IL-2Rr Promoter Target with Greatly Improved Avidity"; Bioconjugate Chem. 8:318-326 (1997).

Kraynack et al.; "Small interfering RNAs containing full 2'-O-methylribonucleotide-modified sense strands display Argonaute2/eIF2C2-dependent activity"; RNA; 12:163-176 (2006).

Lingel et al; "Structure and nucleic acid binding of the Drosophila Argonaute 2 PAZ domain"; Letters to Nature 426:465-469 (2003).

Lipardi et al.; "RNAi as Random Degradative PCR: siRNA Primers Convert mRNA into dsRNAs that Are Degraded to Generate New siRNAs"; Cell; 107:297-307 (2001).

McShan et al; "Inhibition of Transcription of HIV-1 in Infected Human Cells by Oligodeoxynucleotides Designed to Form DNA Triple Helices"; The Journal of Biological Chemistry 267(8):5712-5721 (1992).

Miyagishi et al.; "Comparison of the Suppressive Effects of Antisense Oligonucleotides and siRNAs Directed Against the Same Targets in Mammalian Cells"; Antisense and Nucleic Acid Drug Development; 13:1-7 (2003).

Nelson et al; "Bifunctional oligonucleotide probes synthesized using a novel CPG support are able to detect single base pair mutations"; Nucleic Acids Research 17(18):7187-7194 (1989).

Nelson et al; "A new and versatile reagent for incorporating multiple primary aliphatic amines into synthetic oligonucleotides"; Nucleic Acids Research 17(18):7179-7186 (1989).

Olejnik et al; "Photocleavable aminotag phosphoramidites for 5'-termini DNA/RNA labeling"; Nucleic Acids Research 26(15):3572-3576 (1998).

Parrish et al.; "Functional Anatomy of a dsRNA Trigger: Differential Requirement for the Two Trigger Strands in RNA Interference"; Molecular Cell; 6:1077-1087 (2000).

Polak et al., "Tuning of Conformational Preorganization in Model 2',5'- and 3',5'-linked Oligonucleotides by 3'- and 2'-O-methoxyethyl Modification", Nucleic Acids Research, 31(8):2066-2076 (2003).

Prakash et al.; "Positional Effect of Chemical Modifications on Short Interference RNA Activity in Mammalian Cells"; J. Med. Chem.; 48:4247-4253 (2005).

Rando et al; "Suppression of Human Immunodeficiency Virus Type 1 Activity in Vitro by Oligonucleotides Which Form Intramolecular Tetrads"; The Journal of Biological Chemistry 270(4):1754-1760 (1995).

* cited by examiner t=0' t=180'

LC-MS analysis

| Compound | Sequence | Mth | found |
|---|---|---|---|
| parent_complement | CUUACGCUGAGUACUUCGAUU | 6607.32 | |
| complement –Tp | CUUACGCUGAGUACUUCGAU | 6302.9 | 6306.4 |
| complement –TpTp | CUUACGCUGAGUACUUCGA | 5998.7 | 5996.8 |
| complement –TpTp –3' Ap | CUUACGCUGAGUACUUCG | 5669.5 | 5670.9 |
| parent_guide | UCGAAGUACUCAGCGUAAUU | 6693.37 | |
| guide –Tp | UCGAAGUACUCAGCGUAAU | 6389.1 | 6387.5 |
| guide –TpTp | CGAAGUACUCAGCGUAAG | 6084.8 | 6084.2 |
| guide –TpTp –3'Gp | UCGAAGUACUCAGCGUAA | 5739.6 | 5740.6 |
| guide –TpTp –5'Tp | CGAAGUACUCAGCGUAAG | 5778.7 | 5775.2 |

FIG.1d

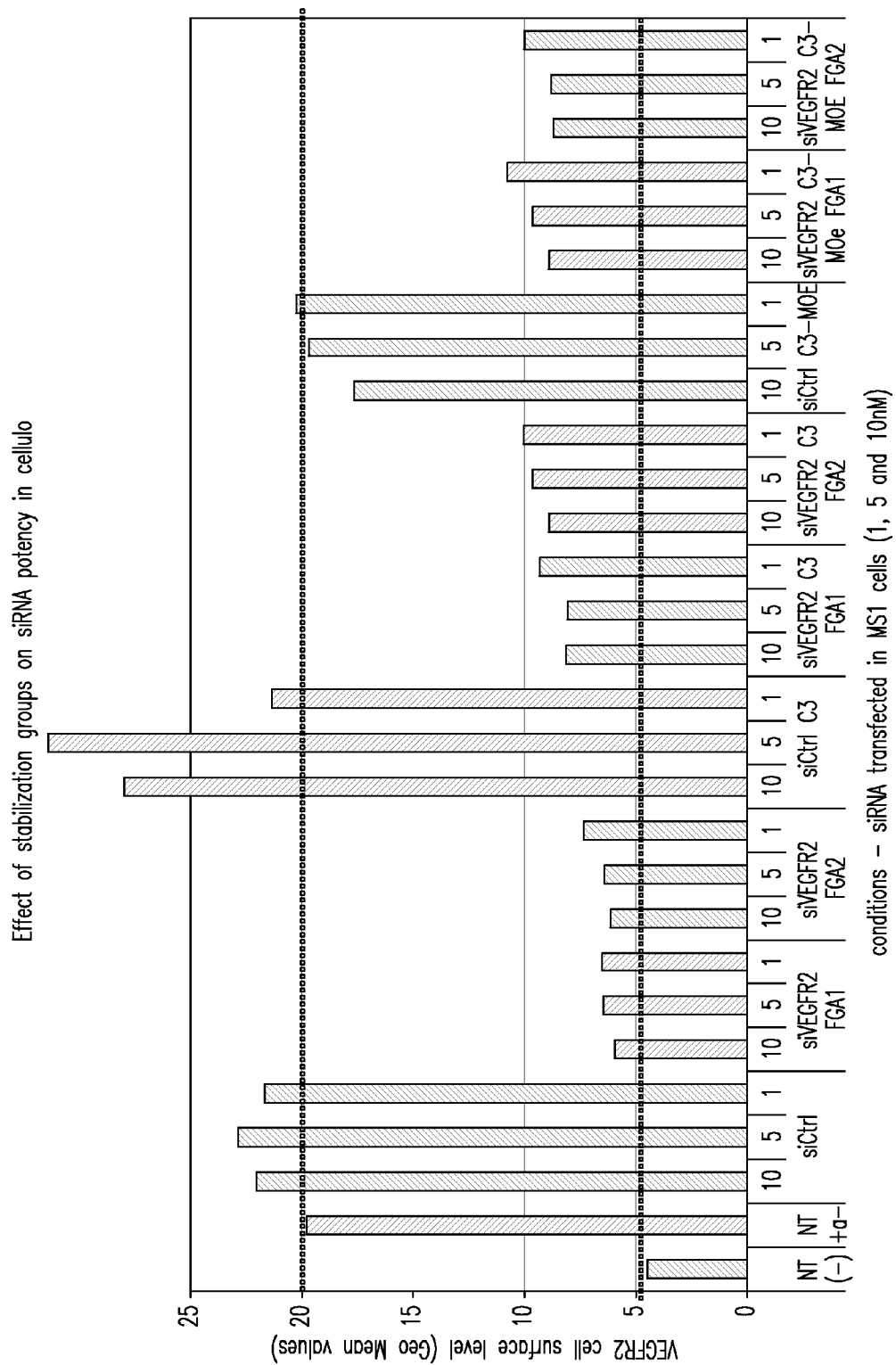

SEQUENCE LISTING

<160> NUMBER OF SEQ ID NOS: 930

<210> SEQ ID NO 1
<211> LENGTH: 21

-continued

<212> TYPE: DNA
<213> ORGANISM: homo sapiens

<400> SEQUENCE: 1
uauaagaacu uguuaacugt g                                             21

<210> SEQ ID NO 2
<211> LENGTH: 21
<212> TYPE: DNA
<213> ORGANISM: homo sapiens

<400> SEQUENCE: 2
uacgguuuca agcaccugct g                                             21

<210> SEQ ID NO 3
<211> LENGTH: 21
<212> TYPE: DNA
<213> ORGANISM: homo sapiens

<400> SEQUENCE: 3
uuuaugcuca gcaagauugt a                                             21

<210> SEQ ID NO 4
<211> LENGTH: 21
<212> TYPE: DNA
<213> ORGANISM: homo sapiens

<400> SEQUENCE: 4
uuaucuuccu gaaagccgga g                                             21

<210> SEQ ID NO 5
<211> LENGTH: 21
<212> TYPE: DNA
<213> ORGANISM: homo sapiens

<400> SEQUENCE: 5
uugagggaua ccauaugcgg t                                             21

<210> SEQ ID NO 6
<211> LENGTH: 21
<212> TYPE: DNA
<213> ORGANISM: homo sapiens

<400> SEQUENCE: 6
uugauaauua acgaguagcc a                                             21

<210> SEQ ID NO 7
<211> LENGTH: 21
<212> TYPE: DNA
<213> ORGANISM: homo sapiens

<400> SEQUENCE: 7
uuaaccauac aacuuccggc g                                             21

<210> SEQ ID NO 8
<211> LENGTH: 21
<212> TYPE: DNA
<213> ORGANISM: homo sapiens

<400> SEQUENCE: 8
uuaggugacg uaacccggca g                                             21

<210> SEQ ID NO 9
<211> LENGTH: 21

```
<212> TYPE: DNA
<213> ORGANISM: homo sapiens

<400> SEQUENCE: 9
uugcucuuga gguaguugga g                                              21

<210> SEQ ID NO 10
<211> LENGTH: 21
<212> TYPE: DNA
<213> ORGANISM: homo sapiens

<400> SEQUENCE: 10
uuugucuuau acaaaugccc a                                              21

<210> SEQ ID NO 11
<211> LENGTH: 21
<212> TYPE: DNA
<213> ORGANISM: homo sapiens

<400> SEQUENCE: 11
uugacaauua gaguggcagt g                                              21

<210> SEQ ID NO 12
<211> LENGTH: 21
<212> TYPE: DNA
<213> ORGANISM: homo sapiens

<400> SEQUENCE: 12
uuauaauuga uagguaguca g                                              21

<210> SEQ ID NO 13
<211> LENGTH: 21
<212> TYPE: DNA
<213> ORGANISM: homo sapiens

<400> SEQUENCE: 13
uugaguaugu aaacccacua t                                              21

<210> SEQ ID NO 14
<211> LENGTH: 21
<212> TYPE: DNA
<213> ORGANISM: homo sapiens

<400> SEQUENCE: 14
uuccauagug augggcucct t                                              21

<210> SEQ ID NO 15
<211> LENGTH: 21
<212> TYPE: DNA
<213> ORGANISM: homo sapiens

<400> SEQUENCE: 15
ucuguuauua acuguccgca g                                              21

<210> SEQ ID NO 16
<211> LENGTH: 21
<212> TYPE: DNA
<213> ORGANISM: homo sapiens

<400> SEQUENCE: 16
uugggaugua gucuuuacca t                                              21

<210> SEQ ID NO 17
<211> LENGTH: 21
```

```
<212> TYPE: DNA
<213> ORGANISM: homo sapiens

<400> SEQUENCE: 17
uguuagagug aucagcucca g                                              21

<210> SEQ ID NO 18
<211> LENGTH: 21
<212> TYPE: DNA
<213> ORGANISM: homo sapiens

<400> SEQUENCE: 18 uuccaucag ggaucaaagt g                                               21

<210> SEQ ID NO 19
<211> LENGTH: 21
<212> TYPE: DNA
<213> ORGANISM: homo sapiens

<400> SEQUENCE: 19
uugaacucuc guguucaagg g                                              21

<210> SEQ ID NO 20
<211> LENGTH: 21
<212> TYPE: DNA
<213> ORGANISM: homo sapiens

<400> SEQUENCE: 20
uagacuuguc cgagguucct t                                              21

<210> SEQ ID NO 21
<211> LENGTH: 21
<212> TYPE: DNA
<213> ORGANISM: homo sapiens

<400> SEQUENCE: 21
uugaggacaa gaguauggcc t                                              21

<210> SEQ ID NO 22
<211> LENGTH: 21
<212> TYPE: DNA
<213> ORGANISM: homo sapiens

<400> SEQUENCE: 22
uuacugguua cucucaaguc a                                              21

<210> SEQ ID NO 23
<211> LENGTH: 21
<212> TYPE: DNA
<213> ORGANISM: homo sapiens

<400> SEQUENCE: 23
uuccagcuca gcguggucgt a                                              21

<210> SEQ ID NO 24
<211> LENGTH: 21
<212> TYPE: DNA
<213> ORGANISM: homo sapiens

<400> SEQUENCE: 24
ugcuucggaa ugauuauggt t                                              21

<210> SEQ ID NO 25
<211> LENGTH: 21
```

```
<212> TYPE: DNA
<213> ORGANISM: homo sapiens

<400> SEQUENCE: 25
uugacuguug cuucacaggt c                                              21

<210> SEQ ID NO 26
<211> LENGTH: 21
<212> TYPE: DNA
<213> ORGANISM: homo sapiens

<400> SEQUENCE: 26
ucauccauuu guacuccugg g                                              21

<210> SEQ ID NO 27
<211> LENGTH: 21
<212> TYPE: DNA
<213> ORGANISM: homo sapiens

<400> SEQUENCE: 27
ugguuucuug ccuuguucca g                                              21

<210> SEQ ID NO 28
<211> LENGTH: 21
<212> TYPE: DNA
<213> ORGANISM: homo sapiens

<400> SEQUENCE: 28
uuaggcucca uguguagugc t                                              21

<210> SEQ ID NO 29
<211> LENGTH: 21
<212> TYPE: DNA
<213> ORGANISM: homo sapiens

<400> SEQUENCE: 29
ucuagaguca gccacaacca a                                              21

<210> SEQ ID NO 30
<211> LENGTH: 21
<212> TYPE: DNA
<213> ORGANISM: homo sapiens

<400> SEQUENCE: 30
uaauuaacga guagccacga g                                              21

<210> SEQ ID NO 31
<211> LENGTH: 21
<212> TYPE: DNA
<213> ORGANISM: homo sapiens

<400> SEQUENCE: 31
uaaccauaca acuuccggcg a                                              21

<210> SEQ ID NO 32
<211> LENGTH: 21
<212> TYPE: DNA
<213> ORGANISM: homo sapiens

<400> SEQUENCE: 32
uucacauuga caauuagagt g                                              21

<210> SEQ ID NO 33
<211> LENGTH: 21
```

-continued

```
<212> TYPE: DNA
<213> ORGANISM: homo sapiens

<400> SEQUENCE: 33
auguaaaccc acuauuucct g                                              21

<210> SEQ ID NO 34
<211> LENGTH: 21
<212> TYPE: DNA
<213> ORGANISM: homo sapiens

<400> SEQUENCE: 34
auccucuuca guuacgucct t                                              21

<210> SEQ ID NO 35
<211> LENGTH: 21
<212> TYPE: DNA
<213> ORGANISM: homo sapiens

<400> SEQUENCE: 35
uuguauaauu cccugcaucc t                                              21

<210> SEQ ID NO 36
<211> LENGTH: 21
<212> TYPE: DNA
<213> ORGANISM: homo sapiens

<400> SEQUENCE: 36
uuuaaccaua caacuuccgg c                                              21

<210> SEQ ID NO 37
<211> LENGTH: 21
<212> TYPE: DNA
<213> ORGANISM: homo sapiens

<400> SEQUENCE: 37
uacaaaugcc cauugacugt t                                              21

<210> SEQ ID NO 38
<211> LENGTH: 21
<212> TYPE: DNA
<213> ORGANISM: homo sapiens

<400> SEQUENCE: 38
auguuaggug acguaacccg g                                              21

<210> SEQ ID NO 39
<211> LENGTH: 21
<212> TYPE: DNA
<213> ORGANISM: homo sapiens

<400> SEQUENCE: 39
uaagucacgu uugcucuuga g                                              21

<210> SEQ ID NO 40
<211> LENGTH: 21
<212> TYPE: DNA
<213> ORGANISM: homo sapiens

<400> SEQUENCE: 40
uuugcucuug agguaguugg a                                              21

<210> SEQ ID NO 41
<211> LENGTH: 21
```

```
<212> TYPE: DNA
<213> ORGANISM: homo sapiens

<400> SEQUENCE: 41
uuuccuguca guauggcaut g                                              21

<210> SEQ ID NO 42
<211> LENGTH: 21
<212> TYPE: DNA
<213> ORGANISM: homo sapiens

<400> SEQUENCE: 42
uacuguagug cauuguucug t                                              21

<210> SEQ ID NO 43
<211> LENGTH: 21
<212> TYPE: DNA
<213> ORGANISM: homo sapiens

<400> SEQUENCE: 43
auaauuaacg aguagccacg a                                              21

<210> SEQ ID NO 44
<211> LENGTH: 21
<212> TYPE: DNA
<213> ORGANISM: homo sapiens

<400> SEQUENCE: 44
uuguagguug agggauacca t                                              21

<210> SEQ ID NO 45
<211> LENGTH: 21
<212> TYPE: DNA
<213> ORGANISM: homo sapiens

<400> SEQUENCE: 45
uugaacagug agguaugcug a                                              21

<210> SEQ ID NO 46
<211> LENGTH: 21
<212> TYPE: DNA
<213> ORGANISM: homo sapiens

<400> SEQUENCE: 46
uuuaccaucc uguuguacat t                                              21

<210> SEQ ID NO 47
<211> LENGTH: 21
<212> TYPE: DNA
<213> ORGANISM: homo sapiens

<400> SEQUENCE: 47
uuucacauug acaauuagag t                                              21

<210> SEQ ID NO 48
<211> LENGTH: 21
<212> TYPE: DNA
<213> ORGANISM: homo sapiens

<400> SEQUENCE: 48
auacuguagu gcauuguuct g                                              21

<210> SEQ ID NO 49
<211> LENGTH: 21
```

```
<212> TYPE: DNA
<213> ORGANISM: homo sapiens

<400> SEQUENCE: 49
uacucucaag ucaaucuuga g                                              21

<210> SEQ ID NO 50
<211> LENGTH: 21
<212> TYPE: DNA
<213> ORGANISM: homo sapiens

<400> SEQUENCE: 50
aaauaaguca cguuugcuct t                                              21

<210> SEQ ID NO 51
<211> LENGTH: 21
<212> TYPE: DNA
<213> ORGANISM: homo sapiens

<400> SEQUENCE: 51
uaauagacug guaacuuuca t                                              21

<210> SEQ ID NO 52
<211> LENGTH: 21
<212> TYPE: DNA
<213> ORGANISM: homo sapiens

<400> SEQUENCE: 52
uagaagguug accacauuga g                                              21

<210> SEQ ID NO 53
<211> LENGTH: 21
<212> TYPE: DNA
<213> ORGANISM: homo sapiens

<400> SEQUENCE: 53
uagcugauca uguagcuggg a                                              21

<210> SEQ ID NO 54
<211> LENGTH: 21
<212> TYPE: DNA
<213> ORGANISM: homo sapiens

<400> SEQUENCE: 54
uugcuguccc aggaaauuct g                                              21

<210> SEQ ID NO 55
<211> LENGTH: 21
<212> TYPE: DNA
<213> ORGANISM: homo sapiens

<400> SEQUENCE: 55
augauuucca aguucgucut t                                              21

<210> SEQ ID NO 56
<211> LENGTH: 21
<212> TYPE: DNA
<213> ORGANISM: homo sapiens

<400> SEQUENCE: 56
uaauguacac gacuccaugt t                                              21

<210> SEQ ID NO 57
<211> LENGTH: 21
```

```
<212> TYPE: DNA
<213> ORGANISM: homo sapiens

<400> SEQUENCE: 57
uucaucugga uccaugacga t                                              21

<210> SEQ ID NO 58
<211> LENGTH: 21
<212> TYPE: DNA
<213> ORGANISM: homo sapiens

<400> SEQUENCE: 58
ugauucucca gguuuccugt g                                              21

<210> SEQ ID NO 59
<211> LENGTH: 21
<212> TYPE: DNA
<213> ORGANISM: homo sapiens

<400> SEQUENCE: 59
uagaccguac augucagcgt t                                              21

<210> SEQ ID NO 60
<211> LENGTH: 21
<212> TYPE: DNA
<213> ORGANISM: homo sapiens

<400> SEQUENCE: 60 uucggugua guauaaucag g                                               21

<210> SEQ ID NO 61
<211> LENGTH: 21
<212> TYPE: DNA
<213> ORGANISM: homo sapiens

<400> SEQUENCE: 61
uuucgugccg ccagguccct g                                              21

<210> SEQ ID NO 62
<211> LENGTH: 21
<212> TYPE: DNA
<213> ORGANISM: homo sapiens

<400> SEQUENCE: 62
uucuucacaa ggguaugggt t                                              21

<210> SEQ ID NO 63
<211> LENGTH: 21
<212> TYPE: DNA
<213> ORGANISM: homo sapiens

<400> SEQUENCE: 63
ucaauuucca aagaguaucc a                                              21

<210> SEQ ID NO 64
<211> LENGTH: 21
<212> TYPE: DNA
<213> ORGANISM: homo sapiens

<400> SEQUENCE: 64
uaguucaauu ccaugagacg g                                              21

<210> SEQ ID NO 65
<211> LENGTH: 21
```

```
<212> TYPE: DNA
<213> ORGANISM: homo sapiens

<400> SEQUENCE: 65
aacauggcaa ucaccgccgt g                                              21

<210> SEQ ID NO 66
<211> LENGTH: 21
<212> TYPE: DNA
<213> ORGANISM: homo sapiens

<400> SEQUENCE: 66
uccuucaaua caaugccuga g                                              21

<210> SEQ ID NO 67
<211> LENGTH: 21
<212> TYPE: DNA
<213> ORGANISM: homo sapiens

<400> SEQUENCE: 67
uacaaguuuc uuaugcugat g                                              21

<210> SEQ ID NO 68
<211> LENGTH: 21
<212> TYPE: DNA
<213> ORGANISM: homo sapiens

<400> SEQUENCE: 68
ugauaucgga agaacaaugt a                                              21

<210> SEQ ID NO 69
<211> LENGTH: 21
<212> TYPE: DNA
<213> ORGANISM: homo sapiens

<400> SEQUENCE: 69
ugugcuauua gagaacaugg t                                              21

<210> SEQ ID NO 70
<211> LENGTH: 21
<212> TYPE: DNA
<213> ORGANISM: homo sapiens

<400> SEQUENCE: 70
uucuacauca cugagggact t                                              21

<210> SEQ ID NO 71
<211> LENGTH: 21
<212> TYPE: DNA
<213> ORGANISM: homo sapiens

<400> SEQUENCE: 71
ucuuuaaacc acaugaucug t                                              21

<210> SEQ ID NO 72
<211> LENGTH: 21
<212> TYPE: DNA
<213> ORGANISM: homo sapiens

<400> SEQUENCE: 72
ucuugcacaa agugacacgt t                                              21

<210> SEQ ID NO 73
<211> LENGTH: 21
```

```
<212> TYPE: DNA
<213> ORGANISM: homo sapiens

<400> SEQUENCE: 73
ugauuauugg gccaaagcca g                                             21

<210> SEQ ID NO 74
<211> LENGTH: 21
<212> TYPE: DNA
<213> ORGANISM: homo sapiens

<400> SEQUENCE: 74
auuuguacaa agcugacaca t                                             21

<210> SEQ ID NO 75
<211> LENGTH: 21
<212> TYPE: DNA
<213> ORGANISM: homo sapiens

<400> SEQUENCE: 75
uaaauauccc gggccaagcc a                                             21

<210> SEQ ID NO 76
<211> LENGTH: 21
<212> TYPE: DNA
<213> ORGANISM: homo sapiens

<400> SEQUENCE: 76
aaccauacca cuguccguct g                                             21

<210> SEQ ID NO 77
<211> LENGTH: 21
<212> TYPE: DNA
<213> ORGANISM: homo sapiens

<400> SEQUENCE: 77
ugucaucgga gugauauccg g                                             21

<210> SEQ ID NO 78
<211> LENGTH: 21
<212> TYPE: DNA
<213> ORGANISM: homo sapiens

<400> SEQUENCE: 78
ucucaaacgu agaucuguct g                                             21

<210> SEQ ID NO 79
<211> LENGTH: 21
<212> TYPE: DNA
<213> ORGANISM: homo sapiens

<400> SEQUENCE: 79
uccuccacaa auccagagct g                                             21

<210> SEQ ID NO 80
<211> LENGTH: 21
<212> TYPE: DNA
<213> ORGANISM: homo sapiens

<400> SEQUENCE: 80
uaaaugaccg aggccaaguc a                                             21

<210> SEQ ID NO 81
<211> LENGTH: 21
```

```
<212> TYPE: DNA
<213> ORGANISM: homo sapiens

<400> SEQUENCE: 81
uaaccaaggu acuucgcagg g                                    21

<210> SEQ ID NO 82
<211> LENGTH: 21
<212> TYPE: DNA
<213> ORGANISM: homo sapiens

<400> SEQUENCE: 82
uaggcaaacc cacagaggcg g                                    21

<210> SEQ ID NO 83
<211> LENGTH: 21
<212> TYPE: DNA
<213> ORGANISM: homo sapiens

<400> SEQUENCE: 83
uggcaucaua aggcagucgt t                                    21

<210> SEQ ID NO 84
<211> LENGTH: 21
<212> TYPE: DNA
<213> ORGANISM: homo sapiens

<400> SEQUENCE: 84
uugaguggug ccguacuggt a                                    21

<210> SEQ ID NO 85
<211> LENGTH: 21
<212> TYPE: DNA
<213> ORGANISM: homo sapiens

<400> SEQUENCE: 85
uuuccaaaga guauccaagt t                                    21

<210> SEQ ID NO 86
<211> LENGTH: 21
<212> TYPE: DNA
<213> ORGANISM: homo sapiens

<400> SEQUENCE: 86
uugucgucug auucuccagg t                                    21

<210> SEQ ID NO 87
<211> LENGTH: 21
<212> TYPE: DNA
<213> ORGANISM: homo sapiens

<400> SEQUENCE: 87
uaagaggaua uuucgugccg c                                    21

<210> SEQ ID NO 88
<211> LENGTH: 21
<212> TYPE: DNA
<213> ORGANISM: homo sapiens

<400> SEQUENCE: 88
uauguacaua auagacuggt a                                    21

<210> SEQ ID NO 89
<211> LENGTH: 21
```

```
<212> TYPE: DNA
<213> ORGANISM: homo sapiens

<400> SEQUENCE: 89
uuacaaguuu cuuaugcuga t                                              21

<210> SEQ ID NO 90
<211> LENGTH: 21
<212> TYPE: DNA
<213> ORGANISM: homo sapiens

<400> SEQUENCE: 90
uaggucucgg uuuacaagut t                                              21

<210> SEQ ID NO 91
<211> LENGTH: 21
<212> TYPE: DNA
<213> ORGANISM: homo sapiens

<400> SEQUENCE: 91
uuaggucucg guuuacaagt t                                              21

<210> SEQ ID NO 92
<211> LENGTH: 21
<212> TYPE: DNA
<213> ORGANISM: homo sapiens

<400> SEQUENCE: 92
uccgauaaga ggauauuucg t                                              21

<210> SEQ ID NO 93
<211> LENGTH: 21
<212> TYPE: DNA
<213> ORGANISM: homo sapiens

<400> SEQUENCE: 93
uuuacaaguu ucuuaugcug a                                              21

<210> SEQ ID NO 94
<211> LENGTH: 21
<212> TYPE: DNA
<213> ORGANISM: homo sapiens

<400> SEQUENCE: 94
ucugauucuc cagguuucct g                                              21

<210> SEQ ID NO 95
<211> LENGTH: 21
<212> TYPE: DNA
<213> ORGANISM: homo sapiens

<400> SEQUENCE: 95
uucaauacaa ugccugaguc t                                              21

<210> SEQ ID NO 96
<211> LENGTH: 21
<212> TYPE: DNA
<213> ORGANISM: homo sapiens

<400> SEQUENCE: 96
uuuguugacc gcuucacaut t                                              21

<210> SEQ ID NO 97
<211> LENGTH: 21
```

```
<212> TYPE: DNA
<213> ORGANISM: homo sapiens

<400> SEQUENCE: 97
auagcugauc auguagcugg g                                              21

<210> SEQ ID NO 98
<211> LENGTH: 21
<212> TYPE: DNA
<213> ORGANISM: homo sapiens

<400> SEQUENCE: 98
uauccggacu gguagccgct t                                              21

<210> SEQ ID NO 99
<211> LENGTH: 21
<212> TYPE: DNA
<213> ORGANISM: homo sapiens

<400> SEQUENCE: 99
uacaugucag cguuugagug g                                              21

<210> SEQ ID NO 100
<211> LENGTH: 21
<212> TYPE: DNA
<213> ORGANISM: homo sapiens

<400> SEQUENCE: 100
uaucggaaga acaauguagt c                                              21

<210> SEQ ID NO 101
<211> LENGTH: 21
<212> TYPE: DNA
<213> ORGANISM: homo sapiens

<400> SEQUENCE: 101
uuccuguuga ccaagagcgt g                                              21

<210> SEQ ID NO 102
<211> LENGTH: 21
<212> TYPE: DNA
<213> ORGANISM: homo sapiens

<400> SEQUENCE: 102
uugagcuccg acaucagcgc g                                              21

<210> SEQ ID NO 103
<211> LENGTH: 21
<212> TYPE: DNA
<213> ORGANISM: homo sapiens

<400> SEQUENCE: 103
uuggauucga uggugaagcc g                                              21

<210> SEQ ID NO 104
<211> LENGTH: 21
<212> TYPE: DNA
<213> ORGANISM: homo sapiens

<400> SEQUENCE: 104
uucaugcaca augaccucgg t                                              21

<210> SEQ ID NO 105
<211> LENGTH: 21
```

```
<212> TYPE: DNA
<213> ORGANISM: homo sapiens

<400> SEQUENCE: 105
uuaccaagga auaaucggcg g                                              21

<210> SEQ ID NO 106
<211> LENGTH: 21
<212> TYPE: DNA
<213> ORGANISM: homo sapiens

<400> SEQUENCE: 106
ucuuuguacc acacgaugct g                                              21

<210> SEQ ID NO 107
<211> LENGTH: 21
<212> TYPE: DNA
<213> ORGANISM: homo sapiens

<400> SEQUENCE: 107
uugcagucga gcagaagcgg g                                              21

<210> SEQ ID NO 108
<211> LENGTH: 21
<212> TYPE: DNA
<213> ORGANISM: homo sapiens

<400> SEQUENCE: 108
uucagcuacc ugaagccgct t                                              21

<210> SEQ ID NO 109
<211> LENGTH: 21
<212> TYPE: DNA
<213> ORGANISM: homo sapiens

<400> SEQUENCE: 109
uacaccuugu cgaagaugct t                                              21

<210> SEQ ID NO 110
<211> LENGTH: 21
<212> TYPE: DNA
<213> ORGANISM: homo sapiens

<400> SEQUENCE: 110
uaccacugga acucgggcgg g                                              21

<210> SEQ ID NO 111
<211> LENGTH: 21
<212> TYPE: DNA
<213> ORGANISM: homo sapiens

<400> SEQUENCE: 111
uagcagacgu agcugccugt g                                              21

<210> SEQ ID NO 112
<211> LENGTH: 21
<212> TYPE: DNA
<213> ORGANISM: homo sapiens

<400> SEQUENCE: 112
uuguggaugc cgaaagcgga g                                              21

<210> SEQ ID NO 113
<211> LENGTH: 21
```

```
<212> TYPE: DNA
<213> ORGANISM: homo sapiens

<400> SEQUENCE: 113
ucacagucuu auucuuuccc t                                              21

<210> SEQ ID NO 114
<211> LENGTH: 21
<212> TYPE: DNA
<213> ORGANISM: homo sapiens

<400> SEQUENCE: 114
uccgugaugu ucaaggucgg g                                              21

<210> SEQ ID NO 115
<211> LENGTH: 21
<212> TYPE: DNA
<213> ORGANISM: homo sapiens

<400> SEQUENCE: 115
auaguggccc ucgugcucgg g                                              21

<210> SEQ ID NO 116
<211> LENGTH: 21
<212> TYPE: DNA
<213> ORGANISM: homo sapiens

<400> SEQUENCE: 116
aagcacugca ucuccagcga g                                              21

<210> SEQ ID NO 117
<211> LENGTH: 21
<212> TYPE: DNA
<213> ORGANISM: homo sapiens

<400> SEQUENCE: 117
ucauagagcu cguugccugt g                                              21

<210> SEQ ID NO 118
<211> LENGTH: 21
<212> TYPE: DNA
<213> ORGANISM: homo sapiens

<400> SEQUENCE: 118
aggaucacga ucuccaugct g                                              21

<210> SEQ ID NO 119
<211> LENGTH: 21
<212> TYPE: DNA
<213> ORGANISM: homo sapiens

<400> SEQUENCE: 119
ucaaguucug cgugagccga g                                              21

<210> SEQ ID NO 120
<211> LENGTH: 21
<212> TYPE: DNA
<213> ORGANISM: homo sapiens

<400> SEQUENCE: 120
ucuguuggga gcgucgcucg g                                              21

<210> SEQ ID NO 121
<211> LENGTH: 21
```

-continued

<212> TYPE: DNA
<213> ORGANISM: homo sapiens

<400> SEQUENCE: 121
uagcccgucu ugaugucugc g                                              21

<210> SEQ ID NO 122
<211> LENGTH: 21
<212> TYPE: DNA
<213> ORGANISM: homo sapiens

<400> SEQUENCE: 122
uucauccugg aggaaccacg g                                              21

<210> SEQ ID NO 123
<211> LENGTH: 21
<212> TYPE: DNA
<213> ORGANISM: homo sapiens

<400> SEQUENCE: 123
aacaccuugc aguagggcct g                                              21

<210> SEQ ID NO 124
<211> LENGTH: 21
<212> TYPE: DNA
<213> ORGANISM: homo sapiens

<400> SEQUENCE: 124
ugcgugguca ccgcccucca g                                              21

<210> SEQ ID NO 125
<211> LENGTH: 21
<212> TYPE: DNA
<213> ORGANISM: homo sapiens

<400> SEQUENCE: 125
ucguaggaca gguauucgca t                                              21

<210> SEQ ID NO 126
<211> LENGTH: 21
<212> TYPE: DNA
<213> ORGANISM: homo sapiens

<400> SEQUENCE: 126
auacgagccc aggucgugct g                                              21

<210> SEQ ID NO 127
<211> LENGTH: 21
<212> TYPE: DNA
<213> ORGANISM: homo sapiens

<400> SEQUENCE: 127
uuguugauga auggcugcuc a                                              21

<210> SEQ ID NO 128
<211> LENGTH: 21
<212> TYPE: DNA
<213> ORGANISM: homo sapiens

<400> SEQUENCE: 128
uagauguccc gggcaaggcc a                                              21

<210> SEQ ID NO 129
<211> LENGTH: 21

```
<212> TYPE: DNA
<213> ORGANISM: homo sapiens

<400> SEQUENCE: 129
uugacgcagc ccuuggguct g                                              21

<210> SEQ ID NO 130
<211> LENGTH: 21
<212> TYPE: DNA
<213> ORGANISM: homo sapiens

<400> SEQUENCE: 130
uucugguugg aguccgccaa g                                              21

<210> SEQ ID NO 131
<211> LENGTH: 21
<212> TYPE: DNA
<213> ORGANISM: homo sapiens

<400> SEQUENCE: 131
ugcaccgaca gguacuucut g                                              21

<210> SEQ ID NO 132
<211> LENGTH: 21
<212> TYPE: DNA
<213> ORGANISM: homo sapiens

<400> SEQUENCE: 132
augcgugccu ugauguacut g                                              21

<210> SEQ ID NO 133
<211> LENGTH: 21
<212> TYPE: DNA
<213> ORGANISM: homo sapiens

<400> SEQUENCE: 133
uacuuguagc ugucggcuug g                                              21

<210> SEQ ID NO 134
<211> LENGTH: 21
<212> TYPE: DNA
<213> ORGANISM: homo sapiens

<400> SEQUENCE: 134
uuccaugguc agcgggcuca g                                              21

<210> SEQ ID NO 135
<211> LENGTH: 21
<212> TYPE: DNA
<213> ORGANISM: homo sapiens

<400> SEQUENCE: 135
uuugagccac ucgacgcuga t                                              21

<210> SEQ ID NO 136
<211> LENGTH: 21
<212> TYPE: DNA
<213> ORGANISM: homo sapiens

<400> SEQUENCE: 136
uucgauggug aagccgucgg g                                              21

<210> SEQ ID NO 137
<211> LENGTH: 21
```

-continued

```
<212> TYPE: DNA
<213> ORGANISM: homo sapiens

<400> SEQUENCE: 137
uaccaaggaa uaaucggcgg g                                             21

<210> SEQ ID NO 138
<211> LENGTH: 21
<212> TYPE: DNA
<213> ORGANISM: homo sapiens

<400> SEQUENCE: 138
ucaugcacaa ugaccucggt g                                             21

<210> SEQ ID NO 139
<211> LENGTH: 21
<212> TYPE: DNA
<213> ORGANISM: homo sapiens

<400> SEQUENCE: 139
uugucgaaga ugcuuucagg g                                             21

<210> SEQ ID NO 140
<211> LENGTH: 21
<212> TYPE: DNA
<213> ORGANISM: homo sapiens

<400> SEQUENCE: 140
uguauuacuc auauuaccaa g                                             21

<210> SEQ ID NO 141
<211> LENGTH: 21
<212> TYPE: DNA
<213> ORGANISM: homo sapiens

<400> SEQUENCE: 141
uucuugucua ugccugcuct c                                             21

<210> SEQ ID NO 142
<211> LENGTH: 21
<212> TYPE: DNA
<213> ORGANISM: homo sapiens

<400> SEQUENCE: 142
uauuaccaag gaauaaucgg c                                             21

<210> SEQ ID NO 143
<211> LENGTH: 21
<212> TYPE: DNA
<213> ORGANISM: homo sapiens

<400> SEQUENCE: 143
uuuguaccac acgaugcugg g                                             21

<210> SEQ ID NO 144
<211> LENGTH: 21
<212> TYPE: DNA
<213> ORGANISM: homo sapiens

<400> SEQUENCE: 144
augaccucgg ugcucucccg a                                             21

<210> SEQ ID NO 145
<211> LENGTH: 21
```

```
<212> TYPE: DNA
<213> ORGANISM: homo sapiens

<400> SEQUENCE: 145
uugaugucug cgugggccgg c                                    21

<210> SEQ ID NO 146
<211> LENGTH: 21
<212> TYPE: DNA
<213> ORGANISM: homo sapiens

<400> SEQUENCE: 146
uguaccacug gaacucgggc g                                    21

<210> SEQ ID NO 147
<211> LENGTH: 21
<212> TYPE: DNA
<213> ORGANISM: homo sapiens

<400> SEQUENCE: 147
ugugucguug gcauguacct c                                    21

<210> SEQ ID NO 148
<211> LENGTH: 21
<212> TYPE: DNA
<213> ORGANISM: homo sapiens

<400> SEQUENCE: 148
augcacguuc uugcagucga g                                    21

<210> SEQ ID NO 149
<211> LENGTH: 21
<212> TYPE: DNA
<213> ORGANISM: homo sapiens

<400> SEQUENCE: 149
ugucguuggc auguaccucg t                                    21

<210> SEQ ID NO 150
<211> LENGTH: 21
<212> TYPE: DNA
<213> ORGANISM: homo sapiens

<400> SEQUENCE: 150
cuggauguca uagagcucgt t                                    21

<210> SEQ ID NO 151
<211> LENGTH: 21
<212> TYPE: DNA
<213> ORGANISM: homo sapiens

<400> SEQUENCE: 151
uaagcuuaca aucuggcccg t                                    21

<210> SEQ ID NO 152
<211> LENGTH: 21
<212> TYPE: DNA
<213> ORGANISM: homo sapiens

<400> SEQUENCE: 152
uaucuucaca ucaacgugct g                                    21

<210> SEQ ID NO 153
<211> LENGTH: 21
```

```
<212> TYPE: DNA
<213> ORGANISM: homo sapiens

<400> SEQUENCE: 153
uauguucacg uuaucuccct t                                              21

<210> SEQ ID NO 154
<211> LENGTH: 21
<212> TYPE: DNA
<213> ORGANISM: homo sapiens

<400> SEQUENCE: 154
uuuaaggaca ccaauaucug g                                              21

<210> SEQ ID NO 155
<211> LENGTH: 21
<212> TYPE: DNA
<213> ORGANISM: homo sapiens

<400> SEQUENCE: 155
ugaaauuuga ugucauucca g                                              21

<210> SEQ ID NO 156
<211> LENGTH: 21
<212> TYPE: DNA
<213> ORGANISM: homo sapiens

<400> SEQUENCE: 156
uuguuuacaa guuagaggca a                                              21

<210> SEQ ID NO 157
<211> LENGTH: 21
<212> TYPE: DNA
<213> ORGANISM: homo sapiens

<400> SEQUENCE: 157
uucauugcac ugcagacccu t                                              21

<210> SEQ ID NO 158
<211> LENGTH: 21
<212> TYPE: DNA
<213> ORGANISM: homo sapiens

<400> SEQUENCE: 158
uagaauauca gguacuucat g                                              21

<210> SEQ ID NO 159
<211> LENGTH: 21
<212> TYPE: DNA
<213> ORGANISM: homo sapiens

<400> SEQUENCE: 159
uucaauugca auaugaucag a                                              21

<210> SEQ ID NO 160
<211> LENGTH: 21
<212> TYPE: DNA
<213> ORGANISM: homo sapiens

<400> SEQUENCE: 160
uagccaucca auauugucca a                                              21

<210> SEQ ID NO 161
<211> LENGTH: 21
```

<212> TYPE: DNA
<213> ORGANISM: homo sapiens

<400> SEQUENCE: 161
uacuucuaua ugaucuggca a                                              21

<210> SEQ ID NO 162
<211> LENGTH: 21
<212> TYPE: DNA
<213> ORGANISM: homo sapiens

<400> SEQUENCE: 162
uuugguauca gcagggcugg g                                              21

<210> SEQ ID NO 163
<211> LENGTH: 21
<212> TYPE: DNA
<213> ORGANISM: homo sapiens

<400> SEQUENCE: 163
uguacuauca gggucauugt t                                              21

<210> SEQ ID NO 164
<211> LENGTH: 21
<212> TYPE: DNA
<213> ORGANISM: homo sapiens

<400> SEQUENCE: 164
uucugauuuc agcccauuct t                                              21

<210> SEQ ID NO 165
<211> LENGTH: 21
<212> TYPE: DNA
<213> ORGANISM: homo sapiens

<400> SEQUENCE: 165
uuguugacgc aucuucaugg t                                              21

<210> SEQ ID NO 166
<211> LENGTH: 21
<212> TYPE: DNA
<213> ORGANISM: homo sapiens

<400> SEQUENCE: 166
auagcauuca acauaaaggt a                                              21

<210> SEQ ID NO 167
<211> LENGTH: 21
<212> TYPE: DNA
<213> ORGANISM: homo sapiens

<400> SEQUENCE: 167
uuugugacuu uccauuagca t                                              21

<210> SEQ ID NO 168
<211> LENGTH: 21
<212> TYPE: DNA
<213> ORGANISM: homo sapiens

<400> SEQUENCE: 168
uaaaugaaac gggacuggct g                                              21

<210> SEQ ID NO 169
<211> LENGTH: 21

```
<212> TYPE: DNA
<213> ORGANISM: homo sapiens

<400> SEQUENCE: 169
uacuaauugu acucacgcct t                                              21

<210> SEQ ID NO 170
<211> LENGTH: 21
<212> TYPE: DNA
<213> ORGANISM: homo sapiens

<400> SEQUENCE: 170
uugaauaugu ugccaagcct c                                              21

<210> SEQ ID NO 171
<211> LENGTH: 21
<212> TYPE: DNA
<213> ORGANISM: homo sapiens

<400> SEQUENCE: 171
uuauugcaua ugaaaccaca a                                              21

<210> SEQ ID NO 172
<211> LENGTH: 21
<212> TYPE: DNA
<213> ORGANISM: homo sapiens

<400> SEQUENCE: 172
uaaagcgugg uauucacgua g                                              21

<210> SEQ ID NO 173
<211> LENGTH: 21
<212> TYPE: DNA
<213> ORGANISM: homo sapiens

<400> SEQUENCE: 173
auuaaggcuu caaagucccu t                                              21

<210> SEQ ID NO 174
<211> LENGTH: 21
<212> TYPE: DNA
<213> ORGANISM: homo sapiens

<400> SEQUENCE: 174
uucugcacaa gucaucccgc a                                              21

<210> SEQ ID NO 175
<211> LENGTH: 21
<212> TYPE: DNA
<213> ORGANISM: homo sapiens

<400> SEQUENCE: 175
uaaauuguag gaucugggut g                                              21

<210> SEQ ID NO 176
<211> LENGTH: 21
<212> TYPE: DNA
<213> ORGANISM: homo sapiens

<400> SEQUENCE: 176
uaguugagug uaacaaucuc a                                              21

<210> SEQ ID NO 177
<211> LENGTH: 21
```

```
<212> TYPE: DNA
<213> ORGANISM: homo sapiens

<400> SEQUENCE: 177
uaagcuaaca aucucccaua g                                              21

<210> SEQ ID NO 178
<211> LENGTH: 21
<212> TYPE: DNA
<213> ORGANISM: homo sapiens

<400> SEQUENCE: 178
uaaggcucag agcugaugut g                                              21

<210> SEQ ID NO 179
<211> LENGTH: 21
<212> TYPE: DNA
<213> ORGANISM: homo sapiens

<400> SEQUENCE: 179
auguccagug ucaaucacgt t                                              21

<210> SEQ ID NO 180
<211> LENGTH: 21
<212> TYPE: DNA
<213> ORGANISM: homo sapiens

<400> SEQUENCE: 180
uucuguccua ggccgcuuct t                                              21

<210> SEQ ID NO 181
<211> LENGTH: 21
<212> TYPE: DNA
<213> ORGANISM: homo sapiens

<400> SEQUENCE: 181
uuaaguagca ccgaagucaa g                                              21

<210> SEQ ID NO 182
<211> LENGTH: 21
<212> TYPE: DNA
<213> ORGANISM: homo sapiens

<400> SEQUENCE: 182
uaacccaucc uucuugaugc g                                              21

<210> SEQ ID NO 183
<211> LENGTH: 21
<212> TYPE: DNA
<213> ORGANISM: homo sapiens

<400> SEQUENCE: 183
uugguugcca ggucaaauut a                                              21

<210> SEQ ID NO 184
<211> LENGTH: 21
<212> TYPE: DNA
<213> ORGANISM: homo sapiens

<400> SEQUENCE: 184
uagauuagga ugggaaaggc t                                              21

<210> SEQ ID NO 185
<211> LENGTH: 21
```

```
<212> TYPE: DNA
<213> ORGANISM: homo sapiens

<400> SEQUENCE: 185
uucuccaguc uguagcccug g                                              21

<210> SEQ ID NO 186
<211> LENGTH: 21
<212> TYPE: DNA
<213> ORGANISM: homo sapiens

<400> SEQUENCE: 186
uugaaauuug augucauucc a                                              21

<210> SEQ ID NO 187
<211> LENGTH: 21
<212> TYPE: DNA
<213> ORGANISM: homo sapiens

<400> SEQUENCE: 187
uuaaggacac caauaucugg g                                              21

<210> SEQ ID NO 188
<211> LENGTH: 21
<212> TYPE: DNA
<213> ORGANISM: homo sapiens

<400> SEQUENCE: 188
uuugaaagau auguucacgt t                                              21

<210> SEQ ID NO 189
<211> LENGTH: 21
<212> TYPE: DNA
<213> ORGANISM: homo sapiens

<400> SEQUENCE: 189
uuuacuucua uaugaucugg c                                              21

<210> SEQ ID NO 190
<211> LENGTH: 21
<212> TYPE: DNA
<213> ORGANISM: homo sapiens

<400> SEQUENCE: 190
uuaucuucac aucaacgugc t                                              21

<210> SEQ ID NO 191
<211> LENGTH: 21
<212> TYPE: DNA
<213> ORGANISM: homo sapiens

<400> SEQUENCE: 191
ugacuuucca uuagcaucgt c                                              21

<210> SEQ ID NO 192
<211> LENGTH: 21
<212> TYPE: DNA
<213> ORGANISM: homo sapiens

<400> SEQUENCE: 192
aauuguacuc acgccuucct a                                              21

<210> SEQ ID NO 193
<211> LENGTH: 21
```

```
<212> TYPE: DNA
<213> ORGANISM: homo sapiens

<400> SEQUENCE: 193
auacuaauug uacucacgcc t                                          21

<210> SEQ ID NO 194
<211> LENGTH: 21
<212> TYPE: DNA
<213> ORGANISM: homo sapiens

<400> SEQUENCE: 194
uuuaucuuca caucaacgug c                                          21

<210> SEQ ID NO 195
<211> LENGTH: 21
<212> TYPE: DNA
<213> ORGANISM: homo sapiens

<400> SEQUENCE: 195
uauacuaauu guacucacgc c                                          21

<210> SEQ ID NO 196
<211> LENGTH: 21
<212> TYPE: DNA
<213> ORGANISM: homo sapiens

<400> SEQUENCE: 196
ugucacuuga auauguugcc a                                          21

<210> SEQ ID NO 197
<211> LENGTH: 21
<212> TYPE: DNA
<213> ORGANISM: homo sapiens

<400> SEQUENCE: 197
uccuaagcua acaaucuccc a                                          21

<210> SEQ ID NO 198
<211> LENGTH: 21
<212> TYPE: DNA
<213> ORGANISM: homo sapiens

<400> SEQUENCE: 198
aucuucaugg uucguaucct g                                          21

<210> SEQ ID NO 199
<211> LENGTH: 21
<212> TYPE: DNA
<213> ORGANISM: homo sapiens

<400> SEQUENCE: 199
uccuuuguag auuaggaugg g                                          21

<210> SEQ ID NO 200
<211> LENGTH: 21
<212> TYPE: DNA
<213> ORGANISM: homo sapiens

<400> SEQUENCE: 200
auauguucac guuaucuccc t                                          21

<210> SEQ ID NO 201
<211> LENGTH: 21
```

<210> SEQ ID NO 201
<211> LENGTH: 21
<212> TYPE: DNA
<213> ORGANISM: homo sapiens

<400> SEQUENCE: 201
uaaaucucug guaacgaccc t        21

<210> SEQ ID NO 202
<211> LENGTH: 21
<212> TYPE: DNA
<213> ORGANISM: homo sapiens

<400> SEQUENCE: 202
uuacacauga acuccacgut g        21

<210> SEQ ID NO 203
<211> LENGTH: 21
<212> TYPE: DNA
<213> ORGANISM: homo sapiens

<400> SEQUENCE: 203
uauacucaga uuuaucaact t        21

<210> SEQ ID NO 204
<211> LENGTH: 21
<212> TYPE: DNA
<213> ORGANISM: homo sapiens

<400> SEQUENCE: 204
uagcggugca gaguguggct g        21

<210> SEQ ID NO 205
<211> LENGTH: 21
<212> TYPE: DNA
<213> ORGANISM: homo sapiens

<400> SEQUENCE: 205
uucaaacuga cccucgcucg g        21

<210> SEQ ID NO 206
<211> LENGTH: 21
<212> TYPE: DNA
<213> ORGANISM: homo sapiens

<400> SEQUENCE: 206
uucugcaguu agagguuggt g        21

<210> SEQ ID NO 207
<211> LENGTH: 21
<212> TYPE: DNA
<213> ORGANISM: homo sapiens

<400> SEQUENCE: 207
aucggaauua auaagccact g        21

<210> SEQ ID NO 208
<211> LENGTH: 21
<212> TYPE: DNA
<213> ORGANISM: homo sapiens

<400> SEQUENCE: 208
uacaagggac cauccugcgt g        21

<210> SEQ ID NO 209
<211> LENGTH: 21

```
<212> TYPE: DNA
<213> ORGANISM: homo sapiens

<400> SEQUENCE: 209
uuguuggcgg gcaacccugc t                                              21

<210> SEQ ID NO 210
<211> LENGTH: 21
<212> TYPE: DNA
<213> ORGANISM: homo sapiens

<400> SEQUENCE: 210
auagcaacug augccuccca g                                              21

<210> SEQ ID NO 211
<211> LENGTH: 21
<212> TYPE: DNA
<213> ORGANISM: homo sapiens

<400> SEQUENCE: 211
ugaggguuac agcugacggt g                                              21

<210> SEQ ID NO 212
<211> LENGTH: 21
<212> TYPE: DNA
<213> ORGANISM: homo sapiens

<400> SEQUENCE: 212
ucgauguggu gaaugucccg t                                              21

<210> SEQ ID NO 213
<211> LENGTH: 21
<212> TYPE: DNA
<213> ORGANISM: homo sapiens

<400> SEQUENCE: 213
ucucggugua ugcacuucut g                                              21

<210> SEQ ID NO 214
<211> LENGTH: 21
<212> TYPE: DNA
<213> ORGANISM: homo sapiens

<400> SEQUENCE: 214
uuucucuguu gcguccgact t                                              21

<210> SEQ ID NO 215
<211> LENGTH: 21
<212> TYPE: DNA
<213> ORGANISM: homo sapiens

<400> SEQUENCE: 215
uucuccacaa ugcaggugua g                                              21

<210> SEQ ID NO 216
<211> LENGTH: 21
<212> TYPE: DNA
<213> ORGANISM: homo sapiens

<400> SEQUENCE: 216 uugucgggc caaucuugct c                                               21

<210> SEQ ID NO 217
<211> LENGTH: 21
```

```
<212> TYPE: DNA
<213> ORGANISM: homo sapiens

<400> SEQUENCE: 217
uccggucaaa uaaugccucg g                                           21

<210> SEQ ID NO 218
<211> LENGTH: 21
<212> TYPE: DNA
<213> ORGANISM: homo sapiens

<400> SEQUENCE: 218
uuugaguccg ccauuggcaa g                                           21

<210> SEQ ID NO 219
<211> LENGTH: 21
<212> TYPE: DNA
<213> ORGANISM: homo sapiens

<400> SEQUENCE: 219
uuugccuaag accagucugt c                                           21

<210> SEQ ID NO 220
<211> LENGTH: 21
<212> TYPE: DNA
<213> ORGANISM: homo sapiens

<400> SEQUENCE: 220
uccagcaguc uucaagauct g                                           21

<210> SEQ ID NO 221
<211> LENGTH: 21
<212> TYPE: DNA
<213> ORGANISM: homo sapiens

<400> SEQUENCE: 221
uccgauagag uuacccgcca a                                           21

<210> SEQ ID NO 222
<211> LENGTH: 21
<212> TYPE: DNA
<213> ORGANISM: homo sapiens

<400> SEQUENCE: 222
uugucagagg gcaccacaga g                                           21

<210> SEQ ID NO 223
<211> LENGTH: 21
<212> TYPE: DNA
<213> ORGANISM: homo sapiens

<400> SEQUENCE: 223
uuggaggcau acuccacgat g                                           21

<210> SEQ ID NO 224
<211> LENGTH: 21
<212> TYPE: DNA
<213> ORGANISM: homo sapiens

<400> SEQUENCE: 224
ucucgguccc gaccggacgt g                                           21

<210> SEQ ID NO 225
<211> LENGTH: 21
```

```
<212> TYPE: DNA
<213> ORGANISM: homo sapiens

<400> SEQUENCE: 225
ucugguacca ggcauuuggt c                                      21

<210> SEQ ID NO 226
<211> LENGTH: 21
<212> TYPE: DNA
<213> ORGANISM: homo sapiens

<400> SEQUENCE: 226
uuguccagcc cgauagccuc t                                      21

<210> SEQ ID NO 227
<211> LENGTH: 21
<212> TYPE: DNA
<213> ORGANISM: homo sapiens

<400> SEQUENCE: 227
uuuagccacu ggaugugcgg c                                      21

<210> SEQ ID NO 228
<211> LENGTH: 21
<212> TYPE: DNA
<213> ORGANISM: homo sapiens

<400> SEQUENCE: 228
uguagccucc aauucugugg t                                      21

<210> SEQ ID NO 229
<211> LENGTH: 21
<212> TYPE: DNA
<213> ORGANISM: homo sapiens

<400> SEQUENCE: 229
uucaaucgug gcucgaagca c                                      21

<210> SEQ ID NO 230
<211> LENGTH: 21
<212> TYPE: DNA
<213> ORGANISM: homo sapiens

<400> SEQUENCE: 230 aucccaugg auacuccaca g                                       21

<210> SEQ ID NO 231
<211> LENGTH: 21
<212> TYPE: DNA
<213> ORGANISM: homo sapiens

<400> SEQUENCE: 231
uuucaaccag cgcagugugg g                                      21

<210> SEQ ID NO 232
<211> LENGTH: 21
<212> TYPE: DNA
<213> ORGANISM: homo sapiens

<400> SEQUENCE: 232
uagagcuccg ggugucggga a                                      21

<210> SEQ ID NO 233
<211> LENGTH: 21
```

```
<212> TYPE: DNA
<213> ORGANISM: homo sapiens

<400> SEQUENCE: 233
uuaccgaugg guaaaucuct g                                      21

<210> SEQ ID NO 234
<211> LENGTH: 21
<212> TYPE: DNA
<213> ORGANISM: homo sapiens

<400> SEQUENCE: 234
aaaucucugg uaacgaccct t                                      21

<210> SEQ ID NO 235
<211> LENGTH: 21
<212> TYPE: DNA
<213> ORGANISM: homo sapiens

<400> SEQUENCE: 235
uauagcaacu gaugccuccc a                                      21

<210> SEQ ID NO 236
<211> LENGTH: 21
<212> TYPE: DNA
<213> ORGANISM: homo sapiens

<400> SEQUENCE: 236
uuucaaacug acccucgcuc g                                      21

<210> SEQ ID NO 237
<211> LENGTH: 21
<212> TYPE: DNA
<213> ORGANISM: homo sapiens

<400> SEQUENCE: 237
auacucagau uuaucaacut t                                      21

<210> SEQ ID NO 238
<211> LENGTH: 21
<212> TYPE: DNA
<213> ORGANISM: homo sapiens

<400> SEQUENCE: 238
uaccgauggg uaaaucucug g                                      21

<210> SEQ ID NO 239
<211> LENGTH: 21
<212> TYPE: DNA
<213> ORGANISM: homo sapiens

<400> SEQUENCE: 239
auacaaggga ccauccugcg t                                      21

<210> SEQ ID NO 240
<211> LENGTH: 21
<212> TYPE: DNA
<213> ORGANISM: homo sapiens

<400> SEQUENCE: 240
uacucagauu uaucaacuut g                                      21

<210> SEQ ID NO 241
<211> LENGTH: 21
```

```
<212> TYPE: DNA
<213> ORGANISM: homo sapiens

<400> SEQUENCE: 241
ucgguguaug cacuucuugg a                                              21

<210> SEQ ID NO 242
<211> LENGTH: 21
<212> TYPE: DNA
<213> ORGANISM: homo sapiens

<400> SEQUENCE: 242
uacuccacga ugacauacaa g                                              21

<210> SEQ ID NO 243
<211> LENGTH: 21
<212> TYPE: DNA
<213> ORGANISM: homo sapiens

<400> SEQUENCE: 243
ucggaauuaa uaagccacug g                                              21

<210> SEQ ID NO 244
<211> LENGTH: 21
<212> TYPE: DNA
<213> ORGANISM: homo sapiens

<400> SEQUENCE: 244
acagagucca uuaugaugct c                                              21

<210> SEQ ID NO 245
<211> LENGTH: 21
<212> TYPE: DNA
<213> ORGANISM: homo sapiens

<400> SEQUENCE: 245
uuugucggug guauuaacuc c                                              21

<210> SEQ ID NO 246
<211> LENGTH: 21
<212> TYPE: DNA
<213> ORGANISM: homo sapiens

<400> SEQUENCE: 246
gaguccauua ugaugcucca g                                              21

<210> SEQ ID NO 247
<211> LENGTH: 21
<212> TYPE: DNA
<213> ORGANISM: homo sapiens

<400> SEQUENCE: 247
uaucggaauu aauaagccac t                                              21

<210> SEQ ID NO 248
<211> LENGTH: 21
<212> TYPE: DNA
<213> ORGANISM: homo sapiens

<400> SEQUENCE: 248
auccggucaa auaaugccuc g                                              21

<210> SEQ ID NO 249
<211> LENGTH: 21
```

```
<212> TYPE: DNA
<213> ORGANISM: homo sapiens

<400> SEQUENCE: 249
uucucuguug cguccgacut c                                              21

<210> SEQ ID NO 250
<211> LENGTH: 21
<212> TYPE: DNA
<213> ORGANISM: homo sapiens

<400> SEQUENCE: 250
auguggugaa ugucccgugc g                                              21

<210> SEQ ID NO 251
<211> LENGTH: 21
<212> TYPE: DNA
<213> ORGANISM: homo sapiens

<400> SEQUENCE: 251
uuuauuagga acaucugcct g                                              21

<210> SEQ ID NO 252
<211> LENGTH: 21
<212> TYPE: DNA
<213> ORGANISM: homo sapiens

<400> SEQUENCE: 252
uugaucuaac ugaagcaccg g                                              21

<210> SEQ ID NO 253
<211> LENGTH: 21
<212> TYPE: DNA
<213> ORGANISM: homo sapiens

<400> SEQUENCE: 253
auuguuugga ugguaagcct g                                              21

<210> SEQ ID NO 254
<211> LENGTH: 21
<212> TYPE: DNA
<213> ORGANISM: homo sapiens

<400> SEQUENCE: 254
uaauuagcca guuagugggt t                                              21

<210> SEQ ID NO 255
<211> LENGTH: 21
<212> TYPE: DNA
<213> ORGANISM: homo sapiens

<400> SEQUENCE: 255
uucguuucca uggaggugca a                                              21

<210> SEQ ID NO 256
<211> LENGTH: 21
<212> TYPE: DNA
<213> ORGANISM: homo sapiens

<400> SEQUENCE: 256
ucaucuaaug ucagauucgg g                                              21

<210> SEQ ID NO 257
<211> LENGTH: 21
```

```
<212> TYPE: DNA
<213> ORGANISM: homo sapiens

<400> SEQUENCE: 257
uacuuguuga gugucucagt t                                              21

<210> SEQ ID NO 258
<211> LENGTH: 21
<212> TYPE: DNA
<213> ORGANISM: homo sapiens

<400> SEQUENCE: 258
augacgugcc aagaacuccu u                                              21

<210> SEQ ID NO 259
<211> LENGTH: 21
<212> TYPE: DNA
<213> ORGANISM: homo sapiens

<400> SEQUENCE: 259
uuucccagga ccucauagca a                                              21

<210> SEQ ID NO 260
<211> LENGTH: 21
<212> TYPE: DNA
<213> ORGANISM: homo sapiens

<400> SEQUENCE: 260
aagagauauu ccuucaucga t                                              21

<210> SEQ ID NO 261
<211> LENGTH: 21
<212> TYPE: DNA
<213> ORGANISM: homo sapiens

<400> SEQUENCE: 261
uugaggagau gcuccuguga g                                              21

<210> SEQ ID NO 262
<211> LENGTH: 21
<212> TYPE: DNA
<213> ORGANISM: homo sapiens

<400> SEQUENCE: 262
ucuuguggca uagaucuggc u                                              21

<210> SEQ ID NO 263
<211> LENGTH: 21
<212> TYPE: DNA
<213> ORGANISM: homo sapiens

<400> SEQUENCE: 263
auagugccug uccagagcca g                                              21

<210> SEQ ID NO 264
<211> LENGTH: 21
<212> TYPE: DNA
<213> ORGANISM: homo sapiens

<400> SEQUENCE: 264
ucaacgagag cauccagccc u                                              21

<210> SEQ ID NO 265
<211> LENGTH: 21
```

```
<212> TYPE: DNA
<213> ORGANISM: homo sapiens

<400> SEQUENCE: 265
augcauagcc aggaucuuga g                                          21

<210> SEQ ID NO 266
<211> LENGTH: 21
<212> TYPE: DNA
<213> ORGANISM: homo sapiens

<400> SEQUENCE: 266
uuggagguac cucaacagct c                                          21

<210> SEQ ID NO 267
<211> LENGTH: 21
<212> TYPE: DNA
<213> ORGANISM: homo sapiens

<400> SEQUENCE: 267
ucaggguguu gguuauucut t                                          21

<210> SEQ ID NO 268
<211> LENGTH: 21
<212> TYPE: DNA
<213> ORGANISM: homo sapiens

<400> SEQUENCE: 268
aucuguaaua uuugacaugt c                                          21

<210> SEQ ID NO 269
<211> LENGTH: 21
<212> TYPE: DNA
<213> ORGANISM: homo sapiens

<400> SEQUENCE: 269
ugcuugucuc guuccacuug g                                          21

<210> SEQ ID NO 270
<211> LENGTH: 21
<212> TYPE: DNA
<213> ORGANISM: homo sapiens

<400> SEQUENCE: 270
uucagagguu ggaagagaca t                                          21

<210> SEQ ID NO 271
<211> LENGTH: 21
<212> TYPE: DNA
<213> ORGANISM: homo sapiens

<400> SEQUENCE: 271
uuggauggua agccuggcgg a                                          21

<210> SEQ ID NO 272
<211> LENGTH: 21
<212> TYPE: DNA
<213> ORGANISM: homo sapiens

<400> SEQUENCE: 272
uaaagaugug acguucaacg g                                          21

<210> SEQ ID NO 273
<211> LENGTH: 21
```

```
<212> TYPE: DNA
<213> ORGANISM: homo sapiens

<400> SEQUENCE: 273
ucuaacugaa gcaccggcca g                                         21

<210> SEQ ID NO 274
<211> LENGTH: 21
<212> TYPE: DNA
<213> ORGANISM: homo sapiens

<400> SEQUENCE: 274
ucaacgggaa ugauggugct t                                         21

<210> SEQ ID NO 275
<211> LENGTH: 21
<212> TYPE: DNA
<213> ORGANISM: homo sapiens

<400> SEQUENCE: 275
uuguuuggau gguaagccug g                                         21

<210> SEQ ID NO 276
<211> LENGTH: 21
<212> TYPE: DNA
<213> ORGANISM: homo sapiens

<400> SEQUENCE: 276
uuuggauggu aagccuggcg g                                         21

<210> SEQ ID NO 277
<211> LENGTH: 21
<212> TYPE: DNA
<213> ORGANISM: homo sapiens

<400> SEQUENCE: 277
uuugaucuaa cugaagcacc g                                         21

<210> SEQ ID NO 278
<211> LENGTH: 21
<212> TYPE: DNA
<213> ORGANISM: homo sapiens

<400> SEQUENCE: 278
uucaacggga augauggugc t                                         21

<210> SEQ ID NO 279
<211> LENGTH: 21
<212> TYPE: DNA
<213> ORGANISM: homo sapiens

<400> SEQUENCE: 279
ugcuucguuu ccauggaggt g                                         21

<210> SEQ ID NO 280
<211> LENGTH: 21
<212> TYPE: DNA
<213> ORGANISM: homo sapiens

<400> SEQUENCE: 280
ucuggcuucc aaacccucut t                                         21

<210> SEQ ID NO 281
<211> LENGTH: 21
```

```
<212> TYPE: DNA
<213> ORGANISM: homo sapiens

<400> SEQUENCE: 281
augcuaauua gccaguuagt g                                              21

<210> SEQ ID NO 282
<211> LENGTH: 21
<212> TYPE: DNA
<213> ORGANISM: homo sapiens

<400> SEQUENCE: 282
agauauuccu ucaucgaugg t                                              21

<210> SEQ ID NO 283
<211> LENGTH: 21
<212> TYPE: DNA
<213> ORGANISM: homo sapiens

<400> SEQUENCE: 283
uuauuaggaa caucugccug c                                              21

<210> SEQ ID NO 284
<211> LENGTH: 21
<212> TYPE: DNA
<213> ORGANISM: homo sapiens

<400> SEQUENCE: 284
cuaauuagcc aguuaguggg t                                              21

<210> SEQ ID NO 285
<211> LENGTH: 21
<212> TYPE: DNA
<213> ORGANISM: homo sapiens

<400> SEQUENCE: 285
ugaucuaacu gaagcaccgg c                                              21

<210> SEQ ID NO 286
<211> LENGTH: 21
<212> TYPE: DNA
<213> ORGANISM: homo sapiens

<400> SEQUENCE: 286
aauuguuugg augguaagcc t                                              21

<210> SEQ ID NO 287
<211> LENGTH: 21
<212> TYPE: DNA
<213> ORGANISM: homo sapiens

<400> SEQUENCE: 287
uggaugguaa gccuggcgga a                                              21

<210> SEQ ID NO 288
<211> LENGTH: 21
<212> TYPE: DNA
<213> ORGANISM: homo sapiens

<400> SEQUENCE: 288
uugcugacca ggccaugcat a                                              21

<210> SEQ ID NO 289
<211> LENGTH: 21
```

```
<212> TYPE: DNA
<213> ORGANISM: homo sapiens

<400> SEQUENCE: 289
aucuggcuuc caaacccuct t                                        21

<210> SEQ ID NO 290
<211> LENGTH: 21
<212> TYPE: DNA
<213> ORGANISM: homo sapiens

<400> SEQUENCE: 290 aauggiuuga ucuaacugaa g                                        21

<210> SEQ ID NO 291
<211> LENGTH: 21
<212> TYPE: DNA
<213> ORGANISM: homo sapiens

<400> SEQUENCE: 291
uccauggagg ugcaaaggcc g                                        21

<210> SEQ ID NO 292
<211> LENGTH: 21
<212> TYPE: DNA
<213> ORGANISM: homo sapiens

<400> SEQUENCE: 292
augauggugc uucguuucca t                                        21

<210> SEQ ID NO 293
<211> LENGTH: 21
<212> TYPE: DNA
<213> ORGANISM: homo sapiens

<400> SEQUENCE: 293
uguuuggaug guaagccugg c                                        21

<210> SEQ ID NO 294
<211> LENGTH: 21
<212> TYPE: DNA
<213> ORGANISM: homo sapiens

<400> SEQUENCE: 294 uucuugiggc auagaucugg c                                        21

<210> SEQ ID NO 295
<211> LENGTH: 21
<212> TYPE: DNA
<213> ORGANISM: homo sapiens

<400> SEQUENCE: 295
agggucaacg agagcaucca g                                        21

<210> SEQ ID NO 296
<211> LENGTH: 21
<212> TYPE: DNA
<213> ORGANISM: homo sapiens

<400> SEQUENCE: 296
auaggcgaug aucacaacat a                                        21

<210> SEQ ID NO 297
<211> LENGTH: 21
```

```
<212> TYPE: DNA
<213> ORGANISM: homo sapiens

<400> SEQUENCE: 297
auacuuguug agugucucag t                                          21

<210> SEQ ID NO 298
<211> LENGTH: 21
<212> TYPE: DNA
<213> ORGANISM: homo sapiens

<400> SEQUENCE: 298
aaugauggug cuucguuucc a                                          21

<210> SEQ ID NO 299
<211> LENGTH: 21
<212> TYPE: DNA
<213> ORGANISM: homo sapiens

<400> SEQUENCE: 299
cuuuauuagg aacaucugcc t                                          21

<210> SEQ ID NO 300
<211> LENGTH: 21
<212> TYPE: DNA
<213> ORGANISM: homo sapiens

<400> SEQUENCE: 300
uaggagguaa cacgaugacg t                                          21

<210> SEQ ID NO 301
<211> LENGTH: 21
<212> TYPE: DNA
<213> ORGANISM: homo sapiens

<400> SEQUENCE: 301
uuaaguguca auuuaguggc a                                          21

<210> SEQ ID NO 302
<211> LENGTH: 21
<212> TYPE: DNA
<213> ORGANISM: homo sapiens

<400> SEQUENCE: 302
uuucuugugg gucaauucct a                                          21

<210> SEQ ID NO 303
<211> LENGTH: 21
<212> TYPE: DNA
<213> ORGANISM: homo sapiens

<400> SEQUENCE: 303
uugggucuug ugaauaagct g                                          21

<210> SEQ ID NO 304
<211> LENGTH: 21
<212> TYPE: DNA
<213> ORGANISM: homo sapiens

<400> SEQUENCE: 304
uucacuucuu agaacauaga g                                          21

<210> SEQ ID NO 305
<211> LENGTH: 21
```

```
<212> TYPE: DNA
<213> ORGANISM: homo sapiens

<400> SEQUENCE: 305
uuggaugagu agacggucct t                                              21

<210> SEQ ID NO 306
<211> LENGTH: 21
<212> TYPE: DNA
<213> ORGANISM: homo sapiens

<400> SEQUENCE: 306
auuacuaaga ucuucaccut t                                              21

<210> SEQ ID NO 307
<211> LENGTH: 21
<212> TYPE: DNA
<213> ORGANISM: homo sapiens

<400> SEQUENCE: 307
uugguuuaau cagccuuggt g                                              21

<210> SEQ ID NO 308
<211> LENGTH: 21
<212> TYPE: DNA
<213> ORGANISM: homo sapiens

<400> SEQUENCE: 308
aucacuacug uuuaucugca g                                              21

<210> SEQ ID NO 309
<211> LENGTH: 21
<212> TYPE: DNA
<213> ORGANISM: homo sapiens

<400> SEQUENCE: 309
auccguaaca gcauccgcca g                                              21

<210> SEQ ID NO 310
<211> LENGTH: 21
<212> TYPE: DNA
<213> ORGANISM: homo sapiens

<400> SEQUENCE: 310
auguauagcu agaaucuuga g                                              21

<210> SEQ ID NO 311
<211> LENGTH: 21
<212> TYPE: DNA
<213> ORGANISM: homo sapiens

<400> SEQUENCE: 311
aagaugaccc gcauggcccg g                                              21

<210> SEQ ID NO 312
<211> LENGTH: 21
<212> TYPE: DNA
<213> ORGANISM: homo sapiens

<400> SEQUENCE: 312
ucucaguacc ucauguaggt g                                              21

<210> SEQ ID NO 313
<211> LENGTH: 21
```

```
<212> TYPE: DNA
<213> ORGANISM: homo sapiens

<400> SEQUENCE: 313
uuugaccaag uagcgcuuct g                                              21

<210> SEQ ID NO 314
<211> LENGTH: 21
<212> TYPE: DNA
<213> ORGANISM: homo sapiens

<400> SEQUENCE: 314
uucguuaggu acauaucaca t                                              21

<210> SEQ ID NO 315
<211> LENGTH: 21
<212> TYPE: DNA
<213> ORGANISM: homo sapiens

<400> SEQUENCE: 315
augaguacuu cauuccucut t                                              21

<210> SEQ ID NO 316
<211> LENGTH: 21
<212> TYPE: DNA
<213> ORGANISM: homo sapiens

<400> SEQUENCE: 316
uuggguggua gucagagcug t                                              21

<210> SEQ ID NO 317
<211> LENGTH: 21
<212> TYPE: DNA
<213> ORGANISM: homo sapiens

<400> SEQUENCE: 317
uuucuaaacc augcaaggga a                                              21

<210> SEQ ID NO 318
<211> LENGTH: 21
<212> TYPE: DNA
<213> ORGANISM: homo sapiens

<400> SEQUENCE: 318
ucauguguua auucuauguc t                                              21

<210> SEQ ID NO 319
<211> LENGTH: 21
<212> TYPE: DNA
<213> ORGANISM: homo sapiens

<400> SEQUENCE: 319
uuaagucaca uugcgguaca a                                              21

<210> SEQ ID NO 320
<211> LENGTH: 21
<212> TYPE: DNA
<213> ORGANISM: homo sapiens

<400> SEQUENCE: 320
uguauuguug cccaugucct c                                              21

<210> SEQ ID NO 321
<211> LENGTH: 21
```

```
<212> TYPE: DNA
<213> ORGANISM: homo sapiens

<400> SEQUENCE: 321
ugaccugcug uuauuggagt g                                              21

<210> SEQ ID NO 322
<211> LENGTH: 21
<212> TYPE: DNA
<213> ORGANISM: homo sapiens

<400> SEQUENCE: 322
aaauauaggc aggugguuct a                                              21

<210> SEQ ID NO 323
<211> LENGTH: 21
<212> TYPE: DNA
<213> ORGANISM: homo sapiens

<400> SEQUENCE: 323
accuugacga ugaaacuuct g                                              21

<210> SEQ ID NO 324
<211> LENGTH: 21
<212> TYPE: DNA
<213> ORGANISM: homo sapiens

<400> SEQUENCE: 324
uuucaagguu cguccgugut g                                              21

<210> SEQ ID NO 325
<211> LENGTH: 21
<212> TYPE: DNA
<213> ORGANISM: homo sapiens

<400> SEQUENCE: 325
ugagguaaac uuaaauccug a                                              21

<210> SEQ ID NO 326
<211> LENGTH: 21
<212> TYPE: DNA
<213> ORGANISM: homo sapiens

<400> SEQUENCE: 326
uucuggccaa ugaaggcgua g                                              21

<210> SEQ ID NO 327
<211> LENGTH: 21
<212> TYPE: DNA
<213> ORGANISM: homo sapiens

<400> SEQUENCE: 327
uuuaaguguc aauuuagugg c                                              21

<210> SEQ ID NO 328
<211> LENGTH: 21
<212> TYPE: DNA
<213> ORGANISM: homo sapiens

<400> SEQUENCE: 328
uagaacauag agugccaugg g                                              21

<210> SEQ ID NO 329
<211> LENGTH: 21
```

```
<212> TYPE: DNA
<213> ORGANISM: homo sapiens

<400> SEQUENCE: 329
aauuacuaag aucuucaccu t                                              21

<210> SEQ ID NO 330
<211> LENGTH: 21
<212> TYPE: DNA
<213> ORGANISM: homo sapiens

<400> SEQUENCE: 330
uaacauugga ugaguagacg g                                              21

<210> SEQ ID NO 331
<211> LENGTH: 21
<212> TYPE: DNA
<213> ORGANISM: homo sapiens

<400> SEQUENCE: 331
ucuuagaaca uagagugcca u                                              21

<210> SEQ ID NO 332
<211> LENGTH: 21
<212> TYPE: DNA
<213> ORGANISM: homo sapiens

<400> SEQUENCE: 332
uggcauuaag ucacauugcg g                                              21

<210> SEQ ID NO 333
<211> LENGTH: 21
<212> TYPE: DNA
<213> ORGANISM: homo sapiens

<400> SEQUENCE: 333
uagccuuggu uuaaucagcc u                                              21

<210> SEQ ID NO 334
<211> LENGTH: 21
<212> TYPE: DNA
<213> ORGANISM: homo sapiens

<400> SEQUENCE: 334
uucuuguggg ucaauuccua u                                              21

<210> SEQ ID NO 335
<211> LENGTH: 21
<212> TYPE: DNA
<213> ORGANISM: homo sapiens

<400> SEQUENCE: 335
uaucacuacu guuuaucugc a                                              21

<210> SEQ ID NO 336
<211> LENGTH: 21
<212> TYPE: DNA
<213> ORGANISM: homo sapiens

<400> SEQUENCE: 336
ucaggcugaa ggauacuucg u                                              21

<210> SEQ ID NO 337
<211> LENGTH: 21
```

```
<212> TYPE: DNA
<213> ORGANISM: homo sapiens

<400> SEQUENCE: 337
uguguuaauu cuaugucuga a                                              21

<210> SEQ ID NO 338
<211> LENGTH: 21
<212> TYPE: DNA
<213> ORGANISM: homo sapiens

<400> SEQUENCE: 338
uauuguugcc cauguccuca t                                              21

<210> SEQ ID NO 339
<211> LENGTH: 21
<212> TYPE: DNA
<213> ORGANISM: homo sapiens

<400> SEQUENCE: 339
uuguggguca auccuauaa g                                               21

<210> SEQ ID NO 340
<211> LENGTH: 21
<212> TYPE: DNA
<213> ORGANISM: homo sapiens

<400> SEQUENCE: 340
auuucuugug ggucaauucc t                                              21

<210> SEQ ID NO 341
<211> LENGTH: 21
<212> TYPE: DNA
<213> ORGANISM: homo sapiens

<400> SEQUENCE: 341
uguuauugga guggccaccg a                                              21

<210> SEQ ID NO 342
<211> LENGTH: 21
<212> TYPE: DNA
<213> ORGANISM: homo sapiens

<400> SEQUENCE: 342
ucuguaaauu uguucacuct c                                              21

<210> SEQ ID NO 343
<211> LENGTH: 21
<212> TYPE: DNA
<213> ORGANISM: homo sapiens

<400> SEQUENCE: 343
uugcgguaca acuaucacua c                                              21

<210> SEQ ID NO 344
<211> LENGTH: 21
<212> TYPE: DNA
<213> ORGANISM: homo sapiens

<400> SEQUENCE: 344
augaguagac gguccuucgg a                                              21

<210> SEQ ID NO 345
<211> LENGTH: 21
```

-continued

```
<212> TYPE: DNA
<213> ORGANISM: homo sapiens

<400> SEQUENCE: 345
uaauuacuaa gaucuucacc t                                              21

<210> SEQ ID NO 346
<211> LENGTH: 21
<212> TYPE: DNA
<213> ORGANISM: homo sapiens

<400> SEQUENCE: 346
ugaaacaacc uugacgauga a                                              21

<210> SEQ ID NO 347
<211> LENGTH: 21
<212> TYPE: DNA
<213> ORGANISM: homo sapiens

<400> SEQUENCE: 347
ugaucaagcc auguauagct a                                              21

<210> SEQ ID NO 348
<211> LENGTH: 21
<212> TYPE: DNA
<213> ORGANISM: homo sapiens

<400> SEQUENCE: 348
uguaauuacu aagaucuuca c                                              21

<210> SEQ ID NO 349
<211> LENGTH: 21
<212> TYPE: DNA
<213> ORGANISM: homo sapiens

<400> SEQUENCE: 349
ugaauuugac caaguagcgc t                                              21

<210> SEQ ID NO 350
<211> LENGTH: 21
<212> TYPE: DNA
<213> ORGANISM: homo sapiens

<400> SEQUENCE: 350
uacuucguua gguacauauc a                                              21

<210> SEQ ID NO 351
<211> LENGTH: 21
<212> TYPE: DNA
<213> ORGANISM: homo sapiens

<400> SEQUENCE: 351
uguaguaaca gucuuccuca a                                              21

<210> SEQ ID NO 352
<211> LENGTH: 21
<212> TYPE: DNA
<213> ORGANISM: homo sapiens

<400> SEQUENCE: 352
uggacgauaa ucuagcaaca g                                              21

<210> SEQ ID NO 353
<211> LENGTH: 21
```

```
<212> TYPE: DNA
<213> ORGANISM: homo sapiens

<400> SEQUENCE: 353
uauggcagaa uuggccauca t                                              21

<210> SEQ ID NO 354
<211> LENGTH: 21
<212> TYPE: DNA
<213> ORGANISM: homo sapiens

<400> SEQUENCE: 354
uuucaccugg aggacagggc t                                              21

<210> SEQ ID NO 355
<211> LENGTH: 21
<212> TYPE: DNA
<213> ORGANISM: homo sapiens

<400> SEQUENCE: 355
ucacuugggc auuaacacut t                                              21

<210> SEQ ID NO 356
<211> LENGTH: 21
<212> TYPE: DNA
<213> ORGANISM: homo sapiens

<400> SEQUENCE: 356
acuuccucuu ugcacuuggt g                                              21

<210> SEQ ID NO 357
<211> LENGTH: 21
<212> TYPE: DNA
<213> ORGANISM: homo sapiens

<400> SEQUENCE: 357
ugagugugca uuccuugaug a                                              21

<210> SEQ ID NO 358
<211> LENGTH: 21
<212> TYPE: DNA
<213> ORGANISM: homo sapiens

<400> SEQUENCE: 358
ucccuucuug gcagggcacg c                                              21

<210> SEQ ID NO 359
<211> LENGTH: 21
<212> TYPE: DNA
<213> ORGANISM: homo sapiens

<400> SEQUENCE: 359
gacugugcag ucccuagcut t                                              21

<210> SEQ ID NO 360
<211> LENGTH: 21
<212> TYPE: DNA
<213> ORGANISM: homo sapiens

<400> SEQUENCE: 360
aucaugaugc aggccuucca a                                              21

<210> SEQ ID NO 361
<211> LENGTH: 21
```

```
<212> TYPE: DNA
<213> ORGANISM: homo sapiens

<400> SEQUENCE: 361
uucugagucu caacuguagt a                                              21

<210> SEQ ID NO 362
<211> LENGTH: 21
<212> TYPE: DNA
<213> ORGANISM: homo sapiens

<400> SEQUENCE: 362
uaaucuagca acagacguaa g                                              21

<210> SEQ ID NO 363
<211> LENGTH: 21
<212> TYPE: DNA
<213> ORGANISM: homo sapiens

<400> SEQUENCE: 363
ucaacuguag uaacagucut c                                              21

<210> SEQ ID NO 364
<211> LENGTH: 21
<212> TYPE: DNA
<213> ORGANISM: homo sapiens

<400> SEQUENCE: 364
cucaacugua guaacaguct t                                              21

<210> SEQ ID NO 365
<211> LENGTH: 21
<212> TYPE: DNA
<213> ORGANISM: homo sapiens

<400> SEQUENCE: 365
agcaacagac guaagaacca g                                              21

<210> SEQ ID NO 366
<211> LENGTH: 21
<212> TYPE: DNA
<213> ORGANISM: homo sapiens

<400> SEQUENCE: 366
ucugagucuc aacuguagua a                                              21

<210> SEQ ID NO 367
<211> LENGTH: 21
<212> TYPE: DNA
<213> ORGANISM: homo sapiens

<400> SEQUENCE: 367
uuccuuucac cuggaggaca g                                              21

<210> SEQ ID NO 368
<211> LENGTH: 21
<212> TYPE: DNA
<213> ORGANISM: homo sapiens

<400> SEQUENCE: 368
uuggacgaua aucuagcaac a                                              21

<210> SEQ ID NO 369
<211> LENGTH: 21
```

```
<212> TYPE: DNA
<213> ORGANISM: homo sapiens

<400> SEQUENCE: 369
acuguaguaa cagucuuccu c                                              21

<210> SEQ ID NO 370
<211> LENGTH: 21
<212> TYPE: DNA
<213> ORGANISM: homo sapiens

<400> SEQUENCE: 370
ucaugaugca ggccuuccaa g                                              21

<210> SEQ ID NO 371
<211> LENGTH: 21
<212> TYPE: DNA
<213> ORGANISM: homo sapiens

<400> SEQUENCE: 371
ucaauuccaa ucccuuggag t                                              21

<210> SEQ ID NO 372
<211> LENGTH: 21
<212> TYPE: DNA
<213> ORGANISM: homo sapiens

<400> SEQUENCE: 372
gugcaguccc uagcuuucct t                                              21

<210> SEQ ID NO 373
<211> LENGTH: 21
<212> TYPE: DNA
<213> ORGANISM: homo sapiens

<400> SEQUENCE: 373
ccaaguucug agucucaact g                                              21

<210> SEQ ID NO 374
<211> LENGTH: 21
<212> TYPE: DNA
<213> ORGANISM: homo sapiens

<400> SEQUENCE: 374
gauaaucuag caacagacgt a                                              21

<210> SEQ ID NO 375
<211> LENGTH: 21
<212> TYPE: DNA
<213> ORGANISM: homo sapiens

<400> SEQUENCE: 375
uuauggcaga auuggccauc a                                              21

<210> SEQ ID NO 376
<211> LENGTH: 21
<212> TYPE: DNA
<213> ORGANISM: homo sapiens

<400> SEQUENCE: 376
caaguucuga gucucaacug t                                              21

<210> SEQ ID NO 377
<211> LENGTH: 21
```

-continued

```
<212> TYPE: DNA
<213> ORGANISM: homo sapiens

<400> SEQUENCE: 377
ugugcagucc cuagcuuucc t                                              21

<210> SEQ ID NO 378
<211> LENGTH: 21
<212> TYPE: DNA
<213> ORGANISM: homo sapiens

<400> SEQUENCE: 378
ucccuuggag uugaugucag t                                              21

<210> SEQ ID NO 379
<211> LENGTH: 21
<212> TYPE: DNA
<213> ORGANISM: homo sapiens

<400> SEQUENCE: 379
auggcagaau uggccaucat g                                              21

<210> SEQ ID NO 380
<211> LENGTH: 21
<212> TYPE: DNA
<213> ORGANISM: homo sapiens

<400> SEQUENCE: 380
uggccaucau gaugcaggcc t                                              21

<210> SEQ ID NO 381
<211> LENGTH: 21
<212> TYPE: DNA
<213> ORGANISM: homo sapiens

<400> SEQUENCE: 381
gucacuuggg cauuaacact t                                              21

<210> SEQ ID NO 382
<211> LENGTH: 21
<212> TYPE: DNA
<213> ORGANISM: homo sapiens

<400> SEQUENCE: 382
gcuuauggca gaauuggcca t                                              21

<210> SEQ ID NO 383
<211> LENGTH: 21
<212> TYPE: DNA
<213> ORGANISM: homo sapiens

<400> SEQUENCE: 383
cgauaaucua gcaacagacg t                                              21

<210> SEQ ID NO 384
<211> LENGTH: 21
<212> TYPE: DNA
<213> ORGANISM: homo sapiens

<400> SEQUENCE: 384
ucucaacugu aguaacaguc t                                              21

<210> SEQ ID NO 385
<211> LENGTH: 21
```

```
<212> TYPE: DNA
<213> ORGANISM: homo sapiens

<400> SEQUENCE: 385
aucuagcaac agacguaaga a                                              21

<210> SEQ ID NO 386
<211> LENGTH: 21
<212> TYPE: DNA
<213> ORGANISM: homo sapiens

<400> SEQUENCE: 386
agucacuugg gcauuaacac t                                              21

<210> SEQ ID NO 387
<211> LENGTH: 21
<212> TYPE: DNA
<213> ORGANISM: homo sapiens

<400> SEQUENCE: 387
agggcuuaug gcagaauugg c                                              21

<210> SEQ ID NO 388
<211> LENGTH: 21
<212> TYPE: DNA
<213> ORGANISM: homo sapiens

<400> SEQUENCE: 388
ugagucucaa cuguaguaac a                                              21

<210> SEQ ID NO 389
<211> LENGTH: 21
<212> TYPE: DNA
<213> ORGANISM: homo sapiens

<400> SEQUENCE: 389
aguucugagu cucaacugua g                                              21

<210> SEQ ID NO 390
<211> LENGTH: 21
<212> TYPE: DNA
<213> ORGANISM: homo sapiens

<400> SEQUENCE: 390
uuuggacgau aaucuagcaa c                                              21

<210> SEQ ID NO 391
<211> LENGTH: 21
<212> TYPE: DNA
<213> ORGANISM: homo sapiens

<400> SEQUENCE: 391
ccucaauucc aacccuugg a                                               21

<210> SEQ ID NO 392
<211> LENGTH: 21
<212> TYPE: DNA
<213> ORGANISM: homo sapiens

<400> SEQUENCE: 392
uggcagaauu ggccaucaug a                                              21

<210> SEQ ID NO 393
<211> LENGTH: 21
```

```
<212> TYPE: DNA
<213> ORGANISM: homo sapiens

<400> SEQUENCE: 393
cuguaguaac agucuuccuc a                                              21

<210> SEQ ID NO 394
<211> LENGTH: 21
<212> TYPE: DNA
<213> ORGANISM: homo sapiens

<400> SEQUENCE: 394
ucuagcaaca gacguaagaa c                                              21

<210> SEQ ID NO 395
<211> LENGTH: 21
<212> TYPE: DNA
<213> ORGANISM: homo sapiens

<400> SEQUENCE: 395
acgauaaucu agcaacagac g                                              21

<210> SEQ ID NO 396
<211> LENGTH: 21
<212> TYPE: DNA
<213> ORGANISM: homo sapiens

<400> SEQUENCE: 396
agucucaacu guaguaacag t                                              21

<210> SEQ ID NO 397
<211> LENGTH: 21
<212> TYPE: DNA
<213> ORGANISM: homo sapiens

<400> SEQUENCE: 397
acagggcuua uggcagaaut g                                              21

<210> SEQ ID NO 398
<211> LENGTH: 21
<212> TYPE: DNA
<213> ORGANISM: homo sapiens

<400> SEQUENCE: 398
aaucuagcaa cagacguaag a                                              21

<210> SEQ ID NO 399
<211> LENGTH: 21
<212> TYPE: DNA
<213> ORGANISM: homo sapiens

<400> SEQUENCE: 399
cuuauggcag aauuggccat c                                              21

<210> SEQ ID NO 400
<211> LENGTH: 21
<212> TYPE: DNA
<213> ORGANISM: homo sapiens

<400> SEQUENCE: 400
agggcacgca gucugguuca t                                              21

<210> SEQ ID NO 401
<211> LENGTH: 21
```

```
<212> TYPE: DNA
<213> ORGANISM: homo sapiens

<400> SEQUENCE: 401
uuugucaccu augacaccca g                                              21

<210> SEQ ID NO 402
<211> LENGTH: 21
<212> TYPE: DNA
<213> ORGANISM: homo sapiens

<400> SEQUENCE: 402
uuauagagca agccugguct g                                              21

<210> SEQ ID NO 403
<211> LENGTH: 21
<212> TYPE: DNA
<213> ORGANISM: homo sapiens

<400> SEQUENCE: 403
ucugauugug guaucuucct g                                              21

<210> SEQ ID NO 404
<211> LENGTH: 21
<212> TYPE: DNA
<213> ORGANISM: homo sapiens

<400> SEQUENCE: 404
uauuucagga caauuaugcc a                                              21

<210> SEQ ID NO 405
<211> LENGTH: 21
<212> TYPE: DNA
<213> ORGANISM: homo sapiens

<400> SEQUENCE: 405
uuaauguagu auuuccucca c                                              21

<210> SEQ ID NO 406
<211> LENGTH: 21
<212> TYPE: DNA
<213> ORGANISM: homo sapiens

<400> SEQUENCE: 406
uuucccaucg uuaccugcgg t                                              21

<210> SEQ ID NO 407
<211> LENGTH: 21
<212> TYPE: DNA
<213> ORGANISM: homo sapiens

<400> SEQUENCE: 407
uaguucaguu ggaucauccc a                                              21

<210> SEQ ID NO 408
<211> LENGTH: 21
<212> TYPE: DNA
<213> ORGANISM: homo sapiens

<400> SEQUENCE: 408
uugccuucug acacuaagca a                                              21

<210> SEQ ID NO 409
<211> LENGTH: 21
```

```
<212> TYPE: DNA
<213> ORGANISM: homo sapiens

<400> SEQUENCE: 409
uuauagggug ugccgccuct g                                              21

<210> SEQ ID NO 410
<211> LENGTH: 21
<212> TYPE: DNA
<213> ORGANISM: homo sapiens

<400> SEQUENCE: 410
uuuccaucug aaauauagga t                                              21

<210> SEQ ID NO 411
<211> LENGTH: 21
<212> TYPE: DNA
<213> ORGANISM: homo sapiens

<400> SEQUENCE: 411
uugcgcacca gcuucagucc g                                              21

<210> SEQ ID NO 412
<211> LENGTH: 21
<212> TYPE: DNA
<213> ORGANISM: homo sapiens

<400> SEQUENCE: 412
uugauguaga aaucagggut g                                              21

<210> SEQ ID NO 413
<211> LENGTH: 21
<212> TYPE: DNA
<213> ORGANISM: homo sapiens

<400> SEQUENCE: 413
uucucagcaa uagaacacca g                                              21

<210> SEQ ID NO 414
<211> LENGTH: 21
<212> TYPE: DNA
<213> ORGANISM: homo sapiens

<400> SEQUENCE: 414
uaaggcuucu uauaggucga a                                              21

<210> SEQ ID NO 415
<211> LENGTH: 21
<212> TYPE: DNA
<213> ORGANISM: homo sapiens

<400> SEQUENCE: 415
ucaaagaucc auucgccgcg g                                              21

<210> SEQ ID NO 416
<211> LENGTH: 21
<212> TYPE: DNA
<213> ORGANISM: homo sapiens

<400> SEQUENCE: 416
uugaugaggu agugcuccgg g                                              21

<210> SEQ ID NO 417
<211> LENGTH: 21
```

```
<212> TYPE: DNA
<213> ORGANISM: homo sapiens

<400> SEQUENCE: 417
uuuaugacgc ucauccgcug a                                              21

<210> SEQ ID NO 418
<211> LENGTH: 21
<212> TYPE: DNA
<213> ORGANISM: homo sapiens

<400> SEQUENCE: 418
uauuuguagg acacguugga a                                              21

<210> SEQ ID NO 419
<211> LENGTH: 21
<212> TYPE: DNA
<213> ORGANISM: homo sapiens

<400> SEQUENCE: 419
uacccugccg agguucacgg g                                              21

<210> SEQ ID NO 420
<211> LENGTH: 21
<212> TYPE: DNA
<213> ORGANISM: homo sapiens

<400> SEQUENCE: 420
uaucugagca cacucaaacg t                                              21

<210> SEQ ID NO 421
<211> LENGTH: 21
<212> TYPE: DNA
<213> ORGANISM: homo sapiens

<400> SEQUENCE: 421
ucuuuguaca ggucaauuct a                                              21

<210> SEQ ID NO 422
<211> LENGTH: 21
<212> TYPE: DNA
<213> ORGANISM: homo sapiens

<400> SEQUENCE: 422
uuugacuuga gagguaucgc t                                              21

<210> SEQ ID NO 423
<211> LENGTH: 21
<212> TYPE: DNA
<213> ORGANISM: homo sapiens

<400> SEQUENCE: 423
uuguguuucu ggacgaauut g                                              21

<210> SEQ ID NO 424
<211> LENGTH: 21
<212> TYPE: DNA
<213> ORGANISM: homo sapiens

<400> SEQUENCE: 424
uagagcuucc auuccucacg g                                              21

<210> SEQ ID NO 425
<211> LENGTH: 21
```

<210> SEQ ID NO 425
<211> LENGTH: 21
<212> TYPE: DNA
<213> ORGANISM: homo sapiens

<400> SEQUENCE: 425
uucacuuggc ucucgcugca g    21

<210> SEQ ID NO 426
<211> LENGTH: 21
<212> TYPE: DNA
<213> ORGANISM: homo sapiens

<400> SEQUENCE: 426
uacccggccg auaucuaugg g    21

<210> SEQ ID NO 427
<211> LENGTH: 21
<212> TYPE: DNA
<213> ORGANISM: homo sapiens

<400> SEQUENCE: 427
uucucaauuc cgacuggcct t    21

<210> SEQ ID NO 428
<211> LENGTH: 21
<212> TYPE: DNA
<213> ORGANISM: homo sapiens

<400> SEQUENCE: 428
uauuacagua aaguugauug a    21

<210> SEQ ID NO 429
<211> LENGTH: 21
<212> TYPE: DNA
<213> ORGANISM: homo sapiens

<400> SEQUENCE: 429
uuaacacagg cguauuccgt g    21

<210> SEQ ID NO 430
<211> LENGTH: 21
<212> TYPE: DNA
<213> ORGANISM: homo sapiens

<400> SEQUENCE: 430
aaaugugcuc uguacgccca g    21

<210> SEQ ID NO 431
<211> LENGTH: 21
<212> TYPE: DNA
<213> ORGANISM: homo sapiens

<400> SEQUENCE: 431
uaguugaaau gcuuguccgc t    21

<210> SEQ ID NO 432
<211> LENGTH: 21
<212> TYPE: DNA
<213> ORGANISM: homo sapiens

<400> SEQUENCE: 432
uuggcuccag agcacgccgg g    21

<210> SEQ ID NO 433
<211> LENGTH: 21

```
<212> TYPE: DNA
<213> ORGANISM: homo sapiens

<400> SEQUENCE: 433
uucucugaca ccucaacucc a                                              21

<210> SEQ ID NO 434
<211> LENGTH: 21
<212> TYPE: DNA
<213> ORGANISM: homo sapiens

<400> SEQUENCE: 434
uaaggagcuc agaucaaaca g                                              21

<210> SEQ ID NO 435
<211> LENGTH: 21
<212> TYPE: DNA
<213> ORGANISM: homo sapiens

<400> SEQUENCE: 435
ugaacauuca gucagaucga a                                              21

<210> SEQ ID NO 436
<211> LENGTH: 21
<212> TYPE: DNA
<213> ORGANISM: homo sapiens

<400> SEQUENCE: 436
uauaguacga gacuccguug t                                              21

<210> SEQ ID NO 437
<211> LENGTH: 21
<212> TYPE: DNA
<213> ORGANISM: homo sapiens

<400> SEQUENCE: 437
augaauagag aaguguccgg a                                              21

<210> SEQ ID NO 438
<211> LENGTH: 21
<212> TYPE: DNA
<213> ORGANISM: homo sapiens

<400> SEQUENCE: 438
auaagcacag uaaagguggt a                                              21

<210> SEQ ID NO 439
<211> LENGTH: 21
<212> TYPE: DNA
<213> ORGANISM: homo sapiens

<400> SEQUENCE: 439
uuaacagcuu aggcguuccc a                                              21

<210> SEQ ID NO 440
<211> LENGTH: 21
<212> TYPE: DNA
<213> ORGANISM: homo sapiens

<400> SEQUENCE: 440
uuccuuuccc aucguuacct g                                              21

<210> SEQ ID NO 441
<211> LENGTH: 21
```

```
<212> TYPE: DNA
<213> ORGANISM: homo sapiens

<400> SEQUENCE: 441
auugauguag aaaucagggt t                                        21

<210> SEQ ID NO 442
<211> LENGTH: 21
<212> TYPE: DNA
<213> ORGANISM: homo sapiens

<400> SEQUENCE: 442
auguaguauu uccuccacgt g                                        21

<210> SEQ ID NO 443
<211> LENGTH: 21
<212> TYPE: DNA
<213> ORGANISM: homo sapiens

<400> SEQUENCE: 443
uuaaggcuuc uuauaggucg a                                        21

<210> SEQ ID NO 444
<211> LENGTH: 21
<212> TYPE: DNA
<213> ORGANISM: homo sapiens

<400> SEQUENCE: 444
auugaugagg uagugcuccg g                                        21

<210> SEQ ID NO 445
<211> LENGTH: 21
<212> TYPE: DNA
<213> ORGANISM: homo sapiens

<400> SEQUENCE: 445
aaauauagga ugaaccuccg c                                        21

<210> SEQ ID NO 446
<211> LENGTH: 21
<212> TYPE: DNA
<213> ORGANISM: homo sapiens

<400> SEQUENCE: 446
uauaggauga accuccgcuc t                                        21

<210> SEQ ID NO 447
<211> LENGTH: 21
<212> TYPE: DNA
<213> ORGANISM: homo sapiens

<400> SEQUENCE: 447
uugaguauuu guaggacacg t                                        21

<210> SEQ ID NO 448
<211> LENGTH: 21
<212> TYPE: DNA
<213> ORGANISM: homo sapiens

<400> SEQUENCE: 448
uuguaggaca cguuggaact t                                        21

<210> SEQ ID NO 449
<211> LENGTH: 21
```

```
<212> TYPE: DNA
<213> ORGANISM: homo sapiens

<400> SEQUENCE: 449
aucccuuaua gagcaagcct g                                              21

<210> SEQ ID NO 450
<211> LENGTH: 21
<212> TYPE: DNA
<213> ORGANISM: homo sapiens

<400> SEQUENCE: 450
ucaaacguga uccuggugga g                                              21

<210> SEQ ID NO 451
<211> LENGTH: 21
<212> TYPE: DNA
<213> ORGANISM: homo sapiens

<400> SEQUENCE: 451
caguuaacaa guucuuauat t                                              21

<210> SEQ ID NO 452
<211> LENGTH: 21
<212> TYPE: DNA
<213> ORGANISM: homo sapiens

<400> SEQUENCE: 452
gcaggugcuu gaaaccguat t                                              21

<210> SEQ ID NO 453
<211> LENGTH: 21
<212> TYPE: DNA
<213> ORGANISM: homo sapiens

<400> SEQUENCE: 453
caaucuugcu gagcauaaat t                                              21

<210> SEQ ID NO 454
<211> LENGTH: 21
<212> TYPE: DNA
<213> ORGANISM: homo sapiens

<400> SEQUENCE: 454
ccggcuuuca ggaagauaat t                                              21

<210> SEQ ID NO 455
<211> LENGTH: 21
<212> TYPE: DNA
<213> ORGANISM: homo sapiens

<400> SEQUENCE: 455
cgcauauggu aucccucaat t                                              21

<210> SEQ ID NO 456
<211> LENGTH: 21
<212> TYPE: DNA
<213> ORGANISM: homo sapiens

<400> SEQUENCE: 456
gcuacucguu aauuaucaat t                                              21

<210> SEQ ID NO 457
<211> LENGTH: 21
```

```
<212> TYPE: DNA
<213> ORGANISM: homo sapiens

<400> SEQUENCE: 457
ccggaaguug uaugguuaat t                                              21

<210> SEQ ID NO 458
<211> LENGTH: 21
<212> TYPE: DNA
<213> ORGANISM: homo sapiens

<400> SEQUENCE: 458
gccggguuac gucaccuaat t                                              21

<210> SEQ ID NO 459
<211> LENGTH: 21
<212> TYPE: DNA
<213> ORGANISM: homo sapiens

<400> SEQUENCE: 459
ccaacuaccu caagagcaat t                                              21

<210> SEQ ID NO 460
<211> LENGTH: 21
<212> TYPE: DNA
<213> ORGANISM: homo sapiens

<400> SEQUENCE: 460
ggcauuugua uaagacaaat t                                              21

<210> SEQ ID NO 461
<211> LENGTH: 21
<212> TYPE: DNA
<213> ORGANISM: homo sapiens

<400> SEQUENCE: 461
cugccacucu aauugucaat t                                              21

<210> SEQ ID NO 462
<211> LENGTH: 21
<212> TYPE: DNA
<213> ORGANISM: homo sapiens

<400> SEQUENCE: 462
gacuaccuau caauuauaat t                                              21

<210> SEQ ID NO 463
<211> LENGTH: 21
<212> TYPE: DNA
<213> ORGANISM: homo sapiens

<400> SEQUENCE: 463
aguggguuua cauacucaat t                                              21

<210> SEQ ID NO 464
<211> LENGTH: 21
<212> TYPE: DNA
<213> ORGANISM: homo sapiens

<400> SEQUENCE: 464
ggagcccauc acuauggaat t                                              21

<210> SEQ ID NO 465
<211> LENGTH: 21
```

```
<212> TYPE: DNA
<213> ORGANISM: homo sapiens

<400> SEQUENCE: 465
gcggacaguu aauaacagat t                                              21

<210> SEQ ID NO 466
<211> LENGTH: 21
<212> TYPE: DNA
<213> ORGANISM: homo sapiens

<400> SEQUENCE: 466
gguaaagacu acaucccaat t                                              21

<210> SEQ ID NO 467
<211> LENGTH: 21
<212> TYPE: DNA
<213> ORGANISM: homo sapiens

<400> SEQUENCE: 467
ggagcugauc acucuaacat t                                              21

<210> SEQ ID NO 468
<211> LENGTH: 21
<212> TYPE: DNA
<213> ORGANISM: homo sapiens

<400> SEQUENCE: 468 cuuugaucccc ugauggaaat t                                             21

<210> SEQ ID NO 469
<211> LENGTH: 21
<212> TYPE: DNA
<213> ORGANISM: homo sapiens

<400> SEQUENCE: 469
cuugaacacg agaguucaat t                                              21

<210> SEQ ID NO 470
<211> LENGTH: 21
<212> TYPE: DNA
<213> ORGANISM: homo sapiens

<400> SEQUENCE: 470
ggaaccucgg acaagucuat t                                              21

<210> SEQ ID NO 471
<211> LENGTH: 21
<212> TYPE: DNA
<213> ORGANISM: homo sapiens

<400> SEQUENCE: 471
gccauacucu uguccucaat t                                              21

<210> SEQ ID NO 472
<211> LENGTH: 21
<212> TYPE: DNA
<213> ORGANISM: homo sapiens

<400> SEQUENCE: 472
acuugagagu aaccaguaat t                                              21

<210> SEQ ID NO 473
<211> LENGTH: 21
```

```
<212> TYPE: DNA
<213> ORGANISM: homo sapiens

<400> SEQUENCE: 473
cgaccacgcu gagcuggaat t                                              21

<210> SEQ ID NO 474
<211> LENGTH: 21
<212> TYPE: DNA
<213> ORGANISM: homo sapiens

<400> SEQUENCE: 474
ccauaaucau uccgaagcat t                                              21

<210> SEQ ID NO 475
<211> LENGTH: 21
<212> TYPE: DNA
<213> ORGANISM: homo sapiens

<400> SEQUENCE: 475
ccugugaagc aacagucaat t                                              21

<210> SEQ ID NO 476
<211> LENGTH: 21
<212> TYPE: DNA
<213> ORGANISM: homo sapiens

<400> SEQUENCE: 476
caggaguaca aauggaugat t                                              21

<210> SEQ ID NO 477
<211> LENGTH: 21
<212> TYPE: DNA
<213> ORGANISM: homo sapiens

<400> SEQUENCE: 477
ggaacaaggc aagaaaccat t                                              21

<210> SEQ ID NO 478
<211> LENGTH: 21
<212> TYPE: DNA
<213> ORGANISM: homo sapiens

<400> SEQUENCE: 478
cacuacacau ggagccuaat t                                              21

<210> SEQ ID NO 479
<211> LENGTH: 21
<212> TYPE: DNA
<213> ORGANISM: homo sapiens

<400> SEQUENCE: 479
gguuguggcu gacucuagat t                                              21

<210> SEQ ID NO 480
<211> LENGTH: 21
<212> TYPE: DNA
<213> ORGANISM: homo sapiens

<400> SEQUENCE: 480
cguggcuacu cguuaauuat t                                              21

<210> SEQ ID NO 481
<211> LENGTH: 21
```

```
<212> TYPE: DNA
<213> ORGANISM: homo sapiens

<400> SEQUENCE: 481
gccggaaguu guaugguuat t                                              21

<210> SEQ ID NO 482
<211> LENGTH: 21
<212> TYPE: DNA
<213> ORGANISM: homo sapiens

<400> SEQUENCE: 482
cucuaauugu caaugugaat t                                              21

<210> SEQ ID NO 483
<211> LENGTH: 21
<212> TYPE: DNA
<213> ORGANISM: homo sapiens

<400> SEQUENCE: 483
ggaaauagug gguuuacaut t                                              21

<210> SEQ ID NO 484
<211> LENGTH: 21
<212> TYPE: DNA
<213> ORGANISM: homo sapiens

<400> SEQUENCE: 484
ggacguaacu gaagaggaut t                                              21

<210> SEQ ID NO 485
<211> LENGTH: 21
<212> TYPE: DNA
<213> ORGANISM: homo sapiens

<400> SEQUENCE: 485
gaugcaggga auuauacaat t                                              21

<210> SEQ ID NO 486
<211> LENGTH: 21
<212> TYPE: DNA
<213> ORGANISM: homo sapiens

<400> SEQUENCE: 486
cggaaguugu augguuaaat t                                              21

<210> SEQ ID NO 487
<211> LENGTH: 21
<212> TYPE: DNA
<213> ORGANISM: homo sapiens

<400> SEQUENCE: 487
cagucaaugg gcauuuguat t                                              21

<210> SEQ ID NO 488
<211> LENGTH: 21
<212> TYPE: DNA
<213> ORGANISM: homo sapiens

<400> SEQUENCE: 488
ggguuacguc accuaacaut t                                              21

<210> SEQ ID NO 489
<211> LENGTH: 21
```

```
<212> TYPE: DNA
<213> ORGANISM: homo sapiens

<400> SEQUENCE: 489
caagagcaaa cgugacuuat t                                              21

<210> SEQ ID NO 490
<211> LENGTH: 21
<212> TYPE: DNA
<213> ORGANISM: homo sapiens

<400> SEQUENCE: 490
caacuaccuc aagagcaaat t                                              21

<210> SEQ ID NO 491
<211> LENGTH: 21
<212> TYPE: DNA
<213> ORGANISM: homo sapiens

<400> SEQUENCE: 491
augccauacu gacaggaaat t                                              21

<210> SEQ ID NO 492
<211> LENGTH: 21
<212> TYPE: DNA
<213> ORGANISM: homo sapiens

<400> SEQUENCE: 492
agaacaaugc acuacaguat t                                              21

<210> SEQ ID NO 493
<211> LENGTH: 21
<212> TYPE: DNA
<213> ORGANISM: homo sapiens

<400> SEQUENCE: 493
guggcuacuc guuaauuaut t                                              21

<210> SEQ ID NO 494
<211> LENGTH: 21
<212> TYPE: DNA
<213> ORGANISM: homo sapiens

<400> SEQUENCE: 494
gguaucccuc aaccuacaat t                                              21

<210> SEQ ID NO 495
<211> LENGTH: 21
<212> TYPE: DNA
<213> ORGANISM: homo sapiens

<400> SEQUENCE: 495
agcauaccuc acuguucaat t                                              21

<210> SEQ ID NO 496
<211> LENGTH: 21
<212> TYPE: DNA
<213> ORGANISM: homo sapiens

<400> SEQUENCE: 496
uguacaacag gaugguaaat t                                              21

<210> SEQ ID NO 497
<211> LENGTH: 21
```

-continued

```
<212> TYPE: DNA
<213> ORGANISM: homo sapiens

<400> SEQUENCE: 497
ucuaauuguc aaugugaaat t                                              21

<210> SEQ ID NO 498
<211> LENGTH: 21
<212> TYPE: DNA
<213> ORGANISM: homo sapiens

<400> SEQUENCE: 498
gaacaaugca cuacaguaut t                                              21

<210> SEQ ID NO 499
<211> LENGTH: 21
<212> TYPE: DNA
<213> ORGANISM: homo sapiens

<400> SEQUENCE: 499
caagauugac uugagaguat t                                              21

<210> SEQ ID NO 500
<211> LENGTH: 21
<212> TYPE: DNA
<213> ORGANISM: homo sapiens

<400> SEQUENCE: 500
gagcaaacgu gacuuauuut t                                              21

<210> SEQ ID NO 501
<211> LENGTH: 21
<212> TYPE: DNA
<213> ORGANISM: homo sapiens

<400> SEQUENCE: 501
gaaaguuacc agucuauuat t                                              21

<210> SEQ ID NO 502
<211> LENGTH: 21
<212> TYPE: DNA
<213> ORGANISM: homo sapiens

<400> SEQUENCE: 502
caaugugguc aaccuucuat t                                              21

<210> SEQ ID NO 503
<211> LENGTH: 21
<212> TYPE: DNA
<213> ORGANISM: homo sapiens

<400> SEQUENCE: 503
ccagcuacau gaucagcuat t                                              21

<210> SEQ ID NO 504
<211> LENGTH: 21
<212> TYPE: DNA
<213> ORGANISM: homo sapiens

<400> SEQUENCE: 504 gaauuccug ggacagcaat t                                               21

<210> SEQ ID NO 505
<211> LENGTH: 21
```

```
<212> TYPE: DNA
<213> ORGANISM: homo sapiens

<400> SEQUENCE: 505
agacgaacuu ggaaaucaut t                                              21

<210> SEQ ID NO 506
<211> LENGTH: 21
<212> TYPE: DNA
<213> ORGANISM: homo sapiens

<400> SEQUENCE: 506
cauggagucg uguacauuat t                                              21

<210> SEQ ID NO 507
<211> LENGTH: 21
<212> TYPE: DNA
<213> ORGANISM: homo sapiens

<400> SEQUENCE: 507
cgucauggau ccagaugaat t                                              21

<210> SEQ ID NO 508
<211> LENGTH: 21
<212> TYPE: DNA
<213> ORGANISM: homo sapiens

<400> SEQUENCE: 508
caggaaaccu ggagaaucat t                                              21

<210> SEQ ID NO 509
<211> LENGTH: 21
<212> TYPE: DNA
<213> ORGANISM: homo sapiens

<400> SEQUENCE: 509
cgcugacaug uacggucuat t                                              21

<210> SEQ ID NO 510
<211> LENGTH: 21
<212> TYPE: DNA
<213> ORGANISM: homo sapiens

<400> SEQUENCE: 510
ugauuauacu acaccagaat t                                              21

<210> SEQ ID NO 511
<211> LENGTH: 21
<212> TYPE: DNA
<213> ORGANISM: homo sapiens

<400> SEQUENCE: 511
gggaccuggc ggcacgaaat t                                              21

<210> SEQ ID NO 512
<211> LENGTH: 21
<212> TYPE: DNA
<213> ORGANISM: homo sapiens

<400> SEQUENCE: 512 cccaucccu ugugaagaat t                                               21

<210> SEQ ID NO 513
<211> LENGTH: 21
```

```
<212> TYPE: DNA
<213> ORGANISM: homo sapiens

<400> SEQUENCE: 513
gauacucuuu ggaaauugat t                                              21

<210> SEQ ID NO 514
<211> LENGTH: 21
<212> TYPE: DNA
<213> ORGANISM: homo sapiens

<400> SEQUENCE: 514
gucucaugga auugaacuat t                                              21

<210> SEQ ID NO 515
<211> LENGTH: 21
<212> TYPE: DNA
<213> ORGANISM: homo sapiens

<400> SEQUENCE: 515
cggcggugau ugccauguut t                                              21

<210> SEQ ID NO 516
<211> LENGTH: 21
<212> TYPE: DNA
<213> ORGANISM: homo sapiens

<400> SEQUENCE: 516
caggcauugu auugaaggat t                                              21

<210> SEQ ID NO 517
<211> LENGTH: 21
<212> TYPE: DNA
<213> ORGANISM: homo sapiens

<400> SEQUENCE: 517
ucagcauaag aaacuuguat t                                              21

<210> SEQ ID NO 518
<211> LENGTH: 21
<212> TYPE: DNA
<213> ORGANISM: homo sapiens

<400> SEQUENCE: 518
cauuguucuu ccgauaucat t                                              21

<210> SEQ ID NO 519
<211> LENGTH: 21
<212> TYPE: DNA
<213> ORGANISM: homo sapiens

<400> SEQUENCE: 519
cauguucucu aauagcacat t                                              21

<210> SEQ ID NO 520
<211> LENGTH: 21
<212> TYPE: DNA
<213> ORGANISM: homo sapiens

<400> SEQUENCE: 520
gucccucagu gauguagaat t                                              21

<210> SEQ ID NO 521
<211> LENGTH: 21
```

```
<212> TYPE: DNA
<213> ORGANISM: homo sapiens

<400> SEQUENCE: 521
agaucaugug guuuaaagat t                                              21

<210> SEQ ID NO 522
<211> LENGTH: 21
<212> TYPE: DNA
<213> ORGANISM: homo sapiens

<400> SEQUENCE: 522
cgugucacuu ugugcaagat t                                              21

<210> SEQ ID NO 523
<211> LENGTH: 21
<212> TYPE: DNA
<213> ORGANISM: homo sapiens

<400> SEQUENCE: 523
ggcuuuggcc caauaaucat t                                              21

<210> SEQ ID NO 524
<211> LENGTH: 21
<212> TYPE: DNA
<213> ORGANISM: homo sapiens

<400> SEQUENCE: 524
gugucagcuu uguacaaaut t                                              21

<210> SEQ ID NO 525
<211> LENGTH: 21
<212> TYPE: DNA
<213> ORGANISM: homo sapiens

<400> SEQUENCE: 525
gcuuggcccg ggauauuuat t                                              21

<210> SEQ ID NO 526
<211> LENGTH: 21
<212> TYPE: DNA
<213> ORGANISM: homo sapiens

<400> SEQUENCE: 526
gacggacagu gguaugguut t                                              21

<210> SEQ ID NO 527
<211> LENGTH: 21
<212> TYPE: DNA
<213> ORGANISM: homo sapiens

<400> SEQUENCE: 527
ggauaucacu ccgaugacat t                                              21

<210> SEQ ID NO 528
<211> LENGTH: 21
<212> TYPE: DNA
<213> ORGANISM: homo sapiens

<400> SEQUENCE: 528
gacagaucua cguuugagat t                                              21

<210> SEQ ID NO 529
<211> LENGTH: 21
```

<212> TYPE: DNA
<213> ORGANISM: homo sapiens

<400> SEQUENCE: 529
gcucuggauu uguggaggat t                                              21

<210> SEQ ID NO 530
<211> LENGTH: 21
<212> TYPE: DNA
<213> ORGANISM: homo sapiens

<400> SEQUENCE: 530
acuuggccuc ggucauuuat t                                              21

<210> SEQ ID NO 531
<211> LENGTH: 21
<212> TYPE: DNA
<213> ORGANISM: homo sapiens

<400> SEQUENCE: 531
cugcgaagua ccuugguuat t                                              21

<210> SEQ ID NO 532
<211> LENGTH: 21
<212> TYPE: DNA
<213> ORGANISM: homo sapiens

<400> SEQUENCE: 532
gccucugugg guuugccuat t                                              21

<210> SEQ ID NO 533
<211> LENGTH: 21
<212> TYPE: DNA
<213> ORGANISM: homo sapiens

<400> SEQUENCE: 533
cgacugccuu augaugccat t                                              21

<210> SEQ ID NO 534
<211> LENGTH: 21
<212> TYPE: DNA
<213> ORGANISM: homo sapiens

<400> SEQUENCE: 534
ccaguacggc accacucaat t                                              21

<210> SEQ ID NO 535
<211> LENGTH: 21
<212> TYPE: DNA
<213> ORGANISM: homo sapiens

<400> SEQUENCE: 535
cuuggauacu cuuuggaaat t                                              21

<210> SEQ ID NO 536
<211> LENGTH: 21
<212> TYPE: DNA
<213> ORGANISM: homo sapiens

<400> SEQUENCE: 536
cuggagaauc agacgacaat t                                              21

<210> SEQ ID NO 537
<211> LENGTH: 21

```
<212> TYPE: DNA
<213> ORGANISM: homo sapiens

<400> SEQUENCE: 537
ggcacgaaau aucccucuuat t                                              21

<210> SEQ ID NO 538
<211> LENGTH: 21
<212> TYPE: DNA
<213> ORGANISM: homo sapiens

<400> SEQUENCE: 538
ccagucuauu auguacauat t                                               21

<210> SEQ ID NO 539
<211> LENGTH: 21
<212> TYPE: DNA
<213> ORGANISM: homo sapiens

<400> SEQUENCE: 539
cagcauaaga aacuuguaat t                                               21

<210> SEQ ID NO 540
<211> LENGTH: 21
<212> TYPE: DNA
<213> ORGANISM: homo sapiens

<400> SEQUENCE: 540
acuuguaaac cgagaccuat t                                               21

<210> SEQ ID NO 541
<211> LENGTH: 21
<212> TYPE: DNA
<213> ORGANISM: homo sapiens

<400> SEQUENCE: 541
cuuguaaacc gagaccuaat t                                               21

<210> SEQ ID NO 542
<211> LENGTH: 21
<212> TYPE: DNA
<213> ORGANISM: homo sapiens

<400> SEQUENCE: 542
gaaauauccu cuuaucggat t                                               21

<210> SEQ ID NO 543
<211> LENGTH: 21
<212> TYPE: DNA
<213> ORGANISM: homo sapiens

<400> SEQUENCE: 543
agcauaagaa acuuguaaat t                                               21

<210> SEQ ID NO 544
<211> LENGTH: 21
<212> TYPE: DNA
<213> ORGANISM: homo sapiens

<400> SEQUENCE: 544
ggaaaccugg agaaucagat t                                               21

<210> SEQ ID NO 545
<211> LENGTH: 21
```

```
<212> TYPE: DNA
<213> ORGANISM: homo sapiens

<400> SEQUENCE: 545
acucaggcau uguauugaat t                                              21

<210> SEQ ID NO 546
<211> LENGTH: 21
<212> TYPE: DNA
<213> ORGANISM: homo sapiens

<400> SEQUENCE: 546
augugaagcg gucaacaaat t                                              21

<210> SEQ ID NO 547
<211> LENGTH: 21
<212> TYPE: DNA
<213> ORGANISM: homo sapiens

<400> SEQUENCE: 547
cagcuacaug aucagcuaut t                                              21

<210> SEQ ID NO 548
<211> LENGTH: 21
<212> TYPE: DNA
<213> ORGANISM: homo sapiens

<400> SEQUENCE: 548
gcggcuacca guccggauat t                                              21

<210> SEQ ID NO 549
<211> LENGTH: 21
<212> TYPE: DNA
<213> ORGANISM: homo sapiens

<400> SEQUENCE: 549
acucaaacgc ugacauguat t                                              21

<210> SEQ ID NO 550
<211> LENGTH: 21
<212> TYPE: DNA
<213> ORGANISM: homo sapiens

<400> SEQUENCE: 550
cuacauuguu cuuccgauat t                                              21

<210> SEQ ID NO 551
<211> LENGTH: 21
<212> TYPE: DNA
<213> ORGANISM: homo sapiens

<400> SEQUENCE: 551
cgcucuuggu caacaggaat t                                              21

<210> SEQ ID NO 552
<211> LENGTH: 21
<212> TYPE: DNA
<213> ORGANISM: homo sapiens

<400> SEQUENCE: 552
cgcugauguc ggagcucaat t                                              21

<210> SEQ ID NO 553
<211> LENGTH: 21
```

```
<212> TYPE: DNA
<213> ORGANISM: homo sapiens

<400> SEQUENCE: 553
gcuucaccau cgaauccaat t                                              21

<210> SEQ ID NO 554
<211> LENGTH: 21
<212> TYPE: DNA
<213> ORGANISM: homo sapiens

<400> SEQUENCE: 554
cgaggucauu gugcaugaat t                                              21

<210> SEQ ID NO 555
<211> LENGTH: 21
<212> TYPE: DNA
<213> ORGANISM: homo sapiens

<400> SEQUENCE: 555
gccgauuauu ccuugguaat t                                              21

<210> SEQ ID NO 556
<211> LENGTH: 21
<212> TYPE: DNA
<213> ORGANISM: homo sapiens

<400> SEQUENCE: 556
gcaucgugug guacaaagat t                                              21

<210> SEQ ID NO 557
<211> LENGTH: 21
<212> TYPE: DNA
<213> ORGANISM: homo sapiens

<400> SEQUENCE: 557
cgcuucugcu cgacugcaat t                                              21

<210> SEQ ID NO 558
<211> LENGTH: 21
<212> TYPE: DNA
<213> ORGANISM: homo sapiens

<400> SEQUENCE: 558
gcggcuucag guagcugaat t                                              21

<210> SEQ ID NO 559
<211> LENGTH: 21
<212> TYPE: DNA
<213> ORGANISM: homo sapiens

<400> SEQUENCE: 559
gcaucuucga caagguguat t                                              21

<210> SEQ ID NO 560
<211> LENGTH: 21
<212> TYPE: DNA
<213> ORGANISM: homo sapiens

<400> SEQUENCE: 560
cgcccgaguu ccagugguat t                                              21

<210> SEQ ID NO 561
<211> LENGTH: 21
```

```
<212> TYPE: DNA
<213> ORGANISM: homo sapiens

<400> SEQUENCE: 561
caggcagcua cgucugcuat t                                              21

<210> SEQ ID NO 562
<211> LENGTH: 21
<212> TYPE: DNA
<213> ORGANISM: homo sapiens

<400> SEQUENCE: 562
ccgcuuucgg cauccacaat t                                              21

<210> SEQ ID NO 563
<211> LENGTH: 21
<212> TYPE: DNA
<213> ORGANISM: homo sapiens

<400> SEQUENCE: 563
ggaaagaaua agacugugat t                                              21

<210> SEQ ID NO 564
<211> LENGTH: 21
<212> TYPE: DNA
<213> ORGANISM: homo sapiens

<400> SEQUENCE: 564
cgaccuugaa caucacggat t                                              21

<210> SEQ ID NO 565
<211> LENGTH: 21
<212> TYPE: DNA
<213> ORGANISM: homo sapiens

<400> SEQUENCE: 565
cgagcacgag ggccacuaut t                                              21

<210> SEQ ID NO 566
<211> LENGTH: 21
<212> TYPE: DNA
<213> ORGANISM: homo sapiens

<400> SEQUENCE: 566
cgcuggagau gcagugcuut t                                              21

<210> SEQ ID NO 567
<211> LENGTH: 21
<212> TYPE: DNA
<213> ORGANISM: homo sapiens

<400> SEQUENCE: 567
caggcaacga gcucuaugat t                                              21

<210> SEQ ID NO 568
<211> LENGTH: 21
<212> TYPE: DNA
<213> ORGANISM: homo sapiens

<400> SEQUENCE: 568
gcauggagau cgugauccut t                                              21

<210> SEQ ID NO 569
<211> LENGTH: 21
```

```
<212> TYPE: DNA
<213> ORGANISM: homo sapiens

<400> SEQUENCE: 569
cggcucacgc agaacuugat t                                              21

<210> SEQ ID NO 570
<211> LENGTH: 21
<212> TYPE: DNA
<213> ORGANISM: homo sapiens

<400> SEQUENCE: 570
gagcgacgcu cccaacagat t                                              21

<210> SEQ ID NO 571
<211> LENGTH: 21
<212> TYPE: DNA
<213> ORGANISM: homo sapiens

<400> SEQUENCE: 571
cagacaucaa gacgggcuat t                                              21

<210> SEQ ID NO 572
<211> LENGTH: 21
<212> TYPE: DNA
<213> ORGANISM: homo sapiens

<400> SEQUENCE: 572
gugguuccuc caggaugaat t                                              21

<210> SEQ ID NO 573
<211> LENGTH: 21
<212> TYPE: DNA
<213> ORGANISM: homo sapiens

<400> SEQUENCE: 573
ggcccuacug caagguguut t                                              21

<210> SEQ ID NO 574
<211> LENGTH: 21
<212> TYPE: DNA
<213> ORGANISM: homo sapiens

<400> SEQUENCE: 574
ggagggcggu gaccacgcat t                                              21

<210> SEQ ID NO 575
<211> LENGTH: 21
<212> TYPE: DNA
<213> ORGANISM: homo sapiens

<400> SEQUENCE: 575
gcgaauaccu guccuacgat t                                              21

<210> SEQ ID NO 576
<211> LENGTH: 21
<212> TYPE: DNA
<213> ORGANISM: homo sapiens

<400> SEQUENCE: 576
gcacgaccug ggcucguaut t                                              21

<210> SEQ ID NO 577
<211> LENGTH: 21
```

```
<212> TYPE: DNA
<213> ORGANISM: homo sapiens

<400> SEQUENCE: 577
agcagccauu caucaacaat t                                              21

<210> SEQ ID NO 578
<211> LENGTH: 21
<212> TYPE: DNA
<213> ORGANISM: homo sapiens

<400> SEQUENCE: 578
gccuugcccg ggacaucuat t                                              21

<210> SEQ ID NO 579
<211> LENGTH: 21
<212> TYPE: DNA
<213> ORGANISM: homo sapiens

<400> SEQUENCE: 579
gacccaaggg cugcgucaat t                                              21

<210> SEQ ID NO 580
<211> LENGTH: 21
<212> TYPE: DNA
<213> ORGANISM: homo sapiens

<400> SEQUENCE: 580
uggcggacuc caaccagaat t                                              21

<210> SEQ ID NO 581
<211> LENGTH: 21
<212> TYPE: DNA
<213> ORGANISM: homo sapiens

<400> SEQUENCE: 581
agaaguaccu gucggugcat t                                              21

<210> SEQ ID NO 582
<211> LENGTH: 21
<212> TYPE: DNA
<213> ORGANISM: homo sapiens

<400> SEQUENCE: 582
aguacaucaa ggcacgcaut t                                              21

<210> SEQ ID NO 583
<211> LENGTH: 21
<212> TYPE: DNA
<213> ORGANISM: homo sapiens

<400> SEQUENCE: 583
aagccgacag cuacaaguat t                                              21

<210> SEQ ID NO 584
<211> LENGTH: 21
<212> TYPE: DNA
<213> ORGANISM: homo sapiens

<400> SEQUENCE: 584
gagcccgcug accauggaat t                                              21

<210> SEQ ID NO 585
<211> LENGTH: 21
```

```
<212> TYPE: DNA
<213> ORGANISM: homo sapiens

<400> SEQUENCE: 585
cagcgucgag uggcucaaat t                                              21

<210> SEQ ID NO 586
<211> LENGTH: 21
<212> TYPE: DNA
<213> ORGANISM: homo sapiens

<400> SEQUENCE: 586
cgacggcuuc accaucgaat t                                              21

<210> SEQ ID NO 587
<211> LENGTH: 21
<212> TYPE: DNA
<213> ORGANISM: homo sapiens

<400> SEQUENCE: 587
cgccgauuau uccuugguat t                                              21

<210> SEQ ID NO 588
<211> LENGTH: 21
<212> TYPE: DNA
<213> ORGANISM: homo sapiens

<400> SEQUENCE: 588
ccgaggucau ugugcaugat t                                              21

<210> SEQ ID NO 589
<211> LENGTH: 21
<212> TYPE: DNA
<213> ORGANISM: homo sapiens

<400> SEQUENCE: 589
cugaaagcau cuucgacaat t                                              21

<210> SEQ ID NO 590
<211> LENGTH: 21
<212> TYPE: DNA
<213> ORGANISM: homo sapiens

<400> SEQUENCE: 590
ugguaauaug aguaauacat t                                              21

<210> SEQ ID NO 591
<211> LENGTH: 21
<212> TYPE: DNA
<213> ORGANISM: homo sapiens

<400> SEQUENCE: 591
gagcaggcau agacaagaat t                                              21

<210> SEQ ID NO 592
<211> LENGTH: 21
<212> TYPE: DNA
<213> ORGANISM: homo sapiens

<400> SEQUENCE: 592
cgauuauucc uugguaauat t                                              21

<210> SEQ ID NO 593
<211> LENGTH: 21
```

```
<212> TYPE: DNA
<213> ORGANISM: homo sapiens

<400> SEQUENCE: 593
cagcaucgug ugguacaaat t                                              21

<210> SEQ ID NO 594
<211> LENGTH: 21
<212> TYPE: DNA
<213> ORGANISM: homo sapiens

<400> SEQUENCE: 594
gggagagcac cgaggucaut t                                              21

<210> SEQ ID NO 595
<211> LENGTH: 21
<212> TYPE: DNA
<213> ORGANISM: homo sapiens

<400> SEQUENCE: 595
cggcccacgc agacaucaat t                                              21

<210> SEQ ID NO 596
<211> LENGTH: 21
<212> TYPE: DNA
<213> ORGANISM: homo sapiens

<400> SEQUENCE: 596
cccgaguucc agugguacat t                                              21

<210> SEQ ID NO 597
<211> LENGTH: 21
<212> TYPE: DNA
<213> ORGANISM: homo sapiens

<400> SEQUENCE: 597
gguacaugcc aacgacacat t                                              21

<210> SEQ ID NO 598
<211> LENGTH: 21
<212> TYPE: DNA
<213> ORGANISM: homo sapiens

<400> SEQUENCE: 598
cgacugcaag aacgugcaut t                                              21

<210> SEQ ID NO 599
<211> LENGTH: 21
<212> TYPE: DNA
<213> ORGANISM: homo sapiens

<400> SEQUENCE: 599
gagguacaug ccaacgacat t                                              21

<210> SEQ ID NO 600
<211> LENGTH: 21
<212> TYPE: DNA
<213> ORGANISM: homo sapiens

<400> SEQUENCE: 600
cgagcucuau gacauccagt t                                              21

<210> SEQ ID NO 601
<211> LENGTH: 21
```

-continued

```
<212> TYPE: DNA
<213> ORGANISM: homo sapiens

<400> SEQUENCE: 601
gggccagauu guaagcuuat t                                              21

<210> SEQ ID NO 602
<211> LENGTH: 21
<212> TYPE: DNA
<213> ORGANISM: homo sapiens

<400> SEQUENCE: 602
gcacguugau gugaagauat t                                              21

<210> SEQ ID NO 603
<211> LENGTH: 21
<212> TYPE: DNA
<213> ORGANISM: homo sapiens

<400> SEQUENCE: 603
gggagauaac gugaacauat t                                              21

<210> SEQ ID NO 604
<211> LENGTH: 21
<212> TYPE: DNA
<213> ORGANISM: homo sapiens

<400> SEQUENCE: 604
agauauuggu guccuuaaat t                                              21

<210> SEQ ID NO 605
<211> LENGTH: 21
<212> TYPE: DNA
<213> ORGANISM: homo sapiens

<400> SEQUENCE: 605
ggaaugacau caaauuucat t                                              21

<210> SEQ ID NO 606
<211> LENGTH: 21
<212> TYPE: DNA
<213> ORGANISM: homo sapiens

<400> SEQUENCE: 606
gccucuaacu uguaaacaat t                                              21

<210> SEQ ID NO 607
<211> LENGTH: 21
<212> TYPE: DNA
<213> ORGANISM: homo sapiens

<400> SEQUENCE: 607
gggucugcag ugcaaugaat t                                              21

<210> SEQ ID NO 608
<211> LENGTH: 21
<212> TYPE: DNA
<213> ORGANISM: homo sapiens

<400> SEQUENCE: 608
ugaaguaccu gauauucuat t                                              21

<210> SEQ ID NO 609
<211> LENGTH: 21
```

```
<212> TYPE: DNA
<213> ORGANISM: homo sapiens

<400> SEQUENCE: 609
ugaucauauu gcaauugaat t                                              21

<210> SEQ ID NO 610
<211> LENGTH: 21
<212> TYPE: DNA
<213> ORGANISM: homo sapiens

<400> SEQUENCE: 610
ggacaauauu ggauggcuat t                                              21

<210> SEQ ID NO 611
<211> LENGTH: 21
<212> TYPE: DNA
<213> ORGANISM: homo sapiens

<400> SEQUENCE: 611
gccagaucau auagaaguat t                                              21

<210> SEQ ID NO 612
<211> LENGTH: 21
<212> TYPE: DNA
<213> ORGANISM: homo sapiens

<400> SEQUENCE: 612
cagcccugcu gauaccaaat t                                              21

<210> SEQ ID NO 613
<211> LENGTH: 21
<212> TYPE: DNA
<213> ORGANISM: homo sapiens

<400> SEQUENCE: 613
caaugacccu gauaguacat t                                              21

<210> SEQ ID NO 614
<211> LENGTH: 21
<212> TYPE: DNA
<213> ORGANISM: homo sapiens

<400> SEQUENCE: 614
gaaugggcug aaaucagaat t                                              21

<210> SEQ ID NO 615
<211> LENGTH: 21
<212> TYPE: DNA
<213> ORGANISM: homo sapiens

<400> SEQUENCE: 615
caugaagaug cgucaacaat t                                              21

<210> SEQ ID NO 616
<211> LENGTH: 21
<212> TYPE: DNA
<213> ORGANISM: homo sapiens

<400> SEQUENCE: 616
ccuuuauguu gaaugcuaut t                                              21

<210> SEQ ID NO 617
<211> LENGTH: 21
```

```
<212> TYPE: DNA
<213> ORGANISM: homo sapiens

<400> SEQUENCE: 617
gcuaauggaa agucacaaat t                                              21

<210> SEQ ID NO 618
<211> LENGTH: 21
<212> TYPE: DNA
<213> ORGANISM: homo sapiens

<400> SEQUENCE: 618
gccagucccg uuucauuuat t                                              21

<210> SEQ ID NO 619
<211> LENGTH: 21
<212> TYPE: DNA
<213> ORGANISM: homo sapiens

<400> SEQUENCE: 619
ggcgugagua caauuaguat t                                              21

<210> SEQ ID NO 620
<211> LENGTH: 21
<212> TYPE: DNA
<213> ORGANISM: homo sapiens

<400> SEQUENCE: 620
ggcuuggcaa cauauucaat t                                              21

<210> SEQ ID NO 621
<211> LENGTH: 21
<212> TYPE: DNA
<213> ORGANISM: homo sapiens

<400> SEQUENCE: 621
gugguuucau augcaauaat t                                              21

<210> SEQ ID NO 622
<211> LENGTH: 21
<212> TYPE: DNA
<213> ORGANISM: homo sapiens

<400> SEQUENCE: 622
acgugaauac cacgcuuuat t                                              21

<210> SEQ ID NO 623
<211> LENGTH: 21
<212> TYPE: DNA
<213> ORGANISM: homo sapiens

<400> SEQUENCE: 623
gggacuuuga agccuuaaut t                                              21

<210> SEQ ID NO 624
<211> LENGTH: 21
<212> TYPE: DNA
<213> ORGANISM: homo sapiens

<400> SEQUENCE: 624
cgggaugacu ugugcagaat t                                              21

<210> SEQ ID NO 625
<211> LENGTH: 21
```

```
<212> TYPE: DNA
<213> ORGANISM: homo sapiens

<400> SEQUENCE: 625
acccagaucc uacaauuuat t                                              21

<210> SEQ ID NO 626
<211> LENGTH: 21
<212> TYPE: DNA
<213> ORGANISM: homo sapiens

<400> SEQUENCE: 626
agauuguuac acucaacuat t                                              21

<210> SEQ ID NO 627
<211> LENGTH: 21
<212> TYPE: DNA
<213> ORGANISM: homo sapiens

<400> SEQUENCE: 627
augggagauu guuagcuuat t                                              21

<210> SEQ ID NO 628
<211> LENGTH: 21
<212> TYPE: DNA
<213> ORGANISM: homo sapiens

<400> SEQUENCE: 628
acaucagcuc ugagccuuat t                                              21

<210> SEQ ID NO 629
<211> LENGTH: 21
<212> TYPE: DNA
<213> ORGANISM: homo sapiens

<400> SEQUENCE: 629
cgugauugac acuggacaut t                                              21

<210> SEQ ID NO 630
<211> LENGTH: 21
<212> TYPE: DNA
<213> ORGANISM: homo sapiens

<400> SEQUENCE: 630
gaagcggccu aggacagaat t                                              21

<210> SEQ ID NO 631
<211> LENGTH: 21
<212> TYPE: DNA
<213> ORGANISM: homo sapiens

<400> SEQUENCE: 631
ugacuucggu gcuacuuaat t                                              21

<210> SEQ ID NO 632
<211> LENGTH: 21
<212> TYPE: DNA
<213> ORGANISM: homo sapiens

<400> SEQUENCE: 632
caucaagaag gauggguuat t                                              21

<210> SEQ ID NO 633
<211> LENGTH: 21
```

```
<212> TYPE: DNA
<213> ORGANISM: homo sapiens

<400> SEQUENCE: 633
aauuugaccu ggcaaccaat t                                              21

<210> SEQ ID NO 634
<211> LENGTH: 21
<212> TYPE: DNA
<213> ORGANISM: homo sapiens

<400> SEQUENCE: 634
ccuuucccau ccuaaucuat t                                              21

<210> SEQ ID NO 635
<211> LENGTH: 21
<212> TYPE: DNA
<213> ORGANISM: homo sapiens

<400> SEQUENCE: 635
agggcuacag acuggagaat t                                              21

<210> SEQ ID NO 636
<211> LENGTH: 21
<212> TYPE: DNA
<213> ORGANISM: homo sapiens

<400> SEQUENCE: 636
gaaugacauc aaauuucaat t                                              21

<210> SEQ ID NO 637
<211> LENGTH: 21
<212> TYPE: DNA
<213> ORGANISM: homo sapiens

<400> SEQUENCE: 637
cagauauugg uguccuuaat t                                              21

<210> SEQ ID NO 638
<211> LENGTH: 21
<212> TYPE: DNA
<213> ORGANISM: homo sapiens

<400> SEQUENCE: 638
cgugaacaua ucuuucaaat t                                              21

<210> SEQ ID NO 639
<211> LENGTH: 21
<212> TYPE: DNA
<213> ORGANISM: homo sapiens

<400> SEQUENCE: 639
cagaucauau agaaguaaat t                                              21

<210> SEQ ID NO 640
<211> LENGTH: 21
<212> TYPE: DNA
<213> ORGANISM: homo sapiens

<400> SEQUENCE: 640
cacguugaug ugaagauaat t                                              21

<210> SEQ ID NO 641
<211> LENGTH: 21
```

```
<212> TYPE: DNA
<213> ORGANISM: homo sapiens

<400> SEQUENCE: 641
cgaugcuaau ggaaagucat t                                              21

<210> SEQ ID NO 642
<211> LENGTH: 21
<212> TYPE: DNA
<213> ORGANISM: homo sapiens

<400> SEQUENCE: 642
ggaaggcgug aguacaauut t                                              21

<210> SEQ ID NO 643
<211> LENGTH: 21
<212> TYPE: DNA
<213> ORGANISM: homo sapiens

<400> SEQUENCE: 643
gcgugaguac aauuaguaut t                                              21

<210> SEQ ID NO 644
<211> LENGTH: 21
<212> TYPE: DNA
<213> ORGANISM: homo sapiens

<400> SEQUENCE: 644
acguugaugu gaagauaaat t                                              21

<210> SEQ ID NO 645
<211> LENGTH: 21
<212> TYPE: DNA
<213> ORGANISM: homo sapiens

<400> SEQUENCE: 645
cgugaguaca auuaguauat t                                              21

<210> SEQ ID NO 646
<211> LENGTH: 21
<212> TYPE: DNA
<213> ORGANISM: homo sapiens

<400> SEQUENCE: 646
gcaacauauu caagugacat t                                              21

<210> SEQ ID NO 647
<211> LENGTH: 21
<212> TYPE: DNA
<213> ORGANISM: homo sapiens

<400> SEQUENCE: 647
ggagauuguu agcuuaggat t                                              21

<210> SEQ ID NO 648
<211> LENGTH: 21
<212> TYPE: DNA
<213> ORGANISM: homo sapiens

<400> SEQUENCE: 648
ggauacgaac caugaagaut t                                              21

<210> SEQ ID NO 649
<211> LENGTH: 21
```

```
<212> TYPE: DNA
<213> ORGANISM: homo sapiens

<400> SEQUENCE: 649
cauccuaauc uacaaaggat t                                      21

<210> SEQ ID NO 650
<211> LENGTH: 21
<212> TYPE: DNA
<213> ORGANISM: homo sapiens

<400> SEQUENCE: 650
ggagauaacg ugaacauaut t                                      21

<210> SEQ ID NO 651
<211> LENGTH: 21
<212> TYPE: DNA
<213> ORGANISM: homo sapiens

<400> SEQUENCE: 651
ggucguuacc agagauuuat t                                      21

<210> SEQ ID NO 652
<211> LENGTH: 21
<212> TYPE: DNA
<213> ORGANISM: homo sapiens

<400> SEQUENCE: 652
acguggaguu cauguguaat t                                      21

<210> SEQ ID NO 653
<211> LENGTH: 21
<212> TYPE: DNA
<213> ORGANISM: homo sapiens

<400> SEQUENCE: 653
guugauaaau cugaguauat t                                      21

<210> SEQ ID NO 654
<211> LENGTH: 21
<212> TYPE: DNA
<213> ORGANISM: homo sapiens

<400> SEQUENCE: 654
gccacacucu gcaccgcuat t                                      21

<210> SEQ ID NO 655
<211> LENGTH: 21
<212> TYPE: DNA
<213> ORGANISM: homo sapiens

<400> SEQUENCE: 655
gagcgagggu caguuugaat t                                      21

<210> SEQ ID NO 656
<211> LENGTH: 21
<212> TYPE: DNA
<213> ORGANISM: homo sapiens

<400> SEQUENCE: 656
ccaaccucua acugcagaat t                                      21

<210> SEQ ID NO 657
<211> LENGTH: 21
```

<212> TYPE: DNA
<213> ORGANISM: homo sapiens

<400> SEQUENCE: 657
guggcuuauu aauuccgaut t                                    21

<210> SEQ ID NO 658
<211> LENGTH: 21
<212> TYPE: DNA
<213> ORGANISM: homo sapiens

<400> SEQUENCE: 658
cgcaggaugg ucccuuguat t                                    21

<210> SEQ ID NO 659
<211> LENGTH: 21
<212> TYPE: DNA
<213> ORGANISM: homo sapiens

<400> SEQUENCE: 659
caggguugcc cgccaacaat t                                    21

<210> SEQ ID NO 660
<211> LENGTH: 21
<212> TYPE: DNA
<213> ORGANISM: homo sapiens

<400> SEQUENCE: 660
gggaggcauc aguugcuaut t                                    21

<210> SEQ ID NO 661
<211> LENGTH: 21
<212> TYPE: DNA
<213> ORGANISM: homo sapiens

<400> SEQUENCE: 661
ccgucagcug uaacccucat t                                    21

<210> SEQ ID NO 662
<211> LENGTH: 21
<212> TYPE: DNA
<213> ORGANISM: homo sapiens

<400> SEQUENCE: 662
gggacauuca ccacaucgat t                                    21

<210> SEQ ID NO 663
<211> LENGTH: 21
<212> TYPE: DNA
<213> ORGANISM: homo sapiens

<400> SEQUENCE: 663
agaagugcau acaccgagat t                                    21

<210> SEQ ID NO 664
<211> LENGTH: 21
<212> TYPE: DNA
<213> ORGANISM: homo sapiens

<400> SEQUENCE: 664
gucggacgca acagagaaat t                                    21

<210> SEQ ID NO 665
<211> LENGTH: 21

<212> TYPE: DNA
<213> ORGANISM: homo sapiens

<400> SEQUENCE: 665
acaccugcau uguggagaat t             21

<210> SEQ ID NO 666
<211> LENGTH: 21
<212> TYPE: DNA
<213> ORGANISM: homo sapiens

<400> SEQUENCE: 666
gcaagauugg cccagacaat t             21

<210> SEQ ID NO 667
<211> LENGTH: 21
<212> TYPE: DNA
<213> ORGANISM: homo sapiens

<400> SEQUENCE: 667
gaggcauuau uugaccggat t             21

<210> SEQ ID NO 668
<211> LENGTH: 21
<212> TYPE: DNA
<213> ORGANISM: homo sapiens

<400> SEQUENCE: 668
ugccaauggc ggacucaaat t             21

<210> SEQ ID NO 669
<211> LENGTH: 21
<212> TYPE: DNA
<213> ORGANISM: homo sapiens

<400> SEQUENCE: 669
cagacugguc uuaggcaaat t             21

<210> SEQ ID NO 670
<211> LENGTH: 21
<212> TYPE: DNA
<213> ORGANISM: homo sapiens

<400> SEQUENCE: 670
gaucuugaag acugcuggat t             21

<210> SEQ ID NO 671
<211> LENGTH: 21
<212> TYPE: DNA
<213> ORGANISM: homo sapiens

<400> SEQUENCE: 671
ggcggguaac ucuaucggat t             21

<210> SEQ ID NO 672
<211> LENGTH: 21
<212> TYPE: DNA
<213> ORGANISM: homo sapiens

<400> SEQUENCE: 672
cuguggugcc cucugacaat t             21

<210> SEQ ID NO 673
<211> LENGTH: 21

```
<212> TYPE: DNA
<213> ORGANISM: homo sapiens

<400> SEQUENCE: 673
ucguggagua ugccuccaat t                                              21

<210> SEQ ID NO 674
<211> LENGTH: 21
<212> TYPE: DNA
<213> ORGANISM: homo sapiens

<400> SEQUENCE: 674
cguccggucg ggaccgagat t                                              21

<210> SEQ ID NO 675
<211> LENGTH: 21
<212> TYPE: DNA
<213> ORGANISM: homo sapiens

<400> SEQUENCE: 675
ccaaaugccu gguaccagat t                                              21

<210> SEQ ID NO 676
<211> LENGTH: 21
<212> TYPE: DNA
<213> ORGANISM: homo sapiens

<400> SEQUENCE: 676
aggcuaucgg gcuggacaat t                                              21

<210> SEQ ID NO 677
<211> LENGTH: 21
<212> TYPE: DNA
<213> ORGANISM: homo sapiens

<400> SEQUENCE: 677
cgcacaucca guggcuaaat t                                              21

<210> SEQ ID NO 678
<211> LENGTH: 21
<212> TYPE: DNA
<213> ORGANISM: homo sapiens

<400> SEQUENCE: 678
cacagaauug gaggcuacat t                                              21

<210> SEQ ID NO 679
<211> LENGTH: 21
<212> TYPE: DNA
<213> ORGANISM: homo sapiens

<400> SEQUENCE: 679
gcuucgagcc acgauugaat t                                              21

<210> SEQ ID NO 680
<211> LENGTH: 21
<212> TYPE: DNA
<213> ORGANISM: homo sapiens

<400> SEQUENCE: 680
guggaguauc cauggagaut t                                              21

<210> SEQ ID NO 681
<211> LENGTH: 21
```

<212> TYPE: DNA
<213> ORGANISM: homo sapiens

<400> SEQUENCE: 681
cacacugcgc ugguugaaat t                                    21

<210> SEQ ID NO 682
<211> LENGTH: 21
<212> TYPE: DNA
<213> ORGANISM: homo sapiens

<400> SEQUENCE: 682
cccgacaccc ggagcucuat t                                    21

<210> SEQ ID NO 683
<211> LENGTH: 21
<212> TYPE: DNA
<213> ORGANISM: homo sapiens

<400> SEQUENCE: 683
gagauuuacc caucgguaat t                                    21

<210> SEQ ID NO 684
<211> LENGTH: 21
<212> TYPE: DNA
<213> ORGANISM: homo sapiens

<400> SEQUENCE: 684
gggucguuac cagagauuut t                                    21

<210> SEQ ID NO 685
<211> LENGTH: 21
<212> TYPE: DNA
<213> ORGANISM: homo sapiens

<400> SEQUENCE: 685
ggaggcauca guugcuauat t                                    21

<210> SEQ ID NO 686
<211> LENGTH: 21
<212> TYPE: DNA
<213> ORGANISM: homo sapiens

<400> SEQUENCE: 686
agcgaggguc aguuugaaat t                                    21

<210> SEQ ID NO 687
<211> LENGTH: 21
<212> TYPE: DNA
<213> ORGANISM: homo sapiens

<400> SEQUENCE: 687
aguugauaaa ucugaguaut t                                    21

<210> SEQ ID NO 688
<211> LENGTH: 21
<212> TYPE: DNA
<213> ORGANISM: homo sapiens

<400> SEQUENCE: 688
agagauuuac ccaucgguat t                                    21

<210> SEQ ID NO 689
<211> LENGTH: 21

```
<212> TYPE: DNA
<213> ORGANISM: homo sapiens

<400> SEQUENCE: 689
gcaggauggu cccuuguaut t                                            21

<210> SEQ ID NO 690
<211> LENGTH: 21
<212> TYPE: DNA
<213> ORGANISM: homo sapiens

<400> SEQUENCE: 690
aaguugauaa aucgaguat t                                             21

<210> SEQ ID NO 691
<211> LENGTH: 21
<212> TYPE: DNA
<213> ORGANISM: homo sapiens

<400> SEQUENCE: 691
caagaagugc auacaccgat t                                            21

<210> SEQ ID NO 692
<211> LENGTH: 21
<212> TYPE: DNA
<213> ORGANISM: homo sapiens

<400> SEQUENCE: 692
uguaugucau cguggaguat t                                            21

<210> SEQ ID NO 693
<211> LENGTH: 21
<212> TYPE: DNA
<213> ORGANISM: homo sapiens

<400> SEQUENCE: 693
aguggcuuau uaauuccgat t                                            21

<210> SEQ ID NO 694
<211> LENGTH: 21
<212> TYPE: DNA
<213> ORGANISM: homo sapiens

<400> SEQUENCE: 694
gcaucauaau ggacucugut t                                            21

<210> SEQ ID NO 695
<211> LENGTH: 21
<212> TYPE: DNA
<213> ORGANISM: homo sapiens

<400> SEQUENCE: 695
aguuaauacc accgacaaat t                                            21

<210> SEQ ID NO 696
<211> LENGTH: 21
<212> TYPE: DNA
<213> ORGANISM: homo sapiens

<400> SEQUENCE: 696
ggagcaucau aauggacuct t                                            21

<210> SEQ ID NO 697
<211> LENGTH: 21
```

```
<212> TYPE: DNA
<213> ORGANISM: homo sapiens

<400> SEQUENCE: 697
uggcuuauua auuccgauat t                                              21

<210> SEQ ID NO 698
<211> LENGTH: 21
<212> TYPE: DNA
<213> ORGANISM: homo sapiens

<400> SEQUENCE: 698
aggcauuauu ugaccggaut t                                              21

<210> SEQ ID NO 699
<211> LENGTH: 21
<212> TYPE: DNA
<213> ORGANISM: homo sapiens

<400> SEQUENCE: 699
agucggacgc aacagagaat t                                              21

<210> SEQ ID NO 700
<211> LENGTH: 21
<212> TYPE: DNA
<213> ORGANISM: homo sapiens

<400> SEQUENCE: 700
cacgggacau ucaccacaut t                                              21

<210> SEQ ID NO 701
<211> LENGTH: 21
<212> TYPE: DNA
<213> ORGANISM: homo sapiens

<400> SEQUENCE: 701
ggcagauguu ccuaauaaat t                                              21

<210> SEQ ID NO 702
<211> LENGTH: 21
<212> TYPE: DNA
<213> ORGANISM: homo sapiens

<400> SEQUENCE: 702
ggugcuucag uuagaucaat t                                              21

<210> SEQ ID NO 703
<211> LENGTH: 21
<212> TYPE: DNA
<213> ORGANISM: homo sapiens

<400> SEQUENCE: 703
ggcuuaccau ccaaacaaut t                                              21

<210> SEQ ID NO 704
<211> LENGTH: 21
<212> TYPE: DNA
<213> ORGANISM: homo sapiens

<400> SEQUENCE: 704
cccacuaacu ggcuaauuat t                                              21

<210> SEQ ID NO 705
<211> LENGTH: 21
```

```
<212> TYPE: DNA
<213> ORGANISM: homo sapiens

<400> SEQUENCE: 705
gcaccuccau ggaaacgaat t                                              21

<210> SEQ ID NO 706
<211> LENGTH: 21
<212> TYPE: DNA
<213> ORGANISM: homo sapiens

<400> SEQUENCE: 706
cgaaucugac auuagaugat t                                              21

<210> SEQ ID NO 707
<211> LENGTH: 21
<212> TYPE: DNA
<213> ORGANISM: homo sapiens

<400> SEQUENCE: 707
cugagacacu caacaaguat t                                              21

<210> SEQ ID NO 708
<211> LENGTH: 21
<212> TYPE: DNA
<213> ORGANISM: homo sapiens

<400> SEQUENCE: 708
ggaguucuug gcacgucaut t                                              21

<210> SEQ ID NO 709
<211> LENGTH: 21
<212> TYPE: DNA
<213> ORGANISM: homo sapiens

<400> SEQUENCE: 709
gcuaugaggu ccugggaaat t                                              21

<210> SEQ ID NO 710
<211> LENGTH: 21
<212> TYPE: DNA
<213> ORGANISM: homo sapiens

<400> SEQUENCE: 710
cgaugaagga auaucucuut t                                              21

<210> SEQ ID NO 711
<211> LENGTH: 21
<212> TYPE: DNA
<213> ORGANISM: homo sapiens

<400> SEQUENCE: 711
cacaggagca ucuccucaat t                                              21

<210> SEQ ID NO 712
<211> LENGTH: 21
<212> TYPE: DNA
<213> ORGANISM: homo sapiens

<400> SEQUENCE: 712
ccagaucuau gccacaagat t                                              21

<210> SEQ ID NO 713
<211> LENGTH: 21
```

```
<212> TYPE: DNA
<213> ORGANISM: homo sapiens

<400> SEQUENCE: 713
ggcucuggac aggcacuaut t                                              21

<210> SEQ ID NO 714
<211> LENGTH: 21
<212> TYPE: DNA
<213> ORGANISM: homo sapiens

<400> SEQUENCE: 714
ggcuggaugc ucucguugat t                                              21

<210> SEQ ID NO 715
<211> LENGTH: 21
<212> TYPE: DNA
<213> ORGANISM: homo sapiens

<400> SEQUENCE: 715
caagauccug gcuaugcaut t                                              21

<210> SEQ ID NO 716
<211> LENGTH: 21
<212> TYPE: DNA
<213> ORGANISM: homo sapiens

<400> SEQUENCE: 716
gcuguugagg uaccuccaat t                                              21

<210> SEQ ID NO 717
<211> LENGTH: 21
<212> TYPE: DNA
<213> ORGANISM: homo sapiens

<400> SEQUENCE: 717
agaauaacca acacccugat t                                              21

<210> SEQ ID NO 718
<211> LENGTH: 21
<212> TYPE: DNA
<213> ORGANISM: homo sapiens

<400> SEQUENCE: 718
caugucaaau auuacagaut t                                              21

<210> SEQ ID NO 719
<211> LENGTH: 21
<212> TYPE: DNA
<213> ORGANISM: homo sapiens

<400> SEQUENCE: 719
aaguggaacg agacaagcat t                                              21

<210> SEQ ID NO 720
<211> LENGTH: 21
<212> TYPE: DNA
<213> ORGANISM: homo sapiens

<400> SEQUENCE: 720
gucucuucca accucugaat t                                              21

<210> SEQ ID NO 721
<211> LENGTH: 21
```

-continued

<212> TYPE: DNA
<213> ORGANISM: homo sapiens

<400> SEQUENCE: 721
cgccaggcuu accauccaat t                                              21

<210> SEQ ID NO 722
<211> LENGTH: 21
<212> TYPE: DNA
<213> ORGANISM: homo sapiens

<400> SEQUENCE: 722
guugaacguc acaucuuuat t                                              21

<210> SEQ ID NO 723
<211> LENGTH: 21
<212> TYPE: DNA
<213> ORGANISM: homo sapiens

<400> SEQUENCE: 723
ggccggugcu ucaguuagat t                                              21

<210> SEQ ID NO 724
<211> LENGTH: 21
<212> TYPE: DNA
<213> ORGANISM: homo sapiens

<400> SEQUENCE: 724
gcaccaucau ucccguugat t                                              21

<210> SEQ ID NO 725
<211> LENGTH: 21
<212> TYPE: DNA
<213> ORGANISM: homo sapiens

<400> SEQUENCE: 725
aggcuuacca uccaaacaat t                                              21

<210> SEQ ID NO 726
<211> LENGTH: 21
<212> TYPE: DNA
<213> ORGANISM: homo sapiens

<400> SEQUENCE: 726
gccaggcuua ccauccaaat t                                              21

<210> SEQ ID NO 727
<211> LENGTH: 21
<212> TYPE: DNA
<213> ORGANISM: homo sapiens

<400> SEQUENCE: 727
gugcuucagu uagaucaaat t                                              21

<210> SEQ ID NO 728
<211> LENGTH: 21
<212> TYPE: DNA
<213> ORGANISM: homo sapiens

<400> SEQUENCE: 728
caccaucauu cccguugaat t                                              21

<210> SEQ ID NO 729
<211> LENGTH: 21

```
<212> TYPE: DNA
<213> ORGANISM: homo sapiens

<400> SEQUENCE: 729
ccuccaugga aacgaagcat t                                              21

<210> SEQ ID NO 730
<211> LENGTH: 21
<212> TYPE: DNA
<213> ORGANISM: homo sapiens

<400> SEQUENCE: 730
agaggguuug gaagccagat t                                              21

<210> SEQ ID NO 731
<211> LENGTH: 21
<212> TYPE: DNA
<213> ORGANISM: homo sapiens

<400> SEQUENCE: 731
cuaacuggcu aauuagcaut t                                              21

<210> SEQ ID NO 732
<211> LENGTH: 21
<212> TYPE: DNA
<213> ORGANISM: homo sapiens

<400> SEQUENCE: 732
caucgaugaa ggaauaucut t                                              21

<210> SEQ ID NO 733
<211> LENGTH: 21
<212> TYPE: DNA
<213> ORGANISM: homo sapiens

<400> SEQUENCE: 733
aggcagaugu uccuaauaat t                                              21

<210> SEQ ID NO 734
<211> LENGTH: 21
<212> TYPE: DNA
<213> ORGANISM: homo sapiens

<400> SEQUENCE: 734
ccacuaacug gcuaauuagt t                                              21

<210> SEQ ID NO 735
<211> LENGTH: 21
<212> TYPE: DNA
<213> ORGANISM: homo sapiens

<400> SEQUENCE: 735
cggugcuuca guuagaucat t                                              21

<210> SEQ ID NO 736
<211> LENGTH: 21
<212> TYPE: DNA
<213> ORGANISM: homo sapiens

<400> SEQUENCE: 736
gcuuaccauc caaacaauut t                                              21

<210> SEQ ID NO 737
<211> LENGTH: 21
```

```
<212> TYPE: DNA
<213> ORGANISM: homo sapiens

<400> SEQUENCE: 737
ccgccaggcu uaccauccat t                                        21

<210> SEQ ID NO 738
<211> LENGTH: 21
<212> TYPE: DNA
<213> ORGANISM: homo sapiens

<400> SEQUENCE: 738
ugcauggccu ggucagcaat t                                        21

<210> SEQ ID NO 739
<211> LENGTH: 21
<212> TYPE: DNA
<213> ORGANISM: homo sapiens

<400> SEQUENCE: 739
gaggguuugg aagccagaut t                                        21

<210> SEQ ID NO 740
<211> LENGTH: 21
<212> TYPE: DNA
<213> ORGANISM: homo sapiens

<400> SEQUENCE: 740
ucaguuagau caaaccauut t                                        21

<210> SEQ ID NO 741
<211> LENGTH: 21
<212> TYPE: DNA
<213> ORGANISM: homo sapiens

<400> SEQUENCE: 741
gccuuugcac cuccauggat t                                        21

<210> SEQ ID NO 742
<211> LENGTH: 21
<212> TYPE: DNA
<213> ORGANISM: homo sapiens

<400> SEQUENCE: 742
ggaaacgaag caccaucaut t                                        21

<210> SEQ ID NO 743
<211> LENGTH: 21
<212> TYPE: DNA
<213> ORGANISM: homo sapiens

<400> SEQUENCE: 743
caggcuuacc auccaaacat t                                        21

<210> SEQ ID NO 744
<211> LENGTH: 21
<212> TYPE: DNA
<213> ORGANISM: homo sapiens

<400> SEQUENCE: 744
cagaucuaug ccacaagaat t                                        21

<210> SEQ ID NO 745
<211> LENGTH: 21
```

-continued

```
<212> TYPE: DNA
<213> ORGANISM: homo sapiens

<400> SEQUENCE: 745
ggaugcucuc guugacccut t                                              21

<210> SEQ ID NO 746
<211> LENGTH: 21
<212> TYPE: DNA
<213> ORGANISM: homo sapiens

<400> SEQUENCE: 746
uguugugauc aucgccuaut t                                              21

<210> SEQ ID NO 747
<211> LENGTH: 21
<212> TYPE: DNA
<213> ORGANISM: homo sapiens

<400> SEQUENCE: 747
ugagacacuc aacaaguaut t                                              21

<210> SEQ ID NO 748
<211> LENGTH: 21
<212> TYPE: DNA
<213> ORGANISM: homo sapiens

<400> SEQUENCE: 748
gaaacgaagc accaucauut t                                              21

<210> SEQ ID NO 749
<211> LENGTH: 21
<212> TYPE: DNA
<213> ORGANISM: homo sapiens

<400> SEQUENCE: 749
gcagauguuc cuaauaaagt t                                              21

<210> SEQ ID NO 750
<211> LENGTH: 21
<212> TYPE: DNA
<213> ORGANISM: homo sapiens

<400> SEQUENCE: 750
gucaucgugu uaccuccuat t                                              21

<210> SEQ ID NO 751
<211> LENGTH: 21
<212> TYPE: DNA
<213> ORGANISM: homo sapiens

<400> SEQUENCE: 751
ccacuaaauu gacacuuaat t                                              21

<210> SEQ ID NO 752
<211> LENGTH: 21
<212> TYPE: DNA
<213> ORGANISM: homo sapiens

<400> SEQUENCE: 752
ggaauugacc cacaagaaat t                                              21

<210> SEQ ID NO 753
<211> LENGTH: 21
```

```
<212> TYPE: DNA
<213> ORGANISM: homo sapiens

<400> SEQUENCE: 753
gcuuauucac aagacccaat t                                            21

<210> SEQ ID NO 754
<211> LENGTH: 21
<212> TYPE: DNA
<213> ORGANISM: homo sapiens

<400> SEQUENCE: 754
cuauguucua agaagugaat t                                            21

<210> SEQ ID NO 755
<211> LENGTH: 21
<212> TYPE: DNA
<213> ORGANISM: homo sapiens

<400> SEQUENCE: 755
ggaccgucua cucauccaat t                                            21

<210> SEQ ID NO 756
<211> LENGTH: 21
<212> TYPE: DNA
<213> ORGANISM: homo sapiens

<400> SEQUENCE: 756
aggugaagau cuuaguaaut t                                            21

<210> SEQ ID NO 757
<211> LENGTH: 21
<212> TYPE: DNA
<213> ORGANISM: homo sapiens

<400> SEQUENCE: 757
ccaaggcuga uuaaaccaat t                                            21

<210> SEQ ID NO 758
<211> LENGTH: 21
<212> TYPE: DNA
<213> ORGANISM: homo sapiens

<400> SEQUENCE: 758
gcagauaaac aguagugaut t                                            21

<210> SEQ ID NO 759
<211> LENGTH: 21
<212> TYPE: DNA
<213> ORGANISM: homo sapiens

<400> SEQUENCE: 759
ggcggaugcu guuacggaut t                                            21

<210> SEQ ID NO 760
<211> LENGTH: 21
<212> TYPE: DNA
<213> ORGANISM: homo sapiens

<400> SEQUENCE: 760
caagauucua gcuauacaut t                                            21

<210> SEQ ID NO 761
<211> LENGTH: 21
```

```
<212> TYPE: DNA
<213> ORGANISM: homo sapiens

<400> SEQUENCE: 761
gggccaugcg ggucaucuut t                                              21

<210> SEQ ID NO 762
<211> LENGTH: 21
<212> TYPE: DNA
<213> ORGANISM: homo sapiens

<400> SEQUENCE: 762
ccuacaugag guacugagat t                                              21

<210> SEQ ID NO 763
<211> LENGTH: 21
<212> TYPE: DNA
<213> ORGANISM: homo sapiens

<400> SEQUENCE: 763
gaagcgcuac uuggucaaat t                                              21

<210> SEQ ID NO 764
<211> LENGTH: 21
<212> TYPE: DNA
<213> ORGANISM: homo sapiens

<400> SEQUENCE: 764
gugauaugua ccuaacgaat t                                              21

<210> SEQ ID NO 765
<211> LENGTH: 21
<212> TYPE: DNA
<213> ORGANISM: homo sapiens

<400> SEQUENCE: 765
agaggaauga aguacucaut t                                              21

<210> SEQ ID NO 766
<211> LENGTH: 21
<212> TYPE: DNA
<213> ORGANISM: homo sapiens

<400> SEQUENCE: 766
agcucugacu accacccaat t                                              21

<210> SEQ ID NO 767
<211> LENGTH: 21
<212> TYPE: DNA
<213> ORGANISM: homo sapiens

<400> SEQUENCE: 767
cccuugcaug guuuagaaat t                                              21

<210> SEQ ID NO 768
<211> LENGTH: 21
<212> TYPE: DNA
<213> ORGANISM: homo sapiens

<400> SEQUENCE: 768
acauagaauu aacacaugat t                                              21

<210> SEQ ID NO 769
<211> LENGTH: 21
```

```
<212> TYPE: DNA
<213> ORGANISM: homo sapiens

<400> SEQUENCE: 769
guaccgcaau gugacuuaat t                                           21

<210> SEQ ID NO 770
<211> LENGTH: 21
<212> TYPE: DNA
<213> ORGANISM: homo sapiens

<400> SEQUENCE: 770
ggacaugggc aacaauacat t                                           21

<210> SEQ ID NO 771
<211> LENGTH: 21
<212> TYPE: DNA
<213> ORGANISM: homo sapiens

<400> SEQUENCE: 771
cuccaauaac agcaggucat t                                           21

<210> SEQ ID NO 772
<211> LENGTH: 21
<212> TYPE: DNA
<213> ORGANISM: homo sapiens

<400> SEQUENCE: 772
gaaccaccug ccuauauuut t                                           21

<210> SEQ ID NO 773
<211> LENGTH: 21
<212> TYPE: DNA
<213> ORGANISM: homo sapiens

<400> SEQUENCE: 773
gaaguuucau cgucaaggut t                                           21

<210> SEQ ID NO 774
<211> LENGTH: 21
<212> TYPE: DNA
<213> ORGANISM: homo sapiens

<400> SEQUENCE: 774
acacggacga accuugaaat t                                           21

<210> SEQ ID NO 775
<211> LENGTH: 21
<212> TYPE: DNA
<213> ORGANISM: homo sapiens

<400> SEQUENCE: 775
aggauuuaag uuuaccucat t                                           21

<210> SEQ ID NO 776
<211> LENGTH: 21
<212> TYPE: DNA
<213> ORGANISM: homo sapiens

<400> SEQUENCE: 776
acgccuucau uggccagaat t                                           21

<210> SEQ ID NO 777
<211> LENGTH: 21
```

```
<212> TYPE: DNA
<213> ORGANISM: homo sapiens

<400> SEQUENCE: 777
cacuaaauug acacuuaaat t                                              21

<210> SEQ ID NO 778
<211> LENGTH: 21
<212> TYPE: DNA
<213> ORGANISM: homo sapiens

<400> SEQUENCE: 778
cauggcacuc uauguucuat t                                              21

<210> SEQ ID NO 779
<211> LENGTH: 21
<212> TYPE: DNA
<213> ORGANISM: homo sapiens

<400> SEQUENCE: 779
ggugaagauc uuaguaauut t                                              21

<210> SEQ ID NO 780
<211> LENGTH: 21
<212> TYPE: DNA
<213> ORGANISM: homo sapiens

<400> SEQUENCE: 780
gucuacucau ccaauguuat t                                              21

<210> SEQ ID NO 781
<211> LENGTH: 21
<212> TYPE: DNA
<213> ORGANISM: homo sapiens

<400> SEQUENCE: 781
ggcacucuau guucuaagat t                                              21

<210> SEQ ID NO 782
<211> LENGTH: 21
<212> TYPE: DNA
<213> ORGANISM: homo sapiens

<400> SEQUENCE: 782
gcaaugugac uuaaugccat t                                              21

<210> SEQ ID NO 783
<211> LENGTH: 21
<212> TYPE: DNA
<213> ORGANISM: homo sapiens

<400> SEQUENCE: 783
gcugauuaaa ccaaggcuat t                                              21

<210> SEQ ID NO 784
<211> LENGTH: 21
<212> TYPE: DNA
<213> ORGANISM: homo sapiens

<400> SEQUENCE: 784
aggaauugac ccacaagaat t                                              21

<210> SEQ ID NO 785
<211> LENGTH: 21
```

```
<212> TYPE: DNA
<213> ORGANISM: homo sapiens

<400> SEQUENCE: 785
cagauaaaca guagugauat t                                              21

<210> SEQ ID NO 786
<211> LENGTH: 21
<212> TYPE: DNA
<213> ORGANISM: homo sapiens

<400> SEQUENCE: 786
gaaguauccu ucagccugat t                                              21

<210> SEQ ID NO 787
<211> LENGTH: 21
<212> TYPE: DNA
<213> ORGANISM: homo sapiens

<400> SEQUENCE: 787
cagacauaga auuaacacat t                                              21

<210> SEQ ID NO 788
<211> LENGTH: 21
<212> TYPE: DNA
<213> ORGANISM: homo sapiens

<400> SEQUENCE: 788
gaggacaugg gcaacaauat t                                              21

<210> SEQ ID NO 789
<211> LENGTH: 21
<212> TYPE: DNA
<213> ORGANISM: homo sapiens

<400> SEQUENCE: 789
uauaggaauu gacccacaat t                                              21

<210> SEQ ID NO 790
<211> LENGTH: 21
<212> TYPE: DNA
<213> ORGANISM: homo sapiens

<400> SEQUENCE: 790
gaauugaccc acaagaaaut t                                              21

<210> SEQ ID NO 791
<211> LENGTH: 21
<212> TYPE: DNA
<213> ORGANISM: homo sapiens

<400> SEQUENCE: 791
gguggccacu ccauaaacat t                                              21

<210> SEQ ID NO 792
<211> LENGTH: 21
<212> TYPE: DNA
<213> ORGANISM: homo sapiens

<400> SEQUENCE: 792
gagugaacaa auuuacagat t                                              21

<210> SEQ ID NO 793
<211> LENGTH: 21
```

-continued

```
<212> TYPE: DNA
<213> ORGANISM: homo sapiens

<400> SEQUENCE: 793
agugauaguu guaccgcaat t                                              21

<210> SEQ ID NO 794
<211> LENGTH: 21
<212> TYPE: DNA
<213> ORGANISM: homo sapiens

<400> SEQUENCE: 794
cgaaggaccg ucuacucaut t                                              21

<210> SEQ ID NO 795
<211> LENGTH: 21
<212> TYPE: DNA
<213> ORGANISM: homo sapiens

<400> SEQUENCE: 795
gugaagaucu uaguaauuat t                                              21

<210> SEQ ID NO 796
<211> LENGTH: 21
<212> TYPE: DNA
<213> ORGANISM: homo sapiens

<400> SEQUENCE: 796
caucgucaag guuguuucat t                                              21

<210> SEQ ID NO 797
<211> LENGTH: 21
<212> TYPE: DNA
<213> ORGANISM: homo sapiens

<400> SEQUENCE: 797
gcuauacaug gcuugaucat t                                              21

<210> SEQ ID NO 798
<211> LENGTH: 21
<212> TYPE: DNA
<213> ORGANISM: homo sapiens

<400> SEQUENCE: 798
gaagaucuua guaauuacat t                                              21

<210> SEQ ID NO 799
<211> LENGTH: 21
<212> TYPE: DNA
<213> ORGANISM: homo sapiens

<400> SEQUENCE: 799
cgcuacuugg ucaaauucat t                                              21

<210> SEQ ID NO 800
<211> LENGTH: 21
<212> TYPE: DNA
<213> ORGANISM: homo sapiens

<400> SEQUENCE: 800
auauguaccu aacgaaguat t                                              21

<210> SEQ ID NO 801
<211> LENGTH: 21
```

-continued

```
<212> TYPE: DNA
<213> ORGANISM: homo sapiens

<400> SEQUENCE: 801
gaggaagacu guuacuacat t                                           21

<210> SEQ ID NO 802
<211> LENGTH: 21
<212> TYPE: DNA
<213> ORGANISM: homo sapiens

<400> SEQUENCE: 802
guugcuagau uaucguccat t                                           21

<210> SEQ ID NO 803
<211> LENGTH: 21
<212> TYPE: DNA
<213> ORGANISM: homo sapiens

<400> SEQUENCE: 803
gauggccaau ucugccauat t                                           21

<210> SEQ ID NO 804
<211> LENGTH: 21
<212> TYPE: DNA
<213> ORGANISM: homo sapiens

<400> SEQUENCE: 804
cccuguccuc caggugaaat t                                           21

<210> SEQ ID NO 805
<211> LENGTH: 21
<212> TYPE: DNA
<213> ORGANISM: homo sapiens

<400> SEQUENCE: 805
aguguuaaug cccaagugat t                                           21

<210> SEQ ID NO 806
<211> LENGTH: 21
<212> TYPE: DNA
<213> ORGANISM: homo sapiens

<400> SEQUENCE: 806
ccaagugcaa agaggaagut t                                           21

<210> SEQ ID NO 807
<211> LENGTH: 21
<212> TYPE: DNA
<213> ORGANISM: homo sapiens

<400> SEQUENCE: 807
aucaaggaau gcacacucat t                                           21

<210> SEQ ID NO 808
<211> LENGTH: 21
<212> TYPE: DNA
<213> ORGANISM: homo sapiens

<400> SEQUENCE: 808
gugcccugcc aagaagggat t                                           21

<210> SEQ ID NO 809
<211> LENGTH: 21
```

```
<212> TYPE: DNA
<213> ORGANISM: homo sapiens

<400> SEQUENCE: 809
agcuagggac ugcacaguct t                                              21

<210> SEQ ID NO 810
<211> LENGTH: 21
<212> TYPE: DNA
<213> ORGANISM: homo sapiens

<400> SEQUENCE: 810
ggaaggccug caucaugaut t                                              21

<210> SEQ ID NO 811
<211> LENGTH: 21
<212> TYPE: DNA
<213> ORGANISM: homo sapiens

<400> SEQUENCE: 811
cuacaguuga gacucagaat t                                              21

<210> SEQ ID NO 812
<211> LENGTH: 21
<212> TYPE: DNA
<213> ORGANISM: homo sapiens

<400> SEQUENCE: 812
uacgucuguu gcuagauuat t                                              21

<210> SEQ ID NO 813
<211> LENGTH: 21
<212> TYPE: DNA
<213> ORGANISM: homo sapiens

<400> SEQUENCE: 813
agacuguuac uacaguugat t                                              21

<210> SEQ ID NO 814
<211> LENGTH: 21
<212> TYPE: DNA
<213> ORGANISM: homo sapiens

<400> SEQUENCE: 814
gacuguuacu acaguugagt t                                              21

<210> SEQ ID NO 815
<211> LENGTH: 21
<212> TYPE: DNA
<213> ORGANISM: homo sapiens

<400> SEQUENCE: 815
gguucuuacg ucuguugcut t                                              21

<210> SEQ ID NO 816
<211> LENGTH: 21
<212> TYPE: DNA
<213> ORGANISM: homo sapiens

<400> SEQUENCE: 816
acuacaguug agacucagat t                                              21

<210> SEQ ID NO 817
<211> LENGTH: 21
```

```
<212> TYPE: DNA
<213> ORGANISM: homo sapiens

<400> SEQUENCE: 817
guccuccagg ugaaaggaat t                                          21

<210> SEQ ID NO 818
<211> LENGTH: 21
<212> TYPE: DNA
<213> ORGANISM: homo sapiens

<400> SEQUENCE: 818
uugcuagauu aucguccaat t                                          21

<210> SEQ ID NO 819
<211> LENGTH: 21
<212> TYPE: DNA
<213> ORGANISM: homo sapiens

<400> SEQUENCE: 819
ggaagacugu uacuacagut t                                          21

<210> SEQ ID NO 820
<211> LENGTH: 21
<212> TYPE: DNA
<213> ORGANISM: homo sapiens

<400> SEQUENCE: 820
uggaaggccu gcaucaugat t                                          21

<210> SEQ ID NO 821
<211> LENGTH: 21
<212> TYPE: DNA
<213> ORGANISM: homo sapiens

<400> SEQUENCE: 821
uccaagggau uggaauugat t                                          21

<210> SEQ ID NO 822
<211> LENGTH: 21
<212> TYPE: DNA
<213> ORGANISM: homo sapiens

<400> SEQUENCE: 822
ggaaagcuag ggacugcact t                                          21

<210> SEQ ID NO 823
<211> LENGTH: 21
<212> TYPE: DNA
<213> ORGANISM: homo sapiens

<400> SEQUENCE: 823
guugagacuc agaacuuggt t                                          21

<210> SEQ ID NO 824
<211> LENGTH: 21
<212> TYPE: DNA
<213> ORGANISM: homo sapiens

<400> SEQUENCE: 824
cgucuguugc uagauuauct t                                          21

<210> SEQ ID NO 825
<211> LENGTH: 21
```

<212> TYPE: DNA
<213> ORGANISM: homo sapiens

<400> SEQUENCE: 825
auggccaauu cugccauaat t                                              21

<210> SEQ ID NO 826
<211> LENGTH: 21
<212> TYPE: DNA
<213> ORGANISM: homo sapiens

<400> SEQUENCE: 826
aguugagacu cagaacuugt t                                              21

<210> SEQ ID NO 827
<211> LENGTH: 21
<212> TYPE: DNA
<213> ORGANISM: homo sapiens

<400> SEQUENCE: 827
gaaagcuagg gacugcacat t                                              21

<210> SEQ ID NO 828
<211> LENGTH: 21
<212> TYPE: DNA
<213> ORGANISM: homo sapiens

<400> SEQUENCE: 828
ugacaucaac uccaagggat t                                              21

<210> SEQ ID NO 829
<211> LENGTH: 21
<212> TYPE: DNA
<213> ORGANISM: homo sapiens

<400> SEQUENCE: 829
ugauggccaa uucugccaut t                                              21

<210> SEQ ID NO 830
<211> LENGTH: 21
<212> TYPE: DNA
<213> ORGANISM: homo sapiens

<400> SEQUENCE: 830
gccugcauca ugauggccat t                                              21

<210> SEQ ID NO 831
<211> LENGTH: 21
<212> TYPE: DNA
<213> ORGANISM: homo sapiens

<400> SEQUENCE: 831
guguuaaugc ccaagugact t                                              21

<210> SEQ ID NO 832
<211> LENGTH: 21
<212> TYPE: DNA
<213> ORGANISM: homo sapiens

<400> SEQUENCE: 832
ggccaauucu gccauaagct t                                              21

<210> SEQ ID NO 833
<211> LENGTH: 21

```
<212> TYPE: DNA
<213> ORGANISM: homo sapiens

<400> SEQUENCE: 833
gucuguugcu agauuaucgt t                                              21

<210> SEQ ID NO 834
<211> LENGTH: 21
<212> TYPE: DNA
<213> ORGANISM: homo sapiens

<400> SEQUENCE: 834
acuguuacua caguugagat t                                              21

<210> SEQ ID NO 835
<211> LENGTH: 21
<212> TYPE: DNA
<213> ORGANISM: homo sapiens

<400> SEQUENCE: 835
cuuacgucug uugcuagaut t                                              21

<210> SEQ ID NO 836
<211> LENGTH: 21
<212> TYPE: DNA
<213> ORGANISM: homo sapiens

<400> SEQUENCE: 836
uguuaaugcc caagugacut t                                              21

<210> SEQ ID NO 837
<211> LENGTH: 21
<212> TYPE: DNA
<213> ORGANISM: homo sapiens

<400> SEQUENCE: 837
caauucugcc auaagcccut t                                              21

<210> SEQ ID NO 838
<211> LENGTH: 21
<212> TYPE: DNA
<213> ORGANISM: homo sapiens

<400> SEQUENCE: 838
uuacuacagu ugagacucat t                                              21

<210> SEQ ID NO 839
<211> LENGTH: 21
<212> TYPE: DNA
<213> ORGANISM: homo sapiens

<400> SEQUENCE: 839
acaguugaga cucagaacut t                                              21

<210> SEQ ID NO 840
<211> LENGTH: 21
<212> TYPE: DNA
<213> ORGANISM: homo sapiens

<400> SEQUENCE: 840
ugcuagauua ucguccaaat t                                              21

<210> SEQ ID NO 841
<211> LENGTH: 21
```

```
<212> TYPE: DNA
<213> ORGANISM: homo sapiens

<400> SEQUENCE: 841
caagggauug gaauugaggt t                                              21

<210> SEQ ID NO 842
<211> LENGTH: 21
<212> TYPE: DNA
<213> ORGANISM: homo sapiens

<400> SEQUENCE: 842
augauggcca auucugccat t                                              21

<210> SEQ ID NO 843
<211> LENGTH: 21
<212> TYPE: DNA
<213> ORGANISM: homo sapiens

<400> SEQUENCE: 843
aggaagacug uuacuacagt t                                              21

<210> SEQ ID NO 844
<211> LENGTH: 21
<212> TYPE: DNA
<213> ORGANISM: homo sapiens

<400> SEQUENCE: 844
ucuuacgucu guugcuagat t                                              21

<210> SEQ ID NO 845
<211> LENGTH: 21
<212> TYPE: DNA
<213> ORGANISM: homo sapiens

<400> SEQUENCE: 845
ucuguugcua gauuaucgut t                                              21

<210> SEQ ID NO 846
<211> LENGTH: 21
<212> TYPE: DNA
<213> ORGANISM: homo sapiens

<400> SEQUENCE: 846
uguuacuaca guugagacut t                                              21

<210> SEQ ID NO 847
<211> LENGTH: 21
<212> TYPE: DNA
<213> ORGANISM: homo sapiens

<400> SEQUENCE: 847
auucugccau aagcccugut t                                              21

<210> SEQ ID NO 848
<211> LENGTH: 21
<212> TYPE: DNA
<213> ORGANISM: homo sapiens

<400> SEQUENCE: 848
uuacgucugu ugcuagauut t                                              21

<210> SEQ ID NO 849
<211> LENGTH: 21
```

```
<212> TYPE: DNA
<213> ORGANISM: homo sapiens

<400> SEQUENCE: 849
uggccaauuc ugccauaagt t                                              21

<210> SEQ ID NO 850
<211> LENGTH: 21
<212> TYPE: DNA
<213> ORGANISM: homo sapiens

<400> SEQUENCE: 850
gaaccagacu gcgugcccut t                                              21

<210> SEQ ID NO 851
<211> LENGTH: 21
<212> TYPE: DNA
<213> ORGANISM: homo sapiens

<400> SEQUENCE: 851
gggugucaua ggugacaaat t                                              21

<210> SEQ ID NO 852
<211> LENGTH: 21
<212> TYPE: DNA
<213> ORGANISM: homo sapiens

<400> SEQUENCE: 852
gaccaggcuu gcucuauaat t                                              21

<210> SEQ ID NO 853
<211> LENGTH: 21
<212> TYPE: DNA
<213> ORGANISM: homo sapiens

<400> SEQUENCE: 853
ggaagauacc acaaucagat t                                              21

<210> SEQ ID NO 854
<211> LENGTH: 21
<212> TYPE: DNA
<213> ORGANISM: homo sapiens

<400> SEQUENCE: 854
gcauaauugu ccugaaauat t                                              21

<210> SEQ ID NO 855
<211> LENGTH: 21
<212> TYPE: DNA
<213> ORGANISM: homo sapiens

<400> SEQUENCE: 855
ggaggaaaua cuacauuaat t                                              21

<210> SEQ ID NO 856
<211> LENGTH: 21
<212> TYPE: DNA
<213> ORGANISM: homo sapiens

<400> SEQUENCE: 856
cgcagguaac gaugggaaat t                                              21

<210> SEQ ID NO 857
<211> LENGTH: 21
```

```
<212> TYPE: DNA
<213> ORGANISM: homo sapiens

<400> SEQUENCE: 857
ggaugaucca acugaacuat t                                              21

<210> SEQ ID NO 858
<211> LENGTH: 21
<212> TYPE: DNA
<213> ORGANISM: homo sapiens

<400> SEQUENCE: 858
gcuuaguguc agaaggcaat t                                              21

<210> SEQ ID NO 859
<211> LENGTH: 21
<212> TYPE: DNA
<213> ORGANISM: homo sapiens

<400> SEQUENCE: 859
gaggcggcac acccuauaat t                                              21

<210> SEQ ID NO 860
<211> LENGTH: 21
<212> TYPE: DNA
<213> ORGANISM: homo sapiens

<400> SEQUENCE: 860
ccuauauuuc agauggaaat t                                              21

<210> SEQ ID NO 861
<211> LENGTH: 21
<212> TYPE: DNA
<213> ORGANISM: homo sapiens

<400> SEQUENCE: 861
gacugaagcu ggugcgcaat t                                              21

<210> SEQ ID NO 862
<211> LENGTH: 21
<212> TYPE: DNA
<213> ORGANISM: homo sapiens

<400> SEQUENCE: 862
acccugauuu cuacaucaat t                                              21

<210> SEQ ID NO 863
<211> LENGTH: 21
<212> TYPE: DNA
<213> ORGANISM: homo sapiens

<400> SEQUENCE: 863
gguguucuau ugcugagaat t                                              21

<210> SEQ ID NO 864
<211> LENGTH: 21
<212> TYPE: DNA
<213> ORGANISM: homo sapiens

<400> SEQUENCE: 864
cgaccuauaa gaagccuuat t                                              21

<210> SEQ ID NO 865
<211> LENGTH: 21
```

```
<212> TYPE: DNA
<213> ORGANISM: homo sapiens

<400> SEQUENCE: 865
gcggcgaaug gaucuuugat t                                              21

<210> SEQ ID NO 866
<211> LENGTH: 21
<212> TYPE: DNA
<213> ORGANISM: homo sapiens

<400> SEQUENCE: 866
cggagcacua ccucaucaat t                                              21

<210> SEQ ID NO 867
<211> LENGTH: 21
<212> TYPE: DNA
<213> ORGANISM: homo sapiens

<400> SEQUENCE: 867
agcggaugag cgucauaaat t                                              21

<210> SEQ ID NO 868
<211> LENGTH: 21
<212> TYPE: DNA
<213> ORGANISM: homo sapiens

<400> SEQUENCE: 868
ccaacguguc cuacaaauat t                                              21

<210> SEQ ID NO 869
<211> LENGTH: 21
<212> TYPE: DNA
<213> ORGANISM: homo sapiens

<400> SEQUENCE: 869
cgugaaccuc ggcaggguat t                                              21

<210> SEQ ID NO 870
<211> LENGTH: 21
<212> TYPE: DNA
<213> ORGANISM: homo sapiens

<400> SEQUENCE: 870
guuugagugu gcucagauat t                                              21

<210> SEQ ID NO 871
<211> LENGTH: 21
<212> TYPE: DNA
<213> ORGANISM: homo sapiens

<400> SEQUENCE: 871
gaauugaccu guacaaagat t                                              21

<210> SEQ ID NO 872
<211> LENGTH: 21
<212> TYPE: DNA
<213> ORGANISM: homo sapiens

<400> SEQUENCE: 872
cgauaccucu caagucaaat t                                              21

<210> SEQ ID NO 873
<211> LENGTH: 21
```

```
<212> TYPE: DNA
<213> ORGANISM: homo sapiens

<400> SEQUENCE: 873
aauucgucca gaaacacaat t                                              21

<210> SEQ ID NO 874
<211> LENGTH: 21
<212> TYPE: DNA
<213> ORGANISM: homo sapiens

<400> SEQUENCE: 874
gugaggaaug gaagcucuat t                                              21

<210> SEQ ID NO 875
<211> LENGTH: 21
<212> TYPE: DNA
<213> ORGANISM: homo sapiens

<400> SEQUENCE: 875
gcagcgagag ccaagugaat t                                              21

<210> SEQ ID NO 876
<211> LENGTH: 21
<212> TYPE: DNA
<213> ORGANISM: homo sapiens

<400> SEQUENCE: 876
cauagauauc ggccggguat t                                              21

<210> SEQ ID NO 877
<211> LENGTH: 21
<212> TYPE: DNA
<213> ORGANISM: homo sapiens

<400> SEQUENCE: 877
ggccagucgg aauugagaat t                                              21

<210> SEQ ID NO 878
<211> LENGTH: 21
<212> TYPE: DNA
<213> ORGANISM: homo sapiens

<400> SEQUENCE: 878
aaucaacuuu acuguaauat t                                              21

<210> SEQ ID NO 879
<211> LENGTH: 21
<212> TYPE: DNA
<213> ORGANISM: homo sapiens

<400> SEQUENCE: 879
cggaauacgc cuguguuaat t                                              21

<210> SEQ ID NO 880
<211> LENGTH: 21
<212> TYPE: DNA
<213> ORGANISM: homo sapiens

<400> SEQUENCE: 880
gggcguacag agcacauuut t                                              21

<210> SEQ ID NO 881
<211> LENGTH: 21
```

```
<212> TYPE: DNA
<213> ORGANISM: homo sapiens

<400> SEQUENCE: 881
cggacaagca uuucaacuat t                                              21

<210> SEQ ID NO 882
<211> LENGTH: 21
<212> TYPE: DNA
<213> ORGANISM: homo sapiens

<400> SEQUENCE: 882
cggcgugcuc uggagccaat t                                              21

<210> SEQ ID NO 883
<211> LENGTH: 21
<212> TYPE: DNA
<213> ORGANISM: homo sapiens

<400> SEQUENCE: 883
gaguugaggu gucagagaat t                                              21

<210> SEQ ID NO 884
<211> LENGTH: 21
<212> TYPE: DNA
<213> ORGANISM: homo sapiens

<400> SEQUENCE: 884
guuugaucug agcuccuuat t                                              21

<210> SEQ ID NO 885
<211> LENGTH: 21
<212> TYPE: DNA
<213> ORGANISM: homo sapiens

<400> SEQUENCE: 885
cgaucugacu gaauguucat t                                              21

<210> SEQ ID NO 886
<211> LENGTH: 21
<212> TYPE: DNA
<213> ORGANISM: homo sapiens

<400> SEQUENCE: 886
aacggagucu cguacuauat t                                              21

<210> SEQ ID NO 887
<211> LENGTH: 21
<212> TYPE: DNA
<213> ORGANISM: homo sapiens

<400> SEQUENCE: 887
cggacacuuc ucuauucaut t                                              21

<210> SEQ ID NO 888
<211> LENGTH: 21
<212> TYPE: DNA
<213> ORGANISM: homo sapiens

<400> SEQUENCE: 888
ccaccuuuac ugugcuuaut t                                              21

<210> SEQ ID NO 889
<211> LENGTH: 21
```

```
<212> TYPE: DNA
<213> ORGANISM: homo sapiens

<400> SEQUENCE: 889
ggaacgccua agcuguuaat t                                              21

<210> SEQ ID NO 890
<211> LENGTH: 21
<212> TYPE: DNA
<213> ORGANISM: homo sapiens

<400> SEQUENCE: 890
gguaacgaug ggaaaggaat t                                              21

<210> SEQ ID NO 891
<211> LENGTH: 21
<212> TYPE: DNA
<213> ORGANISM: homo sapiens

<400> SEQUENCE: 891
cccugauuuc uacaucaaut t                                              21

<210> SEQ ID NO 892
<211> LENGTH: 21
<212> TYPE: DNA
<213> ORGANISM: homo sapiens

<400> SEQUENCE: 892
cguggaggaa auacuacaut t                                              21

<210> SEQ ID NO 893
<211> LENGTH: 21
<212> TYPE: DNA
<213> ORGANISM: homo sapiens

<400> SEQUENCE: 893
gaccuauaag aagccuuaat t                                              21

<210> SEQ ID NO 894
<211> LENGTH: 21
<212> TYPE: DNA
<213> ORGANISM: homo sapiens

<400> SEQUENCE: 894
ggagcacuac cucaucaaut t                                              21

<210> SEQ ID NO 895
<211> LENGTH: 21
<212> TYPE: DNA
<213> ORGANISM: homo sapiens

<400> SEQUENCE: 895
ggagguucau ccuauauuut t                                              21

<210> SEQ ID NO 896
<211> LENGTH: 21
<212> TYPE: DNA
<213> ORGANISM: homo sapiens

<400> SEQUENCE: 896
agcggagguu cauccuauat t                                              21

<210> SEQ ID NO 897
<211> LENGTH: 21
```

-continued

```
<212> TYPE: DNA
<213> ORGANISM: homo sapiens

<400> SEQUENCE: 897
guguccuaca aauacucaat t                                              21

<210> SEQ ID NO 898
<211> LENGTH: 21
<212> TYPE: DNA
<213> ORGANISM: homo sapiens

<400> SEQUENCE: 898
guuccaacgu guccuacaat t                                              21

<210> SEQ ID NO 899
<211> LENGTH: 21
<212> TYPE: DNA
<213> ORGANISM: homo sapiens

<400> SEQUENCE: 899
ggcuugcucu auaagggaut t                                              21

<210> SEQ ID NO 900
<211> LENGTH: 21
<212> TYPE: DNA
<213> ORGANISM: homo sapiens

<400> SEQUENCE: 900
ccaccaggau cacguuugat t                                              21

<210> SEQ ID NO 901
<211> LENGTH: 21
<212> TYPE: DNA
<213> ORGANISM: homo sapiens

<400> SEQUENCE: 901
ucgaaguacu cagcguaagt t                                              21

<210> SEQ ID NO 902
<211> LENGTH: 21
<212> TYPE: DNA
<213> ORGANISM: homo sapiens

<400> SEQUENCE: 902
cuuacgcuga guacuucgat t                                              21

<210> SEQ ID NO 903
<211> LENGTH: 21
<212> TYPE: DNA
<213> ORGANISM: homo sapiens

<400> SEQUENCE: 903
cuuacgcuga guacuucgat t                                              21

<210> SEQ ID NO 904
<211> LENGTH: 21
<212> TYPE: DNA
<213> ORGANISM: homo sapiens

<400> SEQUENCE: 904
ucgaaguacu cagcguaagt t                                              21

<210> SEQ ID NO 905
<211> LENGTH: 19
```

```
<212> TYPE: DNA
<213> ORGANISM: homo sapiens

<400> SEQUENCE: 905
ucgaaguacu cagcguaag                                          19

<210> SEQ ID NO 906
<211> LENGTH: 19
<212> TYPE: DNA
<213> ORGANISM: homo sapiens

<400> SEQUENCE: 906
cuuacgcuga guacuucga                                          19

<210> SEQ ID NO 907
<211> LENGTH: 19
<212> TYPE: DNA
<213> ORGANISM: homo sapiens

<400> SEQUENCE: 907
ucgaaguacu cagcguaag                                          19

<210> SEQ ID NO 908
<211> LENGTH: 19
<212> TYPE: DNA
<213> ORGANISM: homo sapiens

<400> SEQUENCE: 908
cuuacgcuga guacuucga                                          19

<210> SEQ ID NO 909
<211> LENGTH: 21
<212> TYPE: DNA
<213> ORGANISM: homo sapiens

<400> SEQUENCE: 909
uugagguuug aaaucgaccc t                                       21

<210> SEQ ID NO 910
<211> LENGTH: 21
<212> TYPE: DNA
<213> ORGANISM: homo sapiens

<400> SEQUENCE: 910
ggucgauuuc aaaccucaat t                                       21

<210> SEQ ID NO 911
<211> LENGTH: 23
<212> TYPE: DNA
<213> ORGANISM: homo sapiens

<400> SEQUENCE: 911
uaauuuguuc cugucuuccd adg                                     23

<210> SEQ ID NO 912
<211> LENGTH: 21
<212> TYPE: DNA
<213> ORGANISM: homo sapiens

<400> SEQUENCE: 912
ggaagacagg aacaaauuat t                                       21

<210> SEQ ID NO 913
<211> LENGTH: 21
```

```
<212> TYPE: DNA
<213> ORGANISM: homo sapiens

<400> SEQUENCE: 913
acgugacacg uucggagaat t                                           21

<210> SEQ ID NO 914
<211> LENGTH: 21
<212> TYPE: DNA
<213> ORGANISM: homo sapiens

<400> SEQUENCE: 914
uucuccgaac gugucacgut t                                           21

<210> SEQ ID NO 915
<211> LENGTH: 19
<212> TYPE: DNA
<213> ORGANISM: homo sapiens

<400> SEQUENCE: 915
uugagguuug aaaucgacc                                              19

<210> SEQ ID NO 916
<211> LENGTH: 19
<212> TYPE: DNA
<213> ORGANISM: homo sapiens

<400> SEQUENCE: 916
ggucgauuuc aaaccucaa                                              19

<210> SEQ ID NO 917
<211> LENGTH: 19
<212> TYPE: DNA
<213> ORGANISM: homo sapiens

<400> SEQUENCE: 917
uaauuuguuc cugucuucc                                              19

<210> SEQ ID NO 918
<211> LENGTH: 19
<212> TYPE: DNA
<213> ORGANISM: homo sapiens

<400> SEQUENCE: 918
ggaagacagg aacaaauua                                              19

<210> SEQ ID NO 919
<211> LENGTH: 19
<212> TYPE: DNA
<213> ORGANISM: homo sapiens

<400> SEQUENCE: 919
acgugacacg uucggagaa                                              19

<210> SEQ ID NO 920
<211> LENGTH: 19
<212> TYPE: DNA
<213> ORGANISM: homo sapiens

<400> SEQUENCE: 920
uucuccgaac gugucacgu                                              19

<210> SEQ ID NO 921
<211> LENGTH: 19
```

```
<212> TYPE: DNA
<213> ORGANISM: homo sapiens

<400> SEQUENCE: 921
uugagguuug aaaucgacc                                                19

<210> SEQ ID NO 922
<211> LENGTH: 19
<212> TYPE: DNA
<213> ORGANISM: homo sapiens

<400> SEQUENCE: 922
ggucgauuuc aaaccucaa                                                19

<210> SEQ ID NO 923
<211> LENGTH: 19
<212> TYPE: DNA
<213> ORGANISM: homo sapiens

<400> SEQUENCE: 923
uaauuuguuc cugucuucc                                                19

<210> SEQ ID NO 924
<211> LENGTH: 19
<212> TYPE: DNA
<213> ORGANISM: homo sapiens

<400> SEQUENCE: 924
ggaagacagg aacaaauua                                                19

<210> SEQ ID NO 925
<211> LENGTH: 19
<212> TYPE: DNA
<213> ORGANISM: homo sapiens

<400> SEQUENCE: 925
uucuucuuua auuaacacc                                                19

<210> SEQ ID NO 926
<211> LENGTH: 19
<212> TYPE: DNA
<213> ORGANISM: homo sapiens

<400> SEQUENCE: 926
gguguuaauu aaagaagaa                                                19

<210> SEQ ID NO 927
<211> LENGTH: 19
<212> TYPE: DNA
<213> ORGANISM: homo sapiens

<400> SEQUENCE: 927
ucugaguuug uaaauaucg                                                19

<210> SEQ ID NO 928
<211> LENGTH: 19
<212> TYPE: DNA
<213> ORGANISM: homo sapiens

<400> SEQUENCE: 928
cgauauuuac aaacucaga                                                19

<210> SEQ ID NO 929
<211> LENGTH: 19
```

```
<212> TYPE: DNA
<213> ORGANISM: homo sapiens

<400> SEQUENCE: 929
acgugacacg uucggagaa                                              19

<210> SEQ ID NO 930
<211> LENGTH: 19
<212> TYPE: DNA
<213> ORGANISM: homo sapiens

<400> SEQUENCE: 930
uucuccgaac gugucacgt                                              19
```

SHORT INTERFERING RIBONUCLEIC ACID (SIRNA) FOR ORAL ADMINISTRATION

PRIORITY INFORMATION

This U.S. divisional application claims priority U.S. PCT application Ser. No. 12/299,396, filed 2 May 2007, which claims priority to PCT Application Serial No. PCT/EP07/003867, filed 2 May 2007, which claims priority to GB Application Serial No. 0608838.9, filed 4 May 2006, the contents of which are incorporated herein by reference in their entirety.

BACKGROUND

RNA interference initially discovered in plants as Post-Transcriptional Gene Silencing (PTGS), is a highly conserved mechanism triggered by double-stranded RNA (dsRNA) and able to down regulate transcript of genes homologous to the dsRNA[1]. The dsRNA is first processed by Dicer into short duplexes of 21-23 nt, called short interfering RNAs (siRNAs)[2]. Incorporated in RNA-induced silencing complex (RISC) they are able to mediate gene silencing through cleavage of the target mRNA in the center of the region of homology by Argonaute 2, a component of RISC[3]. In 2001, Elbashir et al[4] demonstrated that the direct introduction of synthetic siRNAs would mediate RNA interference gene silencing in *drosophila* but also in mammalian cells. Since then, siRNA-mediated gene silencing has become a powerful and widely-used molecular biology tool in both target identification target validation studies. Use of siRNAs for gene silencing in animal studies has been described in a limited amount of animal models. Unmodified siRNAs were delivered locally in the eye[5], intrathecally or intracerebrally in the central nervous system[6], and intranasally for the inhibition of respiratory viruses[7]. Intravenous hydrodynamic tail vein injection of unmodified siRNAs has also been studied. This approach allows a rapid delivery, mainly to the liver[8]. A very limited number of studies have been reported on the systemic administration of unmodified siRNAs. Duxbury et al[9] administered intravenously unmodified siRNAs targeting Focal Adhesion Kinase to an orthotopic tumor xenograft mice model, and observed a tumor growth inhibition as well as a chemosensitization to gemcitabine. Soutscheck et al reported the systemic use of highly chemically modified siRNAs for the endogeneous silencing Apolipoprotein B. Intraperitoneal administration of most anti-ApoB siRNA at the high dose of 50 mg/kg reduced ApoB protein level and Lipoprotein concentration[10]. Despite these examples, in vivo use of siRNAs upon systemic delivery requires improvements in order to make this technology widely applicable for target validation or therapeutic applications. Indeed, unmodified siRNAs are subject to enzymatic digestion, mainly by nucleases abundant in the blood stream. In order to improve pharmacological properties of siRNAs several groups investigated chemical modification of these reagents. While the approaches described are very different among themselves and that no systematic study was yet performed, an overview of the results allows to determine the tolerance of siRNAs to chemical modifications. Several chemistries such as phosphorothioates[11] or boranophosphates[12], 2'-O-Methyl[13], 2'-O-allyl[14], 2'-methoxyethyl (MOE) and 2'-deoxyfluoronucleotides[15] or Locked Nucleic Acids (LNA)[16] have been investigated. These studies highlighted that tolerance for modification is not only chemistry-dependent, but also position-dependent.

The present invention provides a minimally modified siRNA with improved pharmacological properties. The minimally modified siRNAs are 19 bp double-stranded RNA modified on the 3'-end of each strand in order to prevent 3'-exonuclease digestion: the 3'-dideoxynucleotide overhang of 21-nt siRNA has been replaced by a universal 3'-hydroxypropyl phosphodiester moiety and the modification of the two first base-pairing nucleotides on 3'-end of each strand further enhances serum stability. Applied intraperitoneally or orally to adult mice, the modified siRNAs displayed higher potency in a growth factor induce angiogenesis model which correlates with their increased serum stability.

SUMMARY

In one aspect, the present invention provides a short interfering ribonucleic acid (siRNA) for oral administration, said siRNA comprising two separate RNA strands that are complementary to each other over at least 15 nucleotides, wherein each strand is 49 nucleotides or less, and wherein at least one of which strands contains at least one chemical modification.

In one embodiment, the siRNA comprises at least one modified nucleotide.

In another embodiment, the siRNA comprises at least one 3' end cap.

In another embodiment, said modified nucleotide is selected from among 2' alkoxyribonucleotide, 2' alkoxyalkoxy ribonucleotide, a locked nucleic acid ribonucleotide (LNA), 2'-fluoro ribonucleotide, morpholino nucleotide.

In another embodiment, said modified nucleotide is selected from among nucleotides having a modified internucleoside linkage selected from among phosphorothioate, phosphorodithioate, phosphoramidate, boranophosphonoate, and amide linkages.

In another embodiment, said two RNA strands are fully complementary to each other.

In another embodiment, said siRNA comprises a 1 to 6 nucleotide overhang on at least one of the 5' end or 3' end.

In another embodiment, the siRNA contains at least one 3' cap, which is chemical moiety conjugated to the 3' end via the 3' carbon and is selected from among compounds of Formula I:

[Formula I]

wherein

X is O or S $R_1$ and $R_2$ are independently OH, $NH_2$, SH, alkyl, aryl, alkyl-aryl, aryl-alkyl, where alkyl, aryl, alkyl-aryl, aryl-alkyl can be substituted by additional heteroatoms and functional groups, preferably a heteroatom selected from the group of N, O, or S or a functional group selected from the group OH, $NH_2$, SH, carboxylic acid or ester;

or $R_1$ and $R_2$ may be of formula Y—Z where Y is O, N, S and Z is H, alkyl, aryl, alkyl-aryl, aryl-alkyl, where alkyl, aryl, alkyl-aryl, aryl-alkyl can be substituted by additional heteroatoms, preferably a heteroatom selected from the group of N, O, or S.

In another embodiment, the siRNA contains at least one strand which is complementary over at least 15 nucleotides to the mRNA or pre-mRNA of VEGFR-1, VEGFR-2, VEGFR3, Tie2, bFGFR, IL8RA, IL8RB, Fas, or IGF2R.

In another embodiment, the siRNA contains at least one strand which comprises a sequence selected from SEQ ID NO 1-900.

In another embodiment, the siRNA is chosen from the group consisting of SEQ ID NO 901-930.

In another embodiment, the siRNA has a stability in a standard gastric acid assay that is greater than an unmodified siRNA with the same nucleotide sequence.

In another embodiment, the siRNA has a stability in a standard gastric acid assay that is greater than or equal to 50% after 30 minutes exposure.

In another embodiment, the siRNA has a stability in a standard serum assay greater than unmodified siRNA.

In another embodiment, the siRNA has a stability in a standard serum assay that is greater than or equal to 50% after 30 minutes exposure.

In another embodiment, the siRNA has a stability in a standard intestinal lavage assay that is greater than unmodified siRNA.

In another embodiment, the siRNA has an enhanced oral bioavailability compared to an unmodified siRNA of the same nucleotide sequence.

In one aspect, the invention provides a pharmaceutical composition comprising an siRNA with any one or more of the above properties.

In another aspect, the invention provides an siRNA with any one or more of the above properties for use as a medicament.

In another aspect, the invention provides the use of an siRNA with any one or more of the above properties in the preparation of a medicament for treating an angiogenic disorder.

In another aspect, the invention provides the use of an siRNA with any one or more of the above properties to inhibit an angiogenic process in vitro.

BRIEF DESCRIPTION OF THE DRAWINGS

FIGS. 1a, 1b, 1c, 1d and 1e: Metabolic degradation of unmodified siRNA pG13-siRNA (wild-type siRNA in mouse serum); a-c) Ion Exchange-HPLC analysis of unmodified siRNAs after incubation in mouse serum for 0', 30' and 180'; After 30' of incubation at 37° C., major peak in the Ion Exchange HPLC was isolated and re-injected in LC-MS, d) table of detected molecular weights and their assignments; e) ESI-MS spectrum

FIG. 7: Characterization in cellulo of 3 formats of anti-VEGFR2 siRNA (2 independent sequences). Wild-type siRNA, C3-siRNA and C3-MOE siRNA were transfected into MS1 cells at three concentrations (1, 5, 10 nM). Silencing potency was assessed by measuring VEGFR2 cell surface level by FACS.

FIG. 8a shows the results of controls, unmodified VEGFR2 siRNA and C3 modified VEGFR2 siRNA at 1, 5 and 25 micrograms per mouse per day. FIG. 8b shows controls, C3 modified VEGFR2 siRNA and of C3-MOE VEGFR2 siRNA at 0.2, 1 and 5 micrograms per mouse per day. In each case pools of 2 anti-VEGFR2 siRNAs were given daily intraperitoneally for three days.

FIG. 9: In vivo testing of anti-VEGFR2 C3-MOE siRNA given intraperitoneally (i.p.) in a B16 homograft melanoma tumor mouse model at 5 and 20 micrograms per mouse per day.

FIG. 11: In vivo testing of C3-MOE siRNA in a growth factor induced angiogenesis mouse model. anti-Tie2 siRNAs were given daily intraperitoneally (1 and 0.2 micrograms per mouse per day) or orally (20 and 5 micrograms per mouse per day) for three days.

DETAILED DISCLOSURE OF THE INVENTION

Figure 1A:
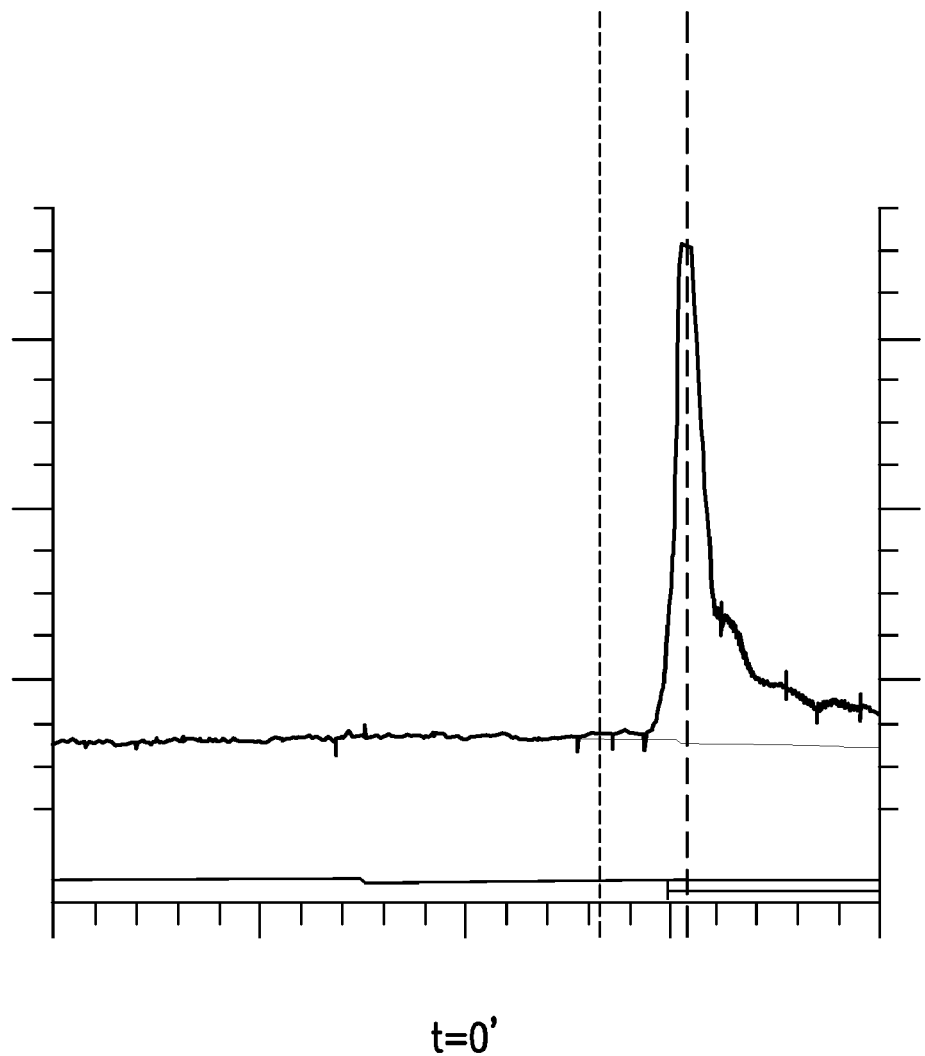

The present invention relates to compositions and methods for treating angiogenic disorders in a mammal. Specifically, the invention relates to small-interfering RNA ("siRNA") which may be used to treat angiogenic disorders upon oral administration to a mammal.

Angiogenesis targets in vascular endothelial cells include the following targets/genes: VEGFR-1 (GenBank Accession #AF06365); VEGFR-2 (GenBank Accession #AF063658); VEGFR-3 (GenBank Accession #(NM_002020); Tie2 (TEK) (GenBank Accession #NM_000459); bFGFR (GenBank Accession #M60485); IL8RA (GenBank Accession #L19591); IL8RB (GenBank Accession #L19593); Fas (GenBank Accession #X89101); IGF2R (GenBank Accession #NM_000876).

The siRNA molecules according to the present invention mediate RNA interference ("RNAi"). The term "RNAi" is well known in the art and is commonly understood to mean the inhibition of one or more target genes in a cell by siRNA with a region which is complementary to the target gene. Various assays are known in the art to test siRNA for its ability to mediate RNAi (see for instance Elbashir et al., Methods 26 (2002), 199-213). The effect of the siRNA according to the present invention on gene expression will typically result in expression of the target gene being inhibited by at least 10%, 33%, 50%, 90%, 95% or 99% when compared to a cell not treated with the RNA molecules according to the present invention.

"siRNA" or "small-interfering ribonucleic acid" according to the invention has the meanings known in the art, including the following aspects. The siRNA consists of two strands of ribonucleotides which hybridize along a complementary region under physiological conditions. The strands are separate but they may be joined by a molecular linker in certain embodiments. The individual ribonucleotides may be unmodified naturally occurring ribonucleotides, unmodified naturally occurring deoxyribonucleotides or they may be chemically modified or synthetic as described elsewhere herein.

The siRNA molecules in accordance with the present invention comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. In an embodiment, the RNA molecules of the present invention specifically target one given gene. In order to only target the desired mRNA, the siRNA reagent may have 100% homology to the target mRNA and at least 2 mismatched nucleotides to all other genes present in the cell or organism. Methods to analyze and identify siRNAs with sufficient sequence identity in order to effectively inhibit expression of a specific target sequence are known in the art. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group).

Another factor affecting the efficiency of the RNAi reagent is the target region of the target gene. The region of a target gene effective for inhibition by the RNAi reagent may be determined by experimentation. A suitable mRNA target region would be the coding region. Also suitable are untranslated regions, such as the 5'-UTR, the 3'-UTR, and splice junctions. For instance, transfection assays as described in Elbashir S. M. et al, 2001 EMBO J., 20, 6877-6888 may be performed for this purpose. A number of other suitable assays and methods exist in the art which are well known to the skilled person.

The length of the region of the siRNA complementary to the target, in accordance with the present invention, may be from 10 to 100 nucleotides, 12 to 25 nucleotides, 14 to 22 nucleotides or 15, 16, 17 or 18 nucleotides. Where there are mismatches to the corresponding target region, the length of the complementary region is generally required to be somewhat longer.

Because the siRNA may carry overhanging ends (which may or may not be complementary to the target), or additional nucleotides complementary to itself but not the target gene, the total length of each separate strand of siRNA may be 10 to 100 nucleotides, 15 to 49 nucleotides, 17 to 30 nucleotides or 19 to 25 nucleotides.

The phrase "each strand is 49 nucleotides or less" means the total number of consecutive nucleotides in the strand, including all modified or unmodified nucleotides, but not including any chemical moieties which may be added to the 3' or 5' end of the strand. Short chemical moieties inserted into the strand are not counted, but a chemical linker designed to join two separate strands is not considered to create consecutive nucleotides.

The phrase "a 1 to 6 nucleotide overhang on at least one of the 5' end or 3' end" refers to the architecture of the complementary siRNA that forms from two separate strands under physiological conditions. If the terminal nucleotides are part of the double-stranded region of the siRNA, the siRNA is considered blunt ended. If one or more nucleotides are unpaired on an end, an overhang is created. The overhang length is measured by the number of overhanging nucleotides. The overhanging nucleotides can be either on the 5' end or 3' end of either strand.

The siRNA according to the present invention confer a high in vivo stability suitable for oral delivery by including at least one modified nucleotide in at least one of the strands. Thus the siRNA according to the present invention contains at least one modified or non-natural ribonucleotide. A lengthy description of many known chemical modifications are set out in published PCT patent application WO 200370918 and will not be repeated here. Suitable modifications for oral delivery are more specifically set out in the Examples and description herein. Suitable modifications include, but are not limited to modifications to the sugar moiety (i.e. the 2' position of the sugar moiety, such as for instance 2'-O-(2-methoxyethyl) or 2'-MOE) (Martin et al., Helv. Chim. Acta, 1995, 78, 486-504) i.e., an alkoxyalkoxy group) or the base moiety (i.e. a nonnatural or modified base which maintains ability to pair with another specific base in an alternate nucleotide chain). Other modifications include so-called 'backbone' modifications including, but not limited to, replacing the phosphoester group (connecting adjacent ribonucleotides with for instance phosphorothioates, chiral phosphorothioates or phosphorodithioates). Finally, end modifications sometimes referred to herein as 3' caps or 5' caps may be of significance. As illustrated in Table 1, caps may consist of simply adding additional nucleotides, such as "T-T" which has been found to confer stability on an siRNA. Caps may consist of more complex chemistries which are known to those skilled in the art.

In an embodiment used in the Examples below, the 3' cap is a chemical moiety conjugated to the 3' end via the 3' carbon and is selected from among compounds of Formula I.

[Formula I]

wherein
X is O or S
$R_1$ and $R_2$ are independently OH, $NH_2$, SH, alkyl, aryl, alkyl-aryl, aryl-alkyl, where alkyl, aryl, alkyl-aryl, aryl-alkyl can be substituted by additional heteroatoms and functional groups, preferably a heteroatom selected from the group of N, O, or S or a functional group selected from the group OH, $NH_2$, SH, carboxylic acid or ester;
or $R_1$ and $R_2$ may be of formula Y—Z where Y is O, N, S and Z is H, alkyl, aryl, alkyl-aryl, aryl-alkyl, where alkyl, aryl, alkyl-aryl, aryl-alkyl can be substituted by additional heteroatoms, preferably a heteroatom selected from the group of N, O, or S.

Examples of modifications on the sugar moiety include 2' alkoxyribonucleotide, 2' alkoxyalkoxy ribonucleotide, locked nucleic acid ribonucleotide (LNA), 2'-fluoro ribonucleotide, morpholino nucleotide.

The internucleoside linkage may also be modified. Examples of internucleoside linkage include phosphorothioate, phosphorodithioate, phosphoramidate, and amide linkages.

$R_1$ may be OH.

$R_1$ and $R_2$ together may comprise from 1 to 24 C-atoms, from 1 to 12 C-atoms, from 2 to 10 C-atoms, from 1 to 8 or from 2 to 6 C-atoms. In another embodiment, $R_1$ and $R_2$ are independently OH, lower alkyl, lower aryl, lower alkyl-aryl, lower aryl-alkyl, where lower alkyl, lower aryl, lower alkyl-aryl, lower aryl-alkyl can be substituted by additional heteroatoms and functional groups as defined above. In another embodiment, $R_1$ and $R_2$ are not both OH.

The term "lower" in connection with organic radicals or compounds means a compound or radical which may be branched or unbranched with up to and including 7 carbon atoms, preferably 1-4 carbon atoms. Lower alkyl represents, for example, methyl, ethyl, n-propyl, isopropyl, n-butyl, sec-butyl, tert-butyl, n-pentyl and branched pentyl, n-hexyl and branched hexyl.

Examples of alkoxys include O-Met, O-Eth, O-prop, O-but, O-pent, O-hex.

Methods for the synthesis of siRNA, including siRNA containing at least one modified or non-natural ribonucleotides are well known and readily available to those of skill in the art. For example, a variety of synthetic chemistries are set out in published PCT patent applications WO2005021749 and WO200370918, both incorporated herein by reference. The reaction may be carried out in solution or, preferably, on solid phase or by using polymer supported reagents, followed by combining the synthesized RNA strands under conditions, wherein a siRNA molecule is formed, which is capable of mediating RNAi.

The present invention provides an siRNA containing at least one modified nucleotide which is suitable for oral delivery. In functional terms this means siRNA will have suitable pharmacokinetics and biodistribution upon oral administration to achieve delivery to the target tissue of concern. In particular this requires serum stability, lack of immune response, and drug like behaviour. Many of these features of siRNA can be anticipated based on the standard gastric acid assays and standard serum assays disclosed elsewhere herein.

In another aspect, the present invention provides methods for the inhibition of a target gene comprising introducing into a cell and siRNA according to the present invention, which is capable of inhibiting at least one target gene by RNAi. Also, more than one species of siRNA, which are each specific for another target region, may be introduced into a cell at the same time or sequentially.

The present invention is not limited to any type of target gene or nucleotide sequence. For example, the target gene can be a cellular gene, an endogenous gene, a pathogen-associated gene, a viral gene or an oncogene. Angiogenic genes are of particular importance to the invention because some of the Examples highlight that the orally delivered siRNA of the invention may accumulate at sites of vasculogenesis, neovascularization or angiogenesis. An updated listing of angiogenic genes at these sites of particular interest for the invention are listed in AngioDB: database of angiogenesis and angiogenesis-related molecules Tae-Kwon Sohn, Eun-Joung Moon1, Seok-Ki Lee1, Hwan-Gue Cho2 and Kyu-Won Kim3, Nucleic Acids Research, 2002, Vol. 30, No. 1 369-371 and online at http://angiodb.snu.ac.kr/. Genes of particular significance have been analyzed in detail and are set out elsewhere herein.

In another aspect, the invention also provides a kit comprising reagents for inhibiting expression of a target gene in a cell, wherein said kit comprises dsRNA according to the present invention. The kit comprises at least one of the reagents necessary to carry out the in vitro or in vivo introduction of the dsRNA according to the present invention to test samples or subjects. In a preferred embodiment, such kits also comprise instructions detailing the procedures by which the kit components are to be used.

"Treatment of an angiogenic disorder" as used in this disclosure means use of a modified siRNA of the invention in a pharmaceutical composition for the treatment of diseases involving the physiological and pathological processes of neovascularization, vasculogenesis and/or angiogenesis. As such, these pharmaceutical compositions are useful for treating diseases, conditions and disorders that require inhibition of neovascularization, vasculogenesis or angiogenesis, including but not limited to cancer tumour growth and metastasis, neoplasm, ocular neovascularization (including macular degeneration, diabetic retinopathy, ischemic retinopathy, retinopathy of prematurity, choroidal neovascularization), rheumatoid arthritis, osteoarthritis, chronic asthma, septic shock, inflammatory diseases, synovitis, bone and cartilage destruction, pannus growth, osteophyte formation, osteomyelitis, psoriasis, obesity, haemangioma, Kaposi's sarcoma, atherosclerosis (including atherosclerotic plaque rupture), endometriosis, warts, excess hair growth, scar keloids, allergic oedema, dysfunctional uterine bleeding, follicular cysts, ovarian hyperstimulation, endometriosis, osteomyelitis, inflammatory and infectious processes (hepatitis, pneumonia, glumerulonephtritis), asthma, nasal polyps, transplantation, liver regeneration, leukomalacia, thyroiditis, thyroid enlargement, lymphoproliferative disorders, haematologic malignancies, vascular malformations, and pre-eclampsia.

As used herein, "treatment" means an action taken to inhibit or reduce a process of a disease, disorder or condition, to inhibit or reduce a symptom of a disease, disorder or condition, or to prophylactically prevent the onset or further development of a disease, disorder or condition. "Treat" is the cognitive verb thereof.

An effective dose of the therapeutic agent of the invention is that dose required to treat a disease state. The effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of siRNA is administered dependent upon potency. The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, intraperitoneal, or intrathecal injection, or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in a mixture with excipients suitable for the manufacture of aqueous suspensions.

Oral administration of the compositions of the invention include all standard techniques for administering substances directly to the stomach or gut, most importantly by patient controlled swallowing of the dosage form, but also by other mechanical and assisted means of such delivery.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Therapeutic effect of the therapeutic agents of the invention may be enhanced by combination with other agents. Typically such other agents will include agents known for use in treating similar diseases, such as angiogenic disorders. Alternatively, such agents may be used to reduce side-effects or unwanted effects caused by the therapeutic agents of the invention.

The siRNA of the invention also have important research uses. One such study includes research into an angiogenic process in vitro. By "angiogenic process in vitro" is meant any process for studying angiogenesis or vasculogenesis which does not employ a whole animal. As such, in vitro or ex vivo methods and assays which study the steps of the angiogenic process using markers or indicators of angiogenesis are included hereby.

RNA Strand Nucleotide Sequences

The siRNA strand sequences identified in Table 1 have been identified as suitable siRNA sequences against the following targets: VEGFR-1 (GenBank Accession #AF06365); VEGFR-2 (GenBank Accession #AF063658); VEGFR-3 (GenBank Accession #(NM_002020); Tie2 (TEK) (GenBank Accession #NM_000459); bFGFR (GenBank Accession #M60485); IL8RA (GenBank Accession #L19591); IL8RB (GenBank Accession #L19593); Fas (GenBank Accession #X89101); IGF2R (GenBank Accession #NM_000876).

TABLE 1 siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
| --- | --- | --- | --- | --- | --- |
| VEGFR-1 | 1731 | UAUAAGAACUUGUUAACUGTG | 1 | CAGUUAACAAGUUCUUAUATT | 451 |
| VEGFR-1 | 1021 | UACGGUUUCAAGCACCUGCTG | 2 | GCAGGUGCUUGAAACCGUATT | 452 |
| VEGFR-1 | 1209 | UUUAUGCUCAGCAAGAUUGTA | 3 | CAAUCUUGCUGAGCAUAAATT | 453 |
| VEGFR-1 | 2904 | UUAUCUUCCUGAAAGCCGGAG | 4 | CCGGCUUUCAGGAAGAUAATT | 454 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| VEGFR-1 | 1363 | UUGAGGGAUACCAUAUGCGGT | 5 | CGCAUAUGGUAUCCCUCAATT | 455 |
| VEGFR-1 | 1158 | UUGAUAAUUAACGAGUAGCCA | 6 | GCUACUCGUUAAUUAUCAATT | 456 |
| VEGFR-1 | 1091 | UUAACCAUACAACUUCCGGCG | 7 | CCGGAAGUUGUAUGGUUAATT | 457 |
| VEGFR-1 | 471 | UUAGGUGACGUAACCCGGCAG | 8 | GCCGGGUUACGUCACCUAATT | 458 |
| VEGFR-1 | 2751 | UUGCUCUUGAGGUAGUUGGAG | 9 | CCAACUACCUCAAGAGCAATT | 459 |
| VEGFR-1 | 636 | UUUGUCUUAUACAAAUGCCCA | 10 | GGCAUUUGUAUAAGACAAATT | 460 |
| VEGFR-1 | 1254 | UUGACAAUUAGAGUGGCAGTG | 11 | CUGCCACUCUAAUUGUCAATT | 461 |
| VEGFR-1 | 2375 | UUAUAAUUGAUAGGUAGUCAG | 12 | GACUACCUAUCAAUUAUAATT | 462 |
| VEGFR-1 | 3536 | UUGAGUAUGUAAACCCACUAT | 13 | AGUGGGUUUACAUACUCAATT | 463 |
| VEGFR-1 | 2971 | UUCCAUAGUGAUGGGCUCCTT | 14 | GGAGCCCAUCACUAUGGAATT | 464 |
| VEGFR-1 | 1774 | UCUGUUAUUAACUGUCCGCAG | 15 | GCGGACAGUUAAUAACAGATT | 465 |
| VEGFR-1 | 3494 | UUGGGAUGUAGUCUUUACCAT | 16 | GGUAAAGACUACAUCCCAATT | 466 |
| VEGFR-1 | 2269 | UGUUAGAGUGAUCAGCUCCAG | 17 | GGAGCUGAUCACUCUAACATT | 467 |
| VEGFR-1 | 525 | UUUCCAUCAGGGAUCAAAGTG | 18 | CUUUGAUCCCUGAUGGAAATT | 468 |
| VEGFR-1 | 769 | UUGAACUCUCGUGUUCAAGGG | 19 | CUUGAACACGAGAGUUCAATT | 469 |
| VEGFR-1 | 2246 | UAGACUUGUCCGAGGUUCCTT | 20 | GGAACCUCGGACAAGUCUATT | 470 |
| VEGFR-1 | 732 | UUGAGGACAAGAGUAUGGCCT | 21 | GCCAUACUCUUGUCCUCAATT | 471 |
| VEGFR-1 | 3813 | UUACUGGUUACUCUCAAGUCA | 22 | ACUUGAGAGUAACCAGUAATT | 472 |
| VEGFR-1 | 3925 | UUCCAGCUCAGCUGGUCGTA | 23 | CGACCACGCUGAGCUGGAATT | 473 |
| VEGFR-1 | 1414 | UGCUUCGGAAUGAUUAUGGTT | 24 | CCAUAAUCAUUCCGAAGCATT | 474 |
| VEGFR-1 | 615 | UUGACUGUUGCUUCACAGGTC | 25 | CCUGUGAAGCAACAGUCAATT | 475 |
| VEGFR-1 | 3300 | UCAUCCAUUUGUACUCCUGGG | 26 | CAGGAGUACAAAUGGAUGATT | 476 |
| VEGFR-1 | 2845 | UGGUUUCUUGCCUUGUUCCAG | 27 | GGAACAAGGCAAGAAACCATT | 477 |
| VEGFR-1 | 2802 | UUAGGCUCCAUGUGUAGUGCT | 28 | CACUACACAUGGAGCCUAATT | 478 |
| VEGFR-1 | 1564 | UCUAGAGUCAGCCACAACCAA | 29 | GGUUGUGGCUGACUCUAGATT | 479 |
| VEGFR-1 | 1154 | UAAUUAACGAGUAGCCACGAG | 30 | CGUGGCUACUCGUUAAUUATT | 480 |
| VEGFR-1 | 1090 | UAACCAUACAACUUCCGGCGA | 31 | GCCGGAAGUUGUAUGGUUATT | 481 |
| VEGFR-1 | 1260 | UUCACAUUGACAAUUAGAGTG | 32 | CUCUAAUUGUCAAUGUGAATT | 482 |
| VEGFR-1 | 3530 | AUGUAAACCCACUAUUUCCTG | 33 | GGAAAUAGUGGGUUUACAUTT | 483 |
| VEGFR-1 | 1177 | AUCCUCUUCAGUUACGUCCTT | 34 | GGACGUAACUGAAGAGGAUTT | 484 |
| VEGFR-1 | 1193 | UUGUAUAAUUCCCUGCAUCCT | 35 | GAUGCAGGGAAUUAUACAATT | 485 |
| VEGFR-1 | 1092 | UUUAACCAUACAACUUCCGGC | 36 | CCGGAAGUUGUAUGGUUAAATT | 486 |
| VEGFR-1 | 627 | UACAAAUGCCCAUUGACUGTT | 37 | CAGUCAAUGGGCAUUUGUATT | 487 |
| VEGFR-1 | 474 | AUGUUAGGUGACGUAACCCGG | 38 | GGGUUACGUCACCUAACAUTT | 488 |
| VEGFR-1 | 2761 | UAAGUCACGUUUGCUCUUGAG | 39 | CAAGAGCAAACGUGACUUATT | 489 |
| VEGFR-1 | 2752 | UUUGCUCUUGAGGUAGUUGGA | 40 | CAACUACCUCAAGAGCAAATT | 490 |
| VEGFR-1 | 3516 | UUUCCUGUCAGUAUGGCAUTG | 41 | AUGCCAUACUGACAGGAAATT | 491 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| VEGFR-1 | 1790 | UACUGUAGUGCAUUGUUCUGT | 42 | AGAACAAUGCACUACAGUAUU | 492 |
| VEGFR-1 | 1155 | AUAAUUAACGAGUAGCCACGA | 43 | GUGGCUACUCGUUAAUUAUU | 493 |
| VEGFR-1 | 1370 | UUGUAGGUUGAGGGAUACCAT | 44 | GGUAUCCCUCAACCUACAAUU | 494 |
| VEGFR-1 | 2227 | UUGAACAGUGAGGUAUGCUGA | 45 | AGCAUACCUCACUGUUCAAUU | 495 |
| VEGFR-1 | 3481 | UUUACCAUCCUGUUGUACAUU | 46 | UGUACAACAGGAUGGUAAAUU | 496 |
| VEGFR-1 | 1261 | UUUCACAUUGACAAUUAGAGT | 47 | UCUAAUUGUCAAUGUGAAAUU | 497 |
| VEGFR-1 | 1791 | AUACUGUAGUGCAUUGUUCTG | 48 | GAACAAUGCACUACAGUAUU | 498 |
| VEGFR-1 | 3805 | UACUCUCAAGUCAAUCUUGAG | 49 | CAAGAUUGACUUGAGAGUAUU | 499 |
| VEGFR-1 | 2764 | AAAUAAGUCACGUUUGCUCTT | 50 | GAGCAAACGUGACUUAUUUUU | 500 |
| VEGFR-2 | 617 | UAAUAGACUGGUAACUUUCAT | 51 | GAAAGUUACCAGUCUAUUAUU | 501 |
| VEGFR-2 | 2686 | UAGAAGGUUGACCACAUUGAG | 52 | CAAUGUGGUCAACCUUCUAUU | 502 |
| VEGFR-2 | 561 | UAGCUGAUCAUGUAGCUGGGA | 53 | CCAGCUACAUGAUCAGCUAUU | 503 |
| VEGFR-2 | 525 | UUGCUGUCCCAGGAAAUUCTG | 54 | GAAUUUCCUGGGACAGCAAUU | 504 |
| VEGFR-2 | 2277 | AUGAUUUCCAAGUUCGUCUUT | 55 | AGACGAACUUGGAAAUCAUU | 505 |
| VEGFR-2 | 395 | UAAUGUACACGACUCCAUGTT | 56 | CAUGGAGUCGUGUACAUUAUU | 506 |
| VEGFR-2 | 2410 | UUCAUCUGGAUCCAUGACGAT | 57 | CGUCAUGGAUCCAGAUGAAUU | 507 |
| VEGFR-2 | 2007 | UGAUUCUCCAGGUUUCCUGTG | 58 | CAGGAAACCUGGAGAAUCAUU | 508 |
| VEGFR-2 | 1323 | UAGACCGUACAUGUCAGCGTT | 59 | CGCUGACAUGUACGGUCUAUU | 509 |
| VEGFR-2 | 3382 | UUCUGGUGUAGUAUAAUCAGG | 60 | UGAUUAUACUACACCAGAAUU | 510 |
| VEGFR-2 | 3078 | UUUCGUGCCGCCAGGUCCCTG | 61 | GGGACCUGGCGGCACGAAAUU | 511 |
| VEGFR-2 | 1432 | UUCUUCACAAGGGUAUGGGTT | 62 | CCCAUACCCUUGUGAAGAAUU | 512 |
| VEGFR-2 | 1817 | UCAAUUUCCAAAGAGUAUCCA | 63 | GAUACUCUUUGGAAAUUGAUU | 513 |
| VEGFR-2 | 688 | UAGUUCAAUUCCAUGAGACGG | 64 | GUCUCAUGGAAUUGAACUAUU | 514 |
| VEGFR-2 | 2310 | AACAUGGCAAUCACCGCCGTG | 65 | CGGCGGUGAUUGCCAUGUUUU | 515 |
| VEGFR-2 | 2130 | UCCUUCAAUACAAUGCCUGAG | 66 | CAGGCAUUGUAUUGAAGGAUU | 516 |
| VEGFR-2 | 799 | UACAAGUUUCUUAUGCUGATG | 67 | UCAGCAUAAGAAACUUGUAUU | 517 |
| VEGFR-2 | 3523 | UGAUAUCGGAAGAACAAUGTA | 68 | CAUUGUUCUUCCGAUAUCAUU | 518 |
| VEGFR-2 | 1843 | UGUGCUAUUAGAGAACAUGGT | 69 | CAUGUUCUCUAAUAGCACAUU | 519 |
| VEGFR-2 | 2941 | UUCUACAUCACUGAGGGACTT | 70 | GUCCCUCAGUGAUGUAGAAUU | 520 |
| VEGFR-2 | 2088 | UCUUUAAACCACAUGAUCUGT | 71 | AGAUCAUGUGGUUUAAAGAUU | 521 |
| VEGFR-2 | 472 | UCUUGCACAAAGUGACACGTT | 72 | CGUGUCACUUUGUGCAAGAUU | 522 |
| VEGFR-2 | 180 | UGAUUAUGGGCCAAAGCCAG | 73 | GGCUUUGGCCCAAUAAUCAUU | 523 |
| VEGFR-2 | 1568 | AUUUGUACAAAGCUGACACAT | 74 | GUGUCAGCUUUGUACAAAUU | 524 |
| VEGFR-2 | 3141 | UAAAUAUCCCGGGCCAAGCCA | 75 | GCUUGGCCCGGGAUAUUUAUU | 525 |
| VEGFR-2 | 3769 | AACCAUACCACUGUCCGUCTG | 76 | GACGGACAGUGGUAUGGUUUU | 526 |
| VEGFR-2 | 3920 | UGUCAUCGGAGUGAUAUCCGG | 77 | GGAUAUCACUCCGAUGACAUU | 527 |
| VEGFR-2 | 1718 | UCUCAAACGUAGAUCUGUCTG | 78 | GACAGAUCUACGUUUGAGAUU | 528 |
| VEGFR-2 | 2919 | UCCUCCACAAAUCCAGAGCTG | 79 | GCUCUGGAUUUGUGGAGGAUU | 529 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| VEGFR-2 | 324 | UAAAUGACCGAGGCCAAGUCA | 80 | ACUUGGCCUCGGUCAUUUATT | 530 |
| VEGFR-2 | 1050 | UAACCAAGGUACUUCGCAGGG | 81 | CUGCGAAGUACCUUGGUUATT | 531 |
| VEGFR-2 | 56 | UAGGCAAACCCACAGAGGCGG | 82 | GCCUCUGUGGGUUUGCCUATT | 532 |
| VEGFR-2 | 2453 | UGGCAUCAUAAGGCAGUCGTT | 83 | CGACUGCCUUAUGAUGCCATT | 533 |
| VEGFR-2 | 1303 | UUGAGUGGUGCCGUACUGGTA | 84 | CCAGUACGGCACCACUCAATT | 534 |
| VEGFR-2 | 1813 | UUUCCAAAGAGUAUCCAAGTT | 85 | CUUGGAUACUCUUUGGAAATT | 535 |
| VEGFR-2 | 2015 | UUGUCGUCUGAUUCUCCAGGT | 86 | CUGGAGAAUCAGACGACAATT | 536 |
| VEGFR-2 | 3088 | UAAGAGGAUAUUUCGUGCCGC | 87 | GGCACGAAAUAUCCUCUUATT | 537 |
| VEGFR-2 | 625 | UAUGUACAUAAUAGACUGGTA | 88 | CCAGUCUAUUAUGUACAUATT | 538 |
| VEGFR-2 | 800 | UUACAAGUUUCUUAUGCUGAT | 89 | CAGCAUAAGAAACUUGUAATT | 539 |
| VEGFR-2 | 811 | UAGGUCUCGGUUUACAAGUTT | 90 | ACUUGUAAACCGAGACCUATT | 540 |
| VEGFR-2 | 812 | UUAGGUCUCGGUUUACAAGTT | 91 | CUUGUAAACCGAGACCUAATT | 541 |
| VEGFR-2 | 3093 | UCCGAUAAGAGGAUAUUUCGT | 92 | GAAAUAUCCUCUUAUCGGATT | 542 |
| VEGFR-2 | 801 | UUUACAAGUUUCUUAUGCUGA | 93 | AGCAUAAGAAACUUGUAAATT | 543 |
| VEGFR-2 | 2009 | UCUGAUUCUCCAGGUUUCCTG | 94 | GGAAACCUGGAGAAUCAGATT | 544 |
| VEGFR-2 | 2127 | UUCAAUACAAUGCCUGAGUCT | 95 | ACUCAGGCAUUGUAUUGAATT | 545 |
| VEGFR-2 | 1585 | UUUGUUGACCGCUUCACAUTT | 96 | AUGUGAAGCGGUCAACAAATT | 546 |
| VEGFR-2 | 562 | AUAGCUGAUCAUGUAGCUGGG | 97 | CAGCUACAUGAUCAGCUAUTT | 547 |
| VEGFR-2 | 3906 | UAUCCGGACUGGUAGCCGCTT | 98 | GCGGCUACCAGUCCGGAUATT | 548 |
| VEGFR-2 | 1316 | UACAUGUCAGCGUUUGAGUGG | 99 | ACUCAAACGCUGACAUGUATT | 549 |
| VEGFR-2 | 3520 | UAUCGGAAGAACAAUGUAGTC | 100 | CUACAUUGUUCUUCCGAUATT | 550 |
| VEGFR-3 | 453 | UUCCUGUUGACCAAGAGCGTG | 101 | CGCUCUUGGUCAACAGGAATT | 551 |
| VEGFR-3 | 2694 | UUGAGCUCCGACAUCAGCGCG | 102 | CGCUGAUGUCGGAGCUCAATT | 552 |
| VEGFR-3 | 1689 | UUGGAUUCGAUGGUGAAGCCG | 103 | GCUUCACCAUCGAAUCCAATT | 553 |
| VEGFR-3 | 988 | UUCAUGCACAAUGACCUCGGT | 104 | CGAGGUCAUUGUGCAUGAATT | 554 |
| VEGFR-3 | 4374 | UUACCAAGGAAUAAUCGGCGG | 105 | GCCGAUUAUUCCUUGGUAATT | 555 |
| VEGFR-3 | 2142 | UCUUUGUACCACACGAUGCUG | 106 | GCAUCGUGUGGUACAAAGATT | 556 |
| VEGFR-3 | 1833 | UUGCAGUCGAGCAGAAGCGGG | 107 | CGCUUCUGCUCGACUGCAATT | 557 |
| VEGFR-3 | 3903 | UUCAGCUACCUGAAGCCGCTT | 108 | GCGGCUUCAGGUAGCUGAATT | 558 |
| VEGFR-3 | 3273 | UACACCUUGUCGAAGAUGCUU | 109 | GCAUCUUCGACAAGGUGUATT | 559 |
| VEGFR-3 | 1107 | UACCACUGGAACUCGGGCGGG | 110 | CGCCCGAGUUCCAGUGGUATT | 560 |
| VEGFR-3 | 336 | UAGCAGACGUAGCUGCCUGTG | 111 | CAGGCAGCUACGUCUGCUATT | 561 |
| VEGFR-3 | 2607 | UUGUGGAUGCCGAAAGCGGAG | 112 | CCGCUUUCGGCAUCCACAATT | 562 |
| VEGFR-3 | 1556 | UCACAGUCUUAUUCUUUCCCT | 113 | GGAAAGAAUAAGACUGUGATT | 563 |
| VEGFR-3 | 108 | UCCGUGAUGUUCAAGGUCGGG | 114 | CGACCUUGAACAUCACGGATT | 564 |
| VEGFR-3 | 1954 | AUAGUGGCCCUCGUGCUCGGG | 115 | CGAGCACGAGGGCCACUAUTT | 565 |
| VEGFR-3 | 2100 | AAGCACUGCAUCUCCAGCGAG | 116 | CGCUGGAGAUGCAGUGCUUTT | 566 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| VEGFR-3 | 693 | UCAUAGAGCUCGUUGCCUGTG | 117 | CAGGCAACGAGCUCUAUGATT | 567 |
| VEGFR-3 | 2337 | AGGAUCACGAUCUCCAUGCTG | 118 | GCAUGGAGAUCGUGAUCCUTT | 568 |
| VEGFR-3 | 2054 | UCAAGUUCUGCGUGAGCCGAG | 119 | CGGCUCACGCAGAACUUGATT | 569 |
| VEGFR-3 | 860 | UCUGUUGGGAGCGUCGCUCGG | 120 | GAGCGACGCUCCCAACAGATT | 570 |
| VEGFR-3 | 2436 | UAGCCCGUCUUGAUGUCUGCG | 121 | CAGACAUCAAGACGGGCUATT | 571 |
| VEGFR-3 | 3759 | UUCAUCCUGGAGGAACCACGG | 122 | GUGGUUCCUCCAGGAUGAATT | 572 |
| VEGFR-3 | 288 | AACACCUUGCAGUAGGGCCTG | 123 | GGCCCUACUGCAAGGUGUUTT | 573 |
| VEGFR-3 | 1485 | UGCGUGGUCACCGCCCUCCAG | 124 | GGAGGGCGGUGACCACGCATT | 574 |
| VEGFR-3 | 2502 | UCGUAGGACAGGUAUUCGCAT | 125 | GCGAAUACCUGUCCUACGATT | 575 |
| VEGFR-3 | 925 | AUACGAGCCCAGGUCGUGCTG | 126 | GCACGACCUGGGCUCGUAUTT | 576 |
| VEGFR-3 | 426 | UUGUUGAUGAAUGGCUGCUCA | 127 | AGCAGCCAUUCAUCAACAATT | 577 |
| VEGFR-3 | 3189 | UAGAUGUCCCGGGCAAGGCCA | 128 | GCCUUGCCCGGACAUCUATT | 578 |
| VEGFR-3 | 2274 | UUGACGCAGCCCUUGGGUCTG | 129 | GACCCAAGGGCUGCGUCAATT | 579 |
| VEGFR-3 | 2196 | UUCUGGUUGGAGUCCGCCAAG | 130 | UGGCGGACUCCAACCAGAATT | 580 |
| VEGFR-3 | 2019 | UGCACCGACAGGUACUUCUTG | 131 | AGAAGUACCUGUCGGUGCATT | 581 |
| VEGFR-3 | 360 | AUGCGUGCCUUGAUGUACUTG | 132 | AGUACAUCAAGGCACGCAUTT | 582 |
| VEGFR-3 | 1755 | UACUUGUAGCUGUCGGCUUGG | 133 | AAGCCGACAGCUACAAGUATT | 583 |
| VEGFR-3 | 3037 | UUCCAUGGUCAGCGGGCUCAG | 134 | GAGCCCGCUGACCAUGGAATT | 584 |
| VEGFR-3 | 1018 | UUUGAGCCACUCGACGCUGAT | 135 | CAGCGUCGAGUGGCUCAAATT | 585 |
| VEGFR-3 | 1684 | UUCGAUGGUGAAGCCGUCGGG | 136 | CGACGGCUUCACCAUCGAATT | 586 |
| VEGFR-3 | 4373 | UACCAAGGAAUAAUCGGCGGG | 137 | CGCCGAUUAUUCCUUGGUATT | 587 |
| VEGFR-3 | 987 | UCAUGCACAAUGACCUCGGTG | 138 | CCGAGGUCAUUGUGCAUGATT | 588 |
| VEGFR-3 | 3267 | UUGUCGAAGAUGCUUUCAGGG | 139 | CUGAAAGCAUCUUCGACAATT | 589 |
| VEGFR-3 | 4387 | UGUAUUACUCAUAUUACCAAG | 140 | UGGUAAUAUGAGUAAUACATT | 590 |
| VEGFR-3 | 3883 | UUCUUGUCUAUGCCUGCUCTC | 141 | GAGCAGGCAUAGACAAGAATT | 591 |
| VEGFR-3 | 4376 | UAUUACCAAGGAAUAAUCGGC | 142 | CGAUUAUUCCUUGGUAAUATT | 592 |
| VEGFR-3 | 2140 | UUUGUACCACACGAUGCUGGG | 143 | CAGCAUCGUGUGGUACAAATT | 593 |
| VEGFR-3 | 978 | AUGACCUCGGUGCUCUCCCGA | 144 | GGGAGAGCACCGAGGUCAUTT | 594 |
| VEGFR-3 | 2427 | UUGAUGUCUGCGUGGGCCGGC | 145 | CGGCCCACGCAGACAUCAATT | 595 |
| VEGFR-3 | 1109 | UGUACCACUGGAACUCGGGCG | 146 | CCCGAGUUCCAGUGGUACATT | 596 |
| VEGFR-3 | 319 | UGUGUCGUUGGCAUGUACCTC | 147 | GGUACAUGCCAACGACACATT | 597 |
| VEGFR-3 | 1843 | AUGCACGUUCUUGCAGUCGAG | 148 | CGACUGCAAGAACGUGCAUTT | 598 |
| VEGFR-3 | 317 | UGUCGUUGGCAUGUACCUCGT | 149 | GAGGUACAUGCCAACGACATT | 599 |
| VEGFR-3 | 700 | CUGGAUGUCAUAGAGCUCGTT | 150 | CGAGCUCUAUGACAUCCAGTT | 600 |
| Tie-2 (TEK) | 1223 | UAAGCUUACAAUCUGGCCCGT | 151 | GGGCCAGAUUGUAAGCUUATT | 601 |
| Tie-2 (TEK) | 2350 | UAUCUUCACAUCAACGUGCTG | 152 | GCACGUUGAUGUGAAGAUATT | 602 |
| Tie-2 | 706 | UAUGUUCACGUUAUCUCCCTT | 153 | GGGAGAUAACGUGAACAUATT | 603 |

TABLE 1-continued siRNAs against human VEGFR-1, VEGFR-2, VEGFR-3, Tie2, bFGFR,
IL8RA, IL8RB, Fas, IGF2R

| Target Name | pos | siRNA guide sequence | SEQ ID NO | siRNA complement | SEQ ID NO |
|---|---|---|---|---|---|
| Tie-2 (TEK) | 3561 | UUUAAGGACACCAAUAUCUGG | 154 | AGAUAUUGGUCUCCUUAAATT | 604 |
| Tie-2 (TEK) | 2763 | UGAAAUUUGAUGUCAUUCCAG | 155 | GGAAUGACAUCAAAUUUCATT | 605 |
| Tie-2 (TEK) | 174 | UUGUUUACAAGUUAGAGGCAA | 156 | GCCUCUAACUUGUAAACAATT | 606 |
| Tie-2 (TEK) | 1183 | UUCAUUGCACUGCAGACCCTT | 157 | GGGUCUGCAGUGCAAUGAATT | 607 |
| Tie-2 (TEK) | 805 | UAGAAUAUCAGGUACUUCATG | 158 | UGAAGUACCUGAUAUUCUATT | 608 |
| Tie-2 (TEK) | 2601 | UUCAAUUGCAAUAUGAUCAGA | 159 | UGAUCAUAUUGCAAUUGAATT | 609 |
| Tie-2 (TEK) | 2277 | UAGCCAUCCAAUAUUGUCCAA | 160 | GGACAAUAUUGGAUGGCUATT | 610 |
| Tie-2 (TEK) | 1366 | UACUUCUAUAUGAUCUGGCAA | 161 | GCCAGAUCAUAUAGAAGUATT | 611 |
| Tie-2 (TEK) | 32 | <u>UUUGGUAUCAGCAGGGCUGGG</u> | 162 | CAGCCCUGCUGAUACCAAATT | 612 |
| Tie-2 (TEK) | 4085 | UGUACUAUCAGGGUCAUUGTT | 163 | CAAUGACCCUGAUAGUACATT | 613 |
| Tie-2 (TEK) | 3881 | UUCUGAUUUCAGCCCAUUCTT | 164 | GAAUGGGCUGAAAUCAGAATT | 614 |
| Tie-2 (TEK) | 646 | UUGUUGACGCAUCUUCAUGGT | 165 | CAUGAAGAUGCGUCAACAATT | 615 |
| Tie-2 (TEK) | 4021 | AUAGCAUUCAACAUAAAGGTA | 166 | CCUUUAUGUUGAAUGCUAUTT | 616 |
| Tie-2 (TEK) | 209 | <u>UUUGUGACUUUCCAUUAGCAT</u> | 167 | GCUAAUGGAAAGUCACAAATT | 617 |
| Tie-2 (TEK) | 4223 | UAAAUGAAACGGGACUGGCTG | 168 | GCCAGUCCCGUUUCAUUUATT | 618 |
| Tie-2 (TEK) | 3961 | UACUAAUUGUACUCACGCCTT | 169 | GGCGUGAGUACAAUUAGUATT | 619 |
| Tie-2 (TEK) | 1771 | UUGAAUAUGUUGCCAAGCCTC | 170 | GGCUUGGCAACAUAUUCAATT | 620 |
| Tie-2 (TEK) | 3909 | UUAUUGCAUAUGAAACCACAA | 171 | GUGGUUUCAUAUGCAAUAATT | 621 |
| Tie-2 (TEK) | 3606 | UAAAGCGUGGUAUUCACGUAG | 172 | ACGUGAAUACCACGCUUUATT | 622 |
| Tie-2 (TEK) | 477 | AUUAAGGCUUCAAAGUCCCTT | 173 | GGGACUUUGAAGCCUUAAUTT | 623 |
| Tie-2 (TEK) | 3421 | UUCUGCACAAGUCAUCCCGCA | 174 | CGGGAUGACUUGUGCAGAATT | 624 |
| Tie-2 (TEK) | 2730 | UAAAUUGUAGGAUCUGGGUTG | 175 | ACCCAGAUCCUACAAUUUATT | 625 |
| Tie-2 (TEK) | 1800 | UAGUUGAGUGUAACAAUCUCA | 176 | AGAUUGUUACACUCAACUATT | 626 |
| Tie-2 (TEK) | 3385 | UAAGCUAACAAUCUCCCAUAG | 177 | AUGGGAGAUUGUUAGCUUATT | 627 |
| Tie-2 (TEK) | 1692 | UAAGGCUCAGAGCUGAUGUTG | 178 | ACAUCAGCUCUGAGCCUUATT | 628 |

TABLE 1-continued siRNAs against human VEGFR-1, VEGFR-2, VEGFR-3, Tie2, bFGFR,
IL8RA, IL8RB, Fas, IGF2R

| Target Name | pos | siRNA guide sequence | SEQ ID NO | siRNA complement | SEQ ID NO |
|---|---|---|---|---|---|
| Tie-2 (TEK) | 1657 | AUGUCCAGUGUCAAUCACGTT | 179 | CGUGAUUGACACUGGACAUTT | 629 |
| Tie-2 (TEK) | 3665 | UUCUGUCCUAGGCCGCUUCTT | 180 | GAAGCGGCCUAGGACAGAATT | 630 |
| Tie-2 (TEK) | 2091 | UUAAGUAGCACCGAAGUCAAG | 181 | UGACUUCGGUGCUACUUAATT | 631 |
| Tie-2 (TEK) | 2827 | UAACCCAUCCUUCUUGAUGCG | 182 | CAUCAAGAAGGAUGGGUUATT | 632 |
| Tie-2 (TEK) | 1979 | UUGGUUGCCAGGUCAAAUUTA | 183 | AAUUUGACCUGGCAACCAATT | 633 |
| Tie-2 (TEK) | 67 | UAGAUUAGGAUGGGAAAGGCT | 184 | CCUUUCCCAUCCUAAUCUATT | 634 |
| Tie-2 (TEK) | 3459 | UUCUCCAGUCUGUAGCCCUGG | 185 | AGGGCUACAGACUGGAGAATT | 635 |
| Tie-2 (TEK) | 2764 | UUGAAAUUUGAUGUCAUUCCA | 186 | GAAUGACAUCAAAUUUCAATT | 636 |
| Tie-2 (TEK) | 3560 | UUAAGGACACCAAUAUCUGGG | 187 | CAGAUAUUGGUGUCCUUAATT | 637 |
| Tie-2 (TEK) | 715 | UUUGAAAGAUAUGUUCACGTT | 188 | CGUGAACAUAUCUUUCAAATT | 638 |
| Tie-2 (TEK) | 1368 | UUUACUUCUAUAUGAUCUGGC | 189 | CAGAUCAUAUAGAAGUAAATT | 639 |
| Tie-2 (TEK) | 2351 | UUAUCUUCACAUCAACGUGCT | 190 | CACGUUGAUGUGAAGAUAATT | 640 |
| Tie-2 (TEK) | 205 | UGACUUUCCAUUAGCAUCGTC | 191 | CGAUGCUAAUGGAAAGUCATT | 641 |
| Tie-2 (TEK) | 3957 | AAUUGUACUCACGCCUUCCTA | 192 | GGAAGGCGUGAGUACAAUUTT | 642 |
| Tie-2 (TEK) | 3962 | AUACUAAUUGUACUCACGCCT | 193 | GCGUGAGUACAAUUAGUAUTT | 643 |
| Tie-2 (TEK) | 2352 | UUUAUCUUCACAUCAACGUGC | 194 | ACGUUGAUGUGAAGAUAAATT | 644 |
| Tie-2 (TEK) | 3963 | UAUACUAAUUGUACUCACGCC | 195 | CGUGAGUACAAUUAGUAUATT | 645 |
| Tie-2 (TEK) | 1777 | UGUCACUUGAAUAUGUUGCCA | 196 | GCAACAUAUUCAAGUGACATT | 646 |
| Tie-2 (TEK) | 3388 | UCCUAAGCUAACAAUCUCCCA | 197 | GGAGAUUGUUAGCUUAGGATT | 647 |
| Tie-2 (TEK) | 636 | AUCUUCAUGGUUCGUAUCCTG | 198 | GGAUACGAACCAUGAAGAUTT | 648 |
| Tie-2 (TEK) | 74 | UCCUUUGUAGAUUAGGAUGGG | 199 | CAUCCUAAUCUACAAAGGATT | 649 |
| Tie-2 (TEK) | 707 | AUAUGUUCACGUUAUCUCCCT | 200 | GGAGAUAACGUGAACAUAUTT | 650 |
| bFGFR | 3814 | UAAAUCUCUGGUAACGACCCT | 201 | GGUCGUUACCAGAGAUUUATT | 651 |
| bFGFR | 1478 | UUACACAUGAACUCCACGUTG | 202 | ACGUGGAGUUCAUGUGUAATT | 652 |
| bFGFR | 3773 | UAUACUCAGAUUUUAUCAACTT | 203 | GUUGAUAAAUCUGAGUAUATT | 653 |
| bFGFR | 715 | UAGCGGUGCAGAGUGUGGCTG | 204 | GCCACACUCUGCACCGCUATT | 654 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| bFGFR | 575 | UUCAAACUGACCCUCGCUCGG | 205 | GAGCGAGGGUCAGUUUGAATT | 655 |
| bFGFR | 646 | UUCUGCAGUUAGAGGUUGGTG | 206 | CCAACCUCUAACUGCAGAATT | 656 |
| bFGFR | 3625 | AUCGGAAUUAAUAAGCCACTG | 207 | GUGGCUUAUUAAUUCCGAUTT | 657 |
| bFGFR | 2318 | UACAAGGGACCAUCCUGCGTG | 208 | CGCAGGAUGGUCCCUUGUATT | 658 |
| bFGFR | 1439 | UUGUUGGCGGGCAACCCUGCT | 209 | CAGGGUUGCCCGCCAACAATT | 659 |
| bFGFR | 3860 | AUAGCAACUGAUGCCUCCCAG | 210 | GGGAGGCAUCAGUUGCUAUTT | 660 |
| bFGFR | 3163 | UGAGGGUUACAGCUGACGGTG | 211 | CCGUCAGCUGUAACCCUCATT | 661 |
| bFGFR | 2600 | UCGAUGUGGUGAAUGUCCCGT | 212 | GGGACAUUCACCACAUCGATT | 662 |
| bFGFR | 2513 | UCUCGGUGUAUGCACUUCUTG | 213 | AGAAGUGCAUACACCGAGATT | 663 |
| bFGFR | 2214 | UUUCUCUGUUGCGUCCGACTT | 214 | GUCGGACGCAACAGAGAAATT | 664 |
| bFGFR | 1346 | UUCUCCACAAUGCAGGUGUAG | 215 | ACACCUGCAUUGUGGAGAATT | 665 |
| bFGFR | 1556 | UUGUCUGGGCCAAUCUUGCTC | 216 | GCAAGAUUGGCCCAGACAATT | 666 |
| bFGFR | 2671 | UCCGGUCAAAUAAUGCCUCGG | 217 | GAGGCAUUAUUUGACCGGATT | 667 |
| bFGFR | 3105 | UUUGAGUCCGCCAUUGGCAAG | 218 | UGCCAAUGGCGGACUCAAATT | 668 |
| bFGFR | 2091 | UUUGCCUAAGACCAGUCUGTC | 219 | CAGACUGGUCUUAGGCAAATT | 669 |
| bFGFR | 1590 | UCCAGCAGUCUUCAAGAUCTG | 220 | GAUCUUGAAGACUGCUGGATT | 670 |
| bFGFR | 1689 | UCCGAUAGAGUUACCCGCCAA | 221 | GGCGGGUAACUCUAUCGGATT | 671 |
| bFGFR | 1319 | UUGUCAGAGGGCACCACAGAG | 222 | CUGUGGUGCCCUCUGACAATT | 672 |
| bFGFR | 2342 | UUGGAGGCAUACUCCACGATG | 223 | UCGUGGAGUAUGCCUCCAATT | 673 |
| bFGFR | 107 | UCUCGGUCCCGACCGGACGTG | 224 | CGUCCGGUCGGGACCGAGATT | 674 |
| bFGFR | 3662 | UCUGGUACCAGGCAUUUGGTC | 225 | CCAAAUGCCUGGUACCAGATT | 675 |
| bFGFR | 2150 | UUGUCCAGCCCGAUAGCCUCT | 226 | AGGCUAUCGGGCUGGACAATT | 676 |
| bFGFR | 1517 | UUUAGCCACUGGAUGUGCGGC | 227 | CGCACAUCCAGUGGCUAAATT | 677 |
| bFGFR | 1264 | UGUAGCCUCCAAUUCUGUGGT | 228 | CACAGAAUUGGAGGCUACATT | 678 |
| bFGFR | 3576 | UUCAAUCGUGGCUCGAAGCAC | 229 | GCUUCGAGCCACGAUUGAATT | 679 |
| bFGFR | 613 | AUCUCCAUGGAUACUCCACAG | 230 | GUGGAGUAUCCAUGGAGAUTT | 680 |
| bFGFR | 1221 | UUUCAACCAGCGCAGUGUGGG | 231 | CACACUGCGCUGGUUGAAATT | 681 |
| bFGFR | 3004 | UAGAGCUCCGGGUGUCGGGAA | 232 | CCCGACACCCGGAGCUCUATT | 682 |
| bFGFR | 3825 | UUACCGAUGGGUAAAUCUCTG | 233 | GAGAUUUACCCAUCGGUAATT | 683 |
| bFGFR | 3813 | AAAUCUCUGGUAACGACCCTT | 234 | GGGUCGUUACCAGAGAUUUTT | 684 |
| bFGFR | 3861 | UAUAGCAACUGAUGCCUCCCA | 235 | GGAGGCAUCAGUUGCUAUATT | 685 |
| bFGFR | 576 | UUUCAAACUGACCCUCGCUCG | 236 | AGCGAGGGUCAGUUUGAAATT | 686 |
| bFGFR | 3772 | AUACUCAGAUUUAUCAACUTT | 237 | AGUUGAUAAAUCUGAGUAUTT | 687 |
| bFGFR | 3824 | UACCGAUGGGUAAAUCUCUGG | 238 | AGAGAUUUACCCAUCGGUATT | 688 |
| bFGFR | 2319 | AUACAAGGGACCAUCCUGCGT | 239 | GCAGGAUGGUCCCUUGUAUTT | 689 |
| bFGFR | 3771 | UACUCAGAUUUAUCAACUUTG | 240 | AAGUUGAUAAAUCUGAGUATT | 690 |
| bFGFR | 2511 | UCGGUGUAUGCACUUCUUGGA | 241 | CAAGAAGUGCAUACACCGATT | 691 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| bFGFR | 2333 | UACUCCACGAUGACAUACAAG | 242 | UGUAUGUCAUCGUGGAGUAUU | 692 |
| bFGFR | 3624 | UCGGAAUUAAUAAGCCACUGG | 243 | AGUGGCUUAUUAAUUCCGAUU | 693 |
| bFGFR | 1304 | ACAGAGUCCAUUAUGAUGCUC | 244 | GCAUCAUAAUGGACUCUGUUU | 694 |
| bFGFR | 1608 | UUUGUCGGUGGUAUUAACUCC | 245 | AGUUAAUACCACCGACAAAUU | 695 |
| bFGFR | 1301 | GAGUCCAUUAUGAUGCUCCAG | 246 | GGAGCAUCAUAAUGGACUCUU | 696 |
| bFGFR | 3626 | UAUCGGAAUUAAUAAGCCACU | 247 | UGGCUUAUUAAUUCCGAUAUU | 697 |
| bFGFR | 2672 | AUCCGGUCAAAUAAUGCCUCG | 248 | AGGCAUUAUUUGACCGGAUUU | 698 |
| bFGFR | 2213 | UUCUCUGUUGCGUCCGACUUC | 249 | AGUCGGACGCAACAGAGAAUU | 699 |
| bFGFR | 2597 | AUGUGGUGAAUGUCCCGUGCG | 250 | CACGGGACAUUCACCACAUUU | 700 |
| IL8RA | 1971 | UUUAUUAGGAACAUCUGCCUG | 251 | GGCAGAUGUUCCUAAUAAAUU | 701 |
| IL8RA | 75 | UUGAUCUAACUGAAGCACCGG | 252 | GGUGCUUCAGUUAGAUCAAUU | 702 |
| IL8RA | 645 | AUUGUUUGGAUGGUAAGCCUG | 253 | GGCUUACCAUCCAAACAAUUU | 703 |
| IL8RA | 1431 | UAAUUAGCCAGUUAGUGGGUU | 254 | CCCACUAACUGGCUAAUUAUU | 704 |
| IL8RA | 1378 | UUCGUUUCCAUGGAGGUGCAA | 255 | GCACCUCCAUGGAAACGAAUU | 705 |
| IL8RA | 1470 | UCAUCUAAUGUCAGAUUCGGG | 256 | CGAAUCUGACAUUAGAUGAUU | 706 |
| IL8RA | 218 | UACUUGUUGAGUGUCUCAGUU | 257 | CUGAGACACUCAACAAGUAUU | 707 |
| IL8RA | 1101 | AUGACGUGCCAAGAACUCCUU | 258 | GGAGUUCUUGGCACGUCAUUU | 708 |
| IL8RA | 677 | UUUCCCAGGACCUCAUAGCAA | 259 | GCUAUGAGGUCCUGGGAAAUU | 709 |
| IL8RA | 1178 | AAGAGAUAUUCCUUCAUCGAU | 260 | CGAUGAAGGAAUAUCUCUUUU | 710 |
| IL8RA | 1543 | UUGAGGAGAUGCUCCUGUGAG | 261 | CACAGGAGCAUCUCCUCAAUU | 711 |
| IL8RA | 1783 | UCUUGUGGCAUAGAUCUGGCT | 262 | CCAGAUCUAUGCCACAAGAUU | 712 |
| IL8RA | 1249 | AUAGUGCCUGUCCAGAGCCAG | 263 | GGCUCUGGACAGGCACUAUUU | 713 |
| IL8RA | 1520 | UCAACGAGAGCAUCCAGCCCT | 264 | GGCUGGAUGCUCUCGUUGAUU | 714 |
| IL8RA | 1068 | AUGCAUAGCCAGGAUCUUGAG | 265 | CAAGAUCCUGGCUAUGCAUUU | 715 |
| IL8RA | 1347 | UUGGAGGUACCUCAACAGCUC | 266 | GCUGUUGAGGUACCUCCAAUU | 716 |
| IL8RA | 1208 | UCAGGGUGUUGGUUAUUCUUU | 267 | AGAAUAACCAACACCCUGAUU | 717 |
| IL8RA | 117 | AUCUGUAAUAUUUGACAUGUC | 268 | CAUGUCAAAUAUUACAGAUUU | 718 |
| IL8RA | 1862 | UGCUUGUCUCGUUCCACUUGG | 269 | AAGUGGAACGAGACAAGCAUU | 719 |
| IL8RA | 1153 | UUCAGAGGUUGGAAGAGACAT | 270 | GUCUCUUCCAACCUCUGAAUU | 720 |
| IL8RA | 640 | UUGGAUGGUAAGCCUGGCGGA | 271 | CGCCAGGCUUACCAUCCAAUU | 721 |
| IL8RA | 1411 | UAAAGAUGUGACGUUCAACGG | 272 | GUUGAACGUCACAUCUUUAUU | 722 |
| IL8RA | 71 | UCUAACUGAAGCACCGGCCAG | 273 | GGCCGGUGCUUCAGUUAGAUU | 723 |
| IL8RA | 1397 | UCAACGGGAAUGAUGGUGCUU | 274 | GCACCAUCAUUCCCGUUGAUU | 724 |
| IL8RA | 644 | UUGUUUGGAUGGUAAGCCUGG | 275 | AGGCUUACCAUCCAAACAAUU | 725 |
| IL8RA | 641 | UUUGGAUGGUAAGCCUGGCGG | 276 | GCCAGGCUUACCAUCCAAAUU | 726 |
| IL8RA | 76 | UUUGAUCUAACUGAAGCACCG | 277 | GUGCUUCAGUUAGAUCAAAUU | 727 |
| IL8RA | 1398 | UUCAACGGGAAUGAUGGUGCT | 278 | CACCAUCAUUCCCGUUGAAUU | 728 |
| IL8RA | 1381 | UGCUUCGUUUCCAUGGAGGTG | 279 | CCUCCAUGGAAACGAAGCAUU | 729 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| IL8RA | 1769 | UCUGGCUUCCAAACCCUCUTT | 280 | AGAGGGUUUGGAAGCCAGATT | 730 |
| IL8RA | 1435 | AUGCUAAUUAGCCAGUUAGTG | 281 | CUAACUGGCUAAUUAGCAUTT | 731 |
| IL8RA | 1175 | AGAUAUUCCUUCAUCGAUGGT | 282 | CAUCGAUGAAGGAAUAUCUTT | 732 |
| IL8RA | 1970 | UUAUUAGGAACAUCUGCCUGC | 283 | AGGCAGAUGUUCCUAAUAATT | 733 |
| IL8RA | 1432 | CUAAUUAGCCAGUUAGUGGGT | 284 | CCACUAACUGGCUAAUUAGTT | 734 |
| IL8RA | 74 | UGAUCUAACUGAAGCACCGGC | 285 | CGGUGCUUCAGUUAGAUCATT | 735 |
| IL8RA | 646 | AAUUGUUUGGAUGGUAAGCCT | 286 | GCUUACCAUCCAAACAAUUTT | 736 |
| IL8RA | 639 | UGGAUGGUAAGCCUGGCGGAA | 287 | CCGCCAGGCUUACCAUCCATT | 737 |
| IL8RA | 1082 | UUGCUGACCAGGCCAUGCAUA | 288 | UGCAUGGCCUGGUCAGCAATT | 738 |
| IL8RA | 1770 | AUCUGGCUUCCAAACCCUCTT | 289 | GAGGGUUUGGAAGCCAGAUTT | 739 |
| IL8RA | 81 | AAUGGUUUGAUCUAACUGAAG | 290 | UCAGUUAGAUCAAACCAUUTT | 740 |
| IL8RA | 1372 | UCCAUGGAGGUGCAAAGGCCG | 291 | GCCUUUGCACCUCCAUGGATT | 741 |
| IL8RA | 1388 | AUGAUGGUGCUUCGUUUCCAT | 292 | GGAAACGAAGCACCAUCAUTT | 742 |
| IL8RA | 643 | UGUUUGGAUGGUAAGCCUGGC | 293 | CAGGCUUACCAUCCAAACATT | 743 |
| IL8RA | 1784 | UUCUUGUGGCAUAGAUCUGGC | 294 | CAGAUCUAUGCCACAAGAATT | 744 |
| IL8RA | 1524 | AGGGUCAACGAGAGCAUCCAG | 295 | GGAUGCUCUCGUUGACCCUTT | 745 |
| IL8RA | 237 | AUAGGCGAUGAUCACAACATA | 296 | UGUUGUGAUCAUCGCCUAUTT | 746 |
| IL8RA | 219 | AUACUUGUUGAGUGUCUCAGT | 297 | UGAGACACUCAACAAGUAUTT | 747 |
| IL8RA | 1389 | AAUGAUGGUGCUUCGUUUCCA | 298 | GAAACGAAGCACCAUCAUUTT | 748 |
| IL8RA | 1972 | CUUUAUUAGGAACAUCUGCCT | 299 | GCAGAUGUUCCUAAUAAAGTT | 749 |
| IL8RA | 1115 | UAGGAGGUAACACGAUGACGT | 300 | GUCAUCGUGUUACCUCCUATT | 750 |
| IL8RB | 2648 | UUAAGUGUCAAUUUAGUGGCA | 301 | CCACUAAAUUGACACUUAATT | 751 |
| IL8RB | 2184 | UUUCUUGUGGGUCAAUUCCTA | 302 | GGAAUUGACCCACAAGAAATT | 752 |
| IL8RB | 2250 | UUGGGUCUUGUGAAUAAGCTG | 303 | GCUUAUUCACAAGACCCAATT | 753 |
| IL8RB | 1746 | UUCACUUCUUAGAACAUAGAG | 304 | CUAUGUUCUAAGAAGUGAATT | 754 |
| IL8RB | 960 | UUGGAUGAGUAGACGGUCCTT | 305 | GGACCGUCUACUCAUCCAATT | 755 |
| IL8RB | 454 | AUUACUAAGAUCUUCACCUTT | 306 | AGGUGAAGAUCUUAGUAAUTT | 756 |
| IL8RB | 2750 | UUGGUUUAAUCAGCCUUGGTG | 307 | CCAAGGCUGAUUAAACCAATT | 757 |
| IL8RB | 2604 | AUCACUACUGUUUAUCUGCAG | 308 | GCAGAUAAACAGUAGUGAUTT | 758 |
| IL8RB | 1026 | AUCCGUAACAGCAUCCGCCAG | 309 | GGCGGAUGCUGUUACGGAUTT | 759 |
| IL8RB | 1384 | AUGUAUAGCUAGAAUCUUGAG | 310 | CAAGAUUCUAGCUAUACAUTT | 760 |
| IL8RB | 1149 | AAGAUGACCCGCAUGGCCCGG | 311 | GGGCCAUGCGGGUCAUCUUTT | 761 |
| IL8RB | 2464 | UCUCAGUACCUCAUGUAGGTG | 312 | CCUACAUGAGGUACUGAGATT | 762 |
| IL8RB | 877 | UUUGACCAAGUAGCGCUUCTG | 313 | GAAGCGCUACUUGGUCAAATT | 763 |
| IL8RB | 2324 | UUCGUUAGGUACAUAUCACAT | 314 | GUGAUAUGUACCUAACGAATT | 764 |
| IL8RB | 2360 | AUGAGUACUUCAUUCCUCUTT | 315 | AGAGGAAUGAAGUACUCAUTT | 765 |
| IL8RB | 265 | UUGGGUGGUAGUCAGAGCUGT | 316 | AGCUCUGACUACCACCCAATT | 766 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| IL8RB | 1642 | UUUCUAAACCAUGCAAGGGAA | 317 | CCCUUGCAUGGUUUAGAAATT | 767 |
| IL8RB | 2146 | UCAUGUGUUAAUUCUAUGUCT | 318 | ACAUAGAAUUAACACAUGATT | 768 |
| IL8RB | 2627 | UUAAGUCACAUUGCGGUACAA | 319 | GUACCGCAAUGUGACUUAATT | 769 |
| IL8RB | 1000 | UGUAUUGUUGCCCAUGUCCUC | 320 | GGACAUGGGCAACAAUACATT | 770 |
| IL8RB | 315 | UGACCUGCUGUUAUUGGAGTG | 321 | CUCCAAUAACAGCAGGUCATT | 771 |
| IL8RB | 2774 | AAAUAUAGGCAGGUGGUUCUA | 322 | GAACCACCUGCCUAUAUUUTT | 772 |
| IL8RB | 219 | ACCUUGACGAUGAAACUUCUG | 323 | GAAGUUUCAUCGUCAAGGUTT | 773 |
| IL8RB | 2389 | UUUCAAGGUUCGUCCGUGUTG | 324 | ACACGGACGAACCUUGAAATT | 774 |
| IL8RB | 385 | UGAGGUAAACUUAAAUCCUGA | 325 | AGGAUUUAAGUUUACCUCATT | 775 |
| IL8RB | 1347 | UUCUGGCCAAUGAAGGCGUAG | 326 | ACGCCUUCAUUGGCCAGAATT | 776 |
| IL8RB | 2649 | UUUAAGUGUCAAUUUAGUGGC | 327 | CACUAAAUUGACACUUAAATT | 777 |
| IL8RB | 1737 | UAGAACAUAGAGUGCCAUGGG | 328 | CAUGGCACUCUAUGUUCUATT | 778 |
| IL8RB | 455 | AAUUACUAAGAUCUUCACCTT | 329 | GGUGAAGAUCUUAGUAAUUTT | 779 |
| IL8RB | 965 | UAACAUUGGAUGAGUAGACGG | 330 | GUCUACUCAUCCAAUGUUATT | 780 |
| IL8RB | 1740 | UCUUAGAACAUAGAGUGCCAT | 331 | GGCACUCUAUGUUCUAAGATT | 781 |
| IL8RB | 2632 | UGGCAUUAAGUCACAUUGCGG | 332 | GCAAUGUGACUUAAUGCCATT | 782 |
| IL8RB | 2755 | UAGCCUUGGUUUAAUCAGCCT | 333 | GCUGAUUAAACCAAGGCUATT | 783 |
| IL8RB | 2183 | UUCUGUGGGUCAAUUCCUAT | 334 | AGGAAUUGACCCACAAGAATT | 784 |
| IL8RB | 2605 | UAUCACUACUGUUUAUCUGCA | 335 | CAGAUAAACAGUAGUGAUATT | 785 |
| IL8RB | 2340 | UCAGGCUGAAGGAUACUUCGT | 336 | GAAGUAUCCUUCAGCCUGATT | 786 |
| IL8RB | 2143 | UGUGUUAAUUCUAUGUCUGAA | 337 | CAGACAUAGAAUUAACACATT | 787 |
| IL8RB | 998 | UAUUGUUGCCCAUGUCCUCAT | 338 | GAGGACAUGGGCAACAAUATT | 788 |
| IL8RB | 2180 | UUGUGGGUCAAUUCCUAUAAG | 339 | UAUAGGAAUUGACCCACAATT | 789 |
| IL8RB | 2185 | AUUUCUUGUGGGUCAAUUCCT | 340 | GAAUUGACCCACAAGAAAUTT | 790 |
| IL8RB | 307 | UGUUAUUGGAGUGGCCACCGA | 341 | GGUGGCCACUCCAAUAACATT | 791 |
| IL8RB | 2481 | UCUGUAAAUUUGUUCACUCTC | 342 | GAGUGAACAAAUUUACAGATT | 792 |
| IL8RB | 2617 | UUGCGGUACAACUAUCACUAC | 343 | AGUGAUAGUUGUACCGCAATT | 793 |
| IL8RB | 956 | AUGAGUAGACGGUCCUUCGGA | 344 | CGAAGGACCGUCUACUCAUTT | 794 |
| IL8RB | 456 | UAAUUACUAAGAUCUUCACCT | 345 | GUGAAGAUCUUAGUAAUUATT | 795 |
| IL8RB | 226 | UGAAACAACCUUGACGAUGAA | 346 | CAUCGUCAAGGUUGUUUCATT | 796 |
| IL8RB | 1394 | UGAUCAAGCCAUGUAUAGCTA | 347 | GCUAUACAUGGCUUGAUCATT | 797 |
| IL8RB | 458 | UGUAAUUACUAAGAUCUUCAC | 348 | GAAGAUCUUAGUAAUUACATT | 798 |
| IL8RB | 881 | UGAAUUUGACCAAGUAGCGCT | 349 | CGCUACUUGGUCAAAUUCATT | 799 |
| IL8RB | 2327 | UACUUCGUUAGGUACAUAUCA | 350 | AUAUGUACCUAACGAAGUATT | 800 |
| Fas | 109 | UGUAGUAACAGUCUUCCUCAA | 351 | GAGGAAGACUGUUACUACATT | 801 |
| Fas | 41 | UGGACGAUAAUCUAGCAACAG | 352 | GUUGCUAGAUUAUCGUCCATT | 802 |
| Fas | 161 | UAUGGCAGAAUUGGCCAUCAT | 353 | GAUGGCCAAUUCUGCCAUATT | 803 |
| Fas | 182 | UUUCACCUGGAGGACAGGGCT | 354 | CCCUGUCCUCCAGGUGAAATT | 804 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| Fas | 62 | UCACUUGGGCAUUAACACUTT | 355 | AGUGUUAAUGCCCAAGUGATT | 805 |
| Fas | 377 | ACUUCCUCUUUGCACUUGGTG | 356 | CCAAGUGCAAAGAGGAAGUTT | 806 |
| Fas | 349 | UGAGUGUGCAUUCCUUGAUGA | 357 | AUCAAGGAAUGCACACUCATT | 807 |
| Fas | 245 | UCCCUUCUUGGCAGGGCACGC | 358 | GUGCCCUGCCAAGAAGGGATT | 808 |
| Fas | 205 | GACUGUGCAGUCCCUAGCUTT | 359 | AGCUAGGGACUGCACAGUCTT | 809 |
| Fas | 145 | AUCAUGAUGCAGGCCUUCCAA | 360 | GGAAGGCCUGCAUCAUGATT | 810 |
| Fas | 123 | UUCUGAGUCUCAACUGUAGTA | 361 | CUACAGUUGAGACUCAGAATT | 811 |
| Fas | 34 | UAAUCUAGCAACAGACGUAAG | 362 | UACGUCUGUUGCUAGAUUATT | 812 |
| Fas | 114 | UCAACUGUAGUAACAGUCUTC | 363 | AGACUGUUACUACAGUUGATT | 813 |
| Fas | 115 | CUCAACUGUAGUAACAGUCTT | 364 | GACUGUUACUACAGUUGAGTT | 814 |
| Fas | 28 | AGCAACAGACGUAAGAACCAG | 365 | GGUUCUUACGUCUGUUGCUTT | 815 |
| Fas | 122 | UCUGAGUCUCAACUGUAGUAA | 366 | ACUACAGUUGAGACUCAGATT | 816 |
| Fas | 186 | UUCCUUUCACCUGGAGGACAG | 367 | GUCCUCCAGGUGAAAGGAATT | 817 |
| Fas | 42 | UUGGACGAUAAUCUAGCAACA | 368 | UUGCUAGAUUAUCGUCCAATT | 818 |
| Fas | 111 | ACUGUAGUAACAGUCUUCCTC | 369 | GGAAGACUGUUACUACAGUTT | 819 |
| Fas | 144 | UCAUGAUGCAGGCCUUCCAAG | 370 | UGGAAGGCCUGCAUCAUGATT | 820 |
| Fas | 92 | UCAAUUCCAAUCCCUUGGAGT | 371 | UCCAAGGGAUUGGAAUUGATT | 821 |
| Fas | 201 | GUGCAGUCCCUAGCUUUCCTT | 372 | GGAAAGCUAGGGACUGCACTT | 822 |
| Fas | 128 | CCAAGUUCUGAGUCUCAACTG | 373 | GUUGAGACUCAGAACUUGGTT | 823 |
| Fas | 36 | GAUAAUCUAGCAACAGACGTA | 374 | CGUCUGUUGCUAGAUUAUCTT | 824 |
| Fas | 162 | UUAUGGCAGAAUUGGCCAUCA | 375 | AUGGCCAAUUCUGCCAUAATT | 825 |
| Fas | 127 | CAAGUUCUGAGUCUCAACUGT | 376 | AGUUGAGACUCAGAACUUGTT | 826 |
| Fas | 202 | UGUGCAGUCCCUAGCUUUCCT | 377 | GAAAGCUAGGGACUGCACATT | 827 |
| Fas | 82 | UCCCUUGGAGUUGAUGUCAGT | 378 | UGACAUCAACUCCAAGGGATT | 828 |
| Fas | 160 | AUGGCAGAAUUGGCCAUCATG | 379 | UGAUGGCCAAUUCUGCCAUTT | 829 |
| Fas | 150 | UGGCCAUCAUGAUGCAGGCCT | 380 | GCCUGCAUCAUGAUGGCCATT | 830 |
| Fas | 63 | GUCACUUGGGCAUUAACACTT | 381 | GUGUUAAUGCCCAAGUGACTT | 831 |
| Fas | 164 | GCUUAUGGCAGAAUUGGCCAT | 382 | GGCCAAUUCUGCCAUAAGCTT | 832 |
| Fas | 37 | CGAUAAUCUAGCAACAGACGT | 383 | GUCUGUUGCUAGAUUAUCGTT | 833 |
| Fas | 116 | UCUCAACUGUAGUAACAGUCT | 384 | ACUGUUACUACAGUUGAGATT | 834 |
| Fas | 32 | AUCUAGCAACAGACGUAAGAA | 385 | CUUACGUCUGUUGCUAGAUTT | 835 |
| Fas | 64 | AGUCACUUGGGCAUUAACACT | 386 | UGUUAAUGCCCAAGUGACUTT | 836 |
| Fas | 167 | AGGGCUUAUGGCAGAAUUGGC | 387 | CAAUUCUGCCAUAAGCCCUTT | 837 |
| Fas | 120 | UGAGUCUCAACUGUAGUAACA | 388 | UUACUACAGUUGAGACUCATT | 838 |
| Fas | 125 | AGUUCUGAGUCUCAACUGUAG | 389 | ACAGUUGAGACUCAGAACUTT | 839 |
| Fas | 43 | UUUGGACGAUAAUCUAGCAAC | 390 | UGCUAGAUUAUCGUCCAAATT | 840 |
| Fas | 94 | CCUCAAUUCCAAUCCCUUGGA | 391 | CAAGGGAUUGGAAUUGAGGTT | 841 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| Fas | 159 | UGGCAGAAUUGGCCAUCAUGA | 392 | AUGAUGGCCAAUUCUGCCAUU | 842 |
| Fas | 110 | CUGUAGUAACAGUCUUCCUCA | 393 | AGGAAGACUGUUACUACAGUU | 843 |
| Fas | 31 | UCUAGCAACAGACGUAAGAAC | 394 | UCUUACGUCUGUUGCUAGAUU | 844 |
| Fas | 38 | ACGAUAAUCUAGCAACAGACG | 395 | UCUGUUGCUAGAUUAUCGUUU | 845 |
| Fas | 118 | AGUCUCAACUGUAGUAACAGT | 396 | UGUUACUACAGUUGAGACUUU | 846 |
| Fas | 169 | ACAGGGCUUAUGGCAGAAUTG | 397 | AUUCUGCCAUAAGCCCUGUUU | 847 |
| Fas | 33 | AAUCUAGCAACAGACGUAAGA | 398 | UUACGUCUGUUGCUAGAUUUU | 848 |
| Fas | 163 | CUUAUGGCAGAAUUGGCCATC | 399 | UGGCCAAUUCUGCCAUAAGUU | 849 |
| Fas | 233 | AGGGCACGCAGUCUGGUUCAT | 400 | GAACCAGACUGCGUGCCCUUU | 850 |
| IGF2R | 6340 | UUUGUCACCUAUGACACCCAG | 401 | GGGUGUCAUAGGUGACAAAUU | 851 |
| IGF2R | 2936 | UUAUAGAGCAAGCCUGGUCUG | 402 | GACCAGGCUUGCUCUAUAAUU | 852 |
| IGF2R | 1331 | UCUGAUUGUGGUAUCUUCCUG | 403 | GGAAGAUACCACAAUCAGAUU | 853 |
| IGF2R | 4491 | UAUUUCAGGACAAUUAUGCCA | 404 | GCAUAAUUGUCCUGAAAUAUU | 854 |
| IGF2R | 2562 | UUAAUGUAGUAUUUCCUCCAC | 405 | GGAGGAAAUACUACAUUAAUU | 855 |
| IGF2R | 1456 | UUUCCCAUCGUUACCUGCGGT | 406 | CGCAGGUAACGAUGGGAAAUU | 856 |
| IGF2R | 2253 | UAGUUCAGUUGGAUCAUCCCA | 407 | GGAUGAUCCAACUGAACUAUU | 857 |
| IGF2R | 3570 | UUGCCUUCUGACACUAAGCAA | 408 | GCUUAGUGUCAGAAGGCAAUU | 858 |
| IGF2R | 2274 | UUAUAGGGUGUGCCGCCUCUG | 409 | GAGGCGGCACACCCUAUAAUU | 859 |
| IGF2R | 1197 | UUUCCAUCUGAAAUAUAGGAT | 410 | CCUAUAUUUCAGAUGGAAAUU | 860 |
| IGF2R | 897 | UUGCGCACCAGCUUCAGUCCG | 411 | GACUGAAGCUGGUGCGCAAUU | 861 |
| IGF2R | 5205 | UUGAUGUAGAAAUCAGGGUTG | 412 | ACCCUGAUUUCUACAUCAAUU | 862 |
| IGF2R | 8904 | UUCUCAGCAAUAGAACACCAG | 413 | GGUGUUCUAUUGCUGAGAAUU | 863 |
| IGF2R | 8604 | UAAGGCUUCUUAUAGGUCGAA | 414 | CGACCUAUAAGAAGCCUUAUU | 864 |
| IGF2R | 3629 | UCAAAGAUCCAUUCGCCGCGG | 415 | GCGGCGAAUGGAUCUUUGAUU | 865 |
| IGF2R | 4344 | UUGAUGAGGUAGUGCUCCGGG | 416 | CGGAGCACUACCUCAUCAAUU | 866 |
| IGF2R | 1419 | UUUAUGACGCUCAUCCGCUGA | 417 | AGCGGAUGAGCGUCAUAAAUU | 867 |
| IGF2R | 7185 | UAUUUGUAGGACACGUUGGAA | 418 | CCAACGUGUCCUACAAAUAUU | 868 |
| IGF2R | 4447 | UACCCUGCCGAGGUUCACGGG | 419 | CGUGAACCUCGGCAGGGUAUU | 869 |
| IGF2R | 3706 | UAUCUGAGCACACUCAAACGT | 420 | GUUUGAGUGUGCUCAGAUAUU | 870 |
| IGF2R | 6422 | UCUUUGUACAGGUCAAUUCTA | 421 | GAAUUGACCUGUACAAAGAUU | 871 |
| IGF2R | 1306 | UUUGACUUGAGAGGUAUCGCT | 422 | CGAUACCUCUCAAGUCAAAUU | 872 |
| IGF2R | 6129 | UUGUGUUUCUGGACGAAUUTG | 423 | AAUUCGUCCAGAAACACAAUU | 873 |
| IGF2R | 5105 | UAGAGCUUCCAUUCCUCACGG | 424 | GUGAGGAAUGGAAGCUCUAUU | 874 |
| IGF2R | 4572 | UUCACUUGGCUCUCGCUGCAG | 425 | GCAGCGAGAGCCAAGUGAAUU | 875 |
| IGF2R | 5308 | UACCCGGCCGAUAUCUAUGGG | 426 | CAUAGAUAUCGGCCGGGUAUU | 876 |
| IGF2R | 3153 | UUCUCAAUUCCGACUGGCCTT | 427 | GGCCAGUCGGAAUUGAGAAUU | 877 |
| IGF2R | 9029 | UAUUACAGUAAAGUUGAUUGA | 428 | AAUCAACUUUACUGUAAUAUU | 878 |
| IGF2R | 1530 | UUAACACAGGCGUAUUCCGUG | 429 | CGGAAUACGCCUGUGUUAAUU | 879 |

TABLE 1-continued siRNAs against human VEGFR-1, VEGFR-2, VEGFR-3, Tie2, bFGFR, IL8RA, IL8RB, Fas, IGF2R

| Target Name | pos | siRNA guide sequence | SEQ ID NO | siRNA complement | SEQ ID NO |
|---|---|---|---|---|---|
| IGF2R | 8364 | AAAUGUGCUCUGUACGCCCAG | 430 | GGGCGUACAGAGCACAUUUTT | 880 |
| IGF2R | 5400 | UAGUUGAAAUGCUUGUCCGCT | 431 | CGGACAAGCAUUUCAACUATT | 881 |
| IGF2R | 6702 | UUGGCUCCAGAGCACGCCGGG | 432 | CGGCGUGCUCUGGAGCCAATT | 882 |
| IGF2R | 8479 | UUCUCUGACACCUCAACUCCA | 433 | GAGUUGAGGUGUCAGAGAATT | 883 |
| IGF2R | 4723 | UAAGGAGCUCAGAUCAAACAG | 434 | GUUUGAUCUGAGCUCCUUATT | 884 |
| IGF2R | 4237 | UGAACAUUCAGUCAGAUCGAA | 435 | CGAUCUGACUGAAUGUUCATT | 885 |
| IGF2R | 6203 | UAUAGUACGAGACUCCGUUGT | 436 | AACGGAGUCUCGUACUAUATT | 886 |
| IGF2R | 753 | AUGAAUAGAGAAGUGUCCGGA | 437 | CGGACACUUCUCUAUUCAUTT | 887 |
| IGF2R | 8554 | AUAAGCACAGUAAAGGUGGTA | 438 | CCACCUUUACUGUGCUUAUTT | 888 |
| IGF2R | 5462 | UUAACAGCUUAGGCGUUCCCA | 439 | GGAACGCCUAAGCUGUUAATT | 889 |
| IGF2R | 1460 | UUCCUUUCCCAUCGUUACCTG | 440 | GGUAACGAUGGGAAAGGAATT | 890 |
| IGF2R | 5206 | AUUGAUGUAGAAAUCAGGGTT | 441 | CCCUGAUUUCUACAUCAAUTT | 891 |
| IGF2R | 2559 | AUGUAGUAUUUCCUCCACGTG | 442 | CGUGGAGGAAAUACUACAUTT | 892 |
| IGF2R | 8605 | UUAAGGCUUCUUAUAGGUCGA | 443 | GACCUAUAAGAAGCCUUAATT | 893 |
| IGF2R | 4345 | AUUGAUGAGGUAGUGCUCCGG | 444 | GGAGCACUACCUCAUCAAUTT | 894 |
| IGF2R | 1187 | AAAUAUAGGAUGAACCUCCGC | 445 | GGAGGUUCAUCCUAUAUUUTT | 895 |
| IGF2R | 1184 | UAUAGGAUGAACCUCCGCUCT | 446 | AGCGGAGGUUCAUCCUAUATT | 896 |
| IGF2R | 7190 | UUGAGUAUUUGUAGGACACGT | 447 | GUGUCCUACAAAUACUCAATT | 897 |
| IGF2R | 7182 | UUGUAGGACACGUUGGAACTT | 448 | GUUCCAACGUGUCCUACAATT | 898 |
| IGF2R | 2941 | AUCCCUUAUAGAGCAAGCCTG | 449 | GGCUUGCUCUAUAAGGGAUTT | 899 |
| IGF2R | 3693 | UCAAACGUGAUCCUGGUGGAG | 450 | CCACCAGGAUCACGUUUGATT | 900 |

Chemical Modification of RNA Strand Nucleotides

The siRNA according to the invention may comprise at least one modified nucleotide in at least one of the RNA strands. A range of potential modified nucleotides are disclosed elsewhere herein. Useful modifications and combinations of modifications for use according to the invention are shown in Table 2:

TABLE 2

Chemical Modifications and Sequence Architecture

| # | Modification-Name | Format |
|---|---|---|
| 1 | PS DNA o/h | NNNNNNNNNNNNNNNNNNNNnsnsn<br>nsnsNNNNNNNNNNNNNNNNNNNN |
| 2 | Full PS | NsNsNsNsNsNsNsNsNsNsNsNsNsNsNsNsNsNsNsN<br>NsNsNsNsNsNsNsNsNsNsNsNsNsNsNsNsNsNsNsN |
| 3 | RNA o/h | NNNNNNNNNNNNNNNNNNNNNNN<br>NNNNNNNNNNNNNNNNNNNNNNN |
| 4 | Blunt-ended | NNNNNNNNNNNNNNNNNNNN<br>NNNNNNNNNNNNNNNNNNNN |
| 5 | 2'-OMe o/h | NNNNNNNNNNNNNNNNNNNNN$N^pN^p$<br>$N^pN^p$NNNNNNNNNNNNNNNNNNNNN |

TABLE 2-continued

Chemical Modifications and Sequence Architecture

| Modification-# | Name | Format |
|---|---|---|
| 6 | 2'-OMe/2'F | NNNNNNNNNNNNNNNNNNNN$N^PN^P$<br>$N^PN^P$NNNNNNNNNNNNNNNNNNNN |
| 7 | LNA (3-7 incorporations in ds region) | NNNNNNNNNNNNNNNNNNNNsnsn<br>nsnsNNNNNNNNNNNNNNNNNNNN |

N = any unmodified RNA nucleotide
n = unmodified DNA nucleotide
$N^P$ = modified RNA nucleotide
s = identifies phosphorothioate internucleoside linkage
o/h = overhang The following modifications added to the 3' position of the 3'-terminus of the siRNA strands, sometimes referred to as a '3' end cap' are also recognized as useful embodiments of the invention and may be used with any of the siRNA according to the invention:

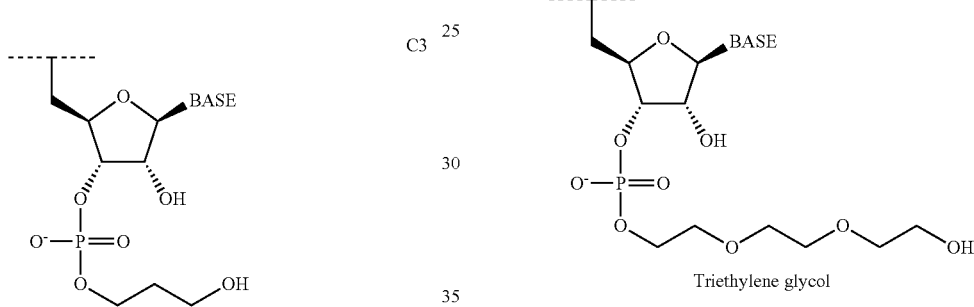

-continued

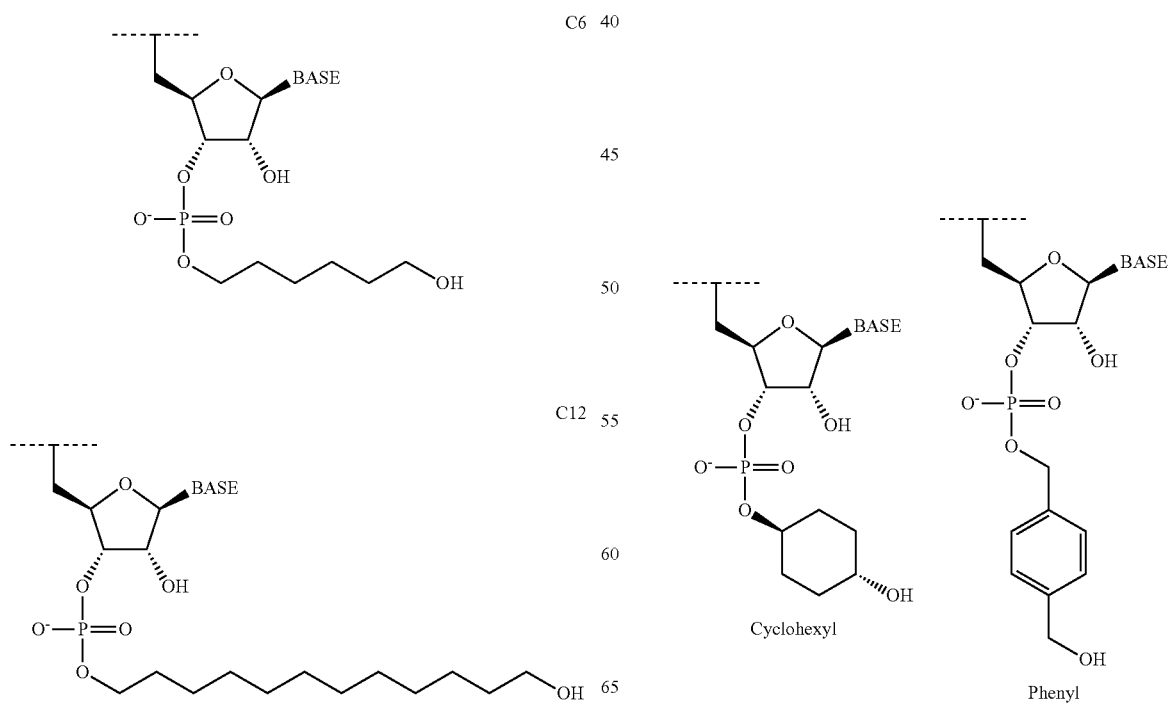

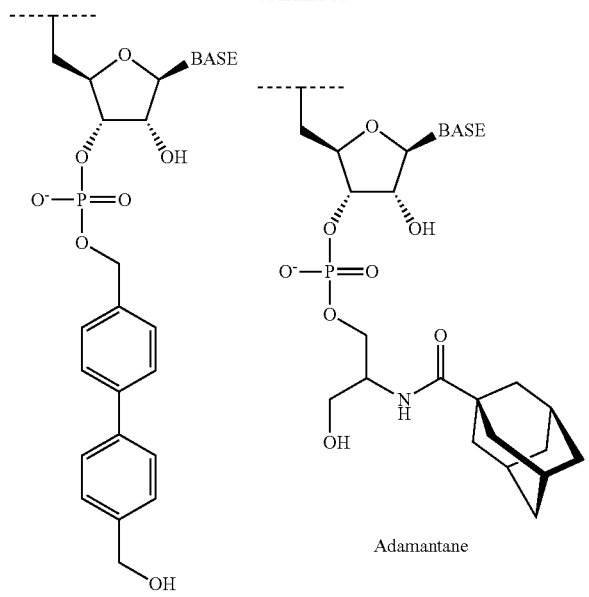

Biphenyl

Adamantane

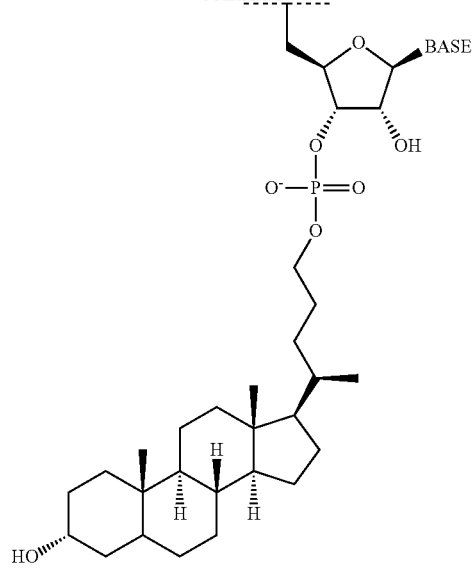

Lithocholic acid

Specific compounds with activity according to the invention include the following, shown in Table 3:

TABLE 3

Sequences and Chemistries of siRNA used in Examples

| Name | strand | Sequence (N: RNA; dN: DNA; 2'-moe RNA; s: phosphorothioate) | SEQ ID NO |
|---|---|---|---|
| pGI3-siRNA | guide strand | UCG AAG UAC UCA GCG UAA GdTdT | 901 |
|  | complement strand | CUU ACG CUG AGU ACU UCG AdTdT | 902 |
| pGL3 MOE o/h siRNA | guide strand | CUU ACG CUG AGU ACU UCG Atst | 903 |
|  | complement strand | UCG AAG UAC UCA GCG UAA Gtst | 904 |
| pGI3-C3-siRNA | guide strand | UCG AAG UAC UCA GCG UAA G-C3 | 905 |
|  | complement strand | CUU ACG CUG AGU ACU UCG A-C3 | 906 |
| pGI3-C3-MOE-siRNA | guide strand | UCG AAG UAC UCA GCG UAa g-C3 | 907 |
|  | complement strand | CUU ACG CUG AGU ACU UCg a-C3 | 908 |
| VEGFR2-siRNA1 | guide strand | UUG AGG UUU GAA AUC GAC CdCdT | 909 |
|  | complement strand | GGU CGA UUU CAA ACC UCA AdTdT | 910 |
| VEGFR2-siRNA2 | guide strand | UAA UUU GUU CCU GUC UUC CdAdG | 911 |
|  | complement strand | GGA AGA CAG GAA CAA AUU AdTdT | 912 |
| siRNA control | guide strand | ACG UGA CAC GUU CGG AGA AdTdT | 913 |
|  | complement strand | UUC UCC GAA CGU GUC ACG UdTdT | 914 |
| VEGFR2-C3-siRNA1 | guide strand | UUG AGG UUU GAA AUC GAC C-C3 | 915 |
|  | complement strand | GGU CGA UUU CAA ACC UCA A-C3 | 916 |
| VEGFR2-C3-siRNA2 | guide strand | UAA UUU GUU CCU GUC UUC C-C3 | 917 |
|  | complement strand | GGA AGA CAG GAA CAA AUU A-C3 | 918 |
| C3-siRNA control | guide strand | ACG UGA CAC GUU CGG AGA A-C3 | 919 |
|  | complement strand | UUC UCC GAA CGU GUC ACG U-C3 | 920 |
| VEGFR2-C3-MOE-siRNA1 | guide strand | UUG AGG UUU GAA AUC GAc c-C3 | 921 |
|  | complement strand | GGU CGA UUU CAA ACC UCa a-C3 | 922 |
| VEGFR2-C3-MOE-siRNA2 | guide strand | UAA UUU GUU CCU GUC UUc c-C3 | 923 |
|  | complement strand | GGA AGA CAG GAA CAA AUu A-C3 | 924 |
| Tie2-C3-MOE-siRNA1 | guide strand | UUC UUC UUU AAU UAA CAc c-C3 | 925 |
|  | complement strand | GGU GUU AAU UAA AGA AGa a-C3 | 926 |

TABLE 3-continued

Sequences and Chemistries of siRNA used in Examples

| Name | strand | Sequence (N: RNA; dN: DNA; 2'-moe RNA; s: phosphorothioate) | SEQ ID NO |
|---|---|---|---|
| Tie2-C3-MOE-siRNA2 | guide strand | UCU GAG UUU GUA AAU AUc g-C3 | 927 |
| | complement strand | CGA UAU UUA CAA ACU CAg a-C3 | 928 |
| C3-MOE-siRNA control | guide strand | ACG UGA CAC GUU CGG AGa a-C3 | 929 |
| | complement strand | UUC UCC GAA CGU GUC AGg t-C3 | 930 |

EXAMPLES

The following Examples illustrate aspects of the invention, and are not intended to limit the embodiments included in the claims recited below. The results and discussion section further below refers to experiments conducted according to the following protocols and employing the following materials. Materials and protocols that are not specifically described are considered to be routinely available to those skilled in the art.

Example 1

Preparation of siRNAs

Single strand siRNA derivatives were synthesized by standard 2'-O-TOM phosphoamidite technology and purified by Oasis® HLB Extraction Plates (Waters). Sense- and antisense stranded siRNA were mixed in hybridization buffer (100 mM potassium acetate, 2 mM magnesium acetate, 30 mM Hepes, pH 7.6) heat-denatured at 90° C. for 3 min and annealed at 37° C. for 60 min. 100 μM stock solutions of siRNA duplexes were stored at −20° C.

Example 2

Incubation in Serum and Analysis by IE-HPLC (LC-MS)

In a standard serum assay, 6 μL 20 μM of each siRNA were mixed with 54 μL serum or CSF and heated at 37° C. in an incubator. 50 μL of the cooled mixture was loaded on an analytical DNA-pac PA-100 Column (Dionex) and analyzed with a NaCl gradient (0-0.6 M in 30 min) in a 1:10 Acetonitrile:Buffer (20 mM sodium acetate, 1 mM magnesium acetate, pH 6.5) solution.

For LC-MS analysis 100 μL (20 μM or 50 μM) each siRNA was mixed with 900 μL sterile fetal bovine serum (GIBCO) incubated at 37° C. and separated by HPLC as indicated previously (except of the NaCl gradient: 0M-0.36M in 9'/0.36M-0.6M in 12'). Degradation products were desalted on NAP columns and analyzed by LC-ESI⁻-MS.

Example 3

Incubation in Gastric Acid

To prepare a standard gastric acid assay, FVB and C57BL6 mice, weighing 18 to 20 g (6 to 8 weeks old), were obtained from Charles River Laboratories (Les Oncins, France). Animals were sacrificed using $CO_2$, and then stomachs were quickly recovered. Gastric fluid as well as stomach contents were collected and pooled, then loaded on centrifugal filter devices (Ultrafree MC, Millipores). Filter units were spun for 10 minutes according to manufacturer's recommendations. The filtrate, corresponding to mouse gastric fluid, was recovered, aliquoted and frozen prior further experiments.

For each assay, 20 μM of siRNA solutions were diluted in 9× volume of gastric acid as above described and incubated at 37° C. for 0, 5, 10, 15, 30, 60 and 120 min.

Example 4

Incubation in Intestinal Lavage

To prepare a standard intestinal lavage assay, Male Wistar rat were fasted, anesthetized with isoflurane. Intestinal lavage was obtained by in situ perfusion of the small intestine (duodenum, jejunum, ileum) with 10 mL saline (0.5 mL/min) followed by 20 mL water (1 mL/min). Outlet collected was centrifuged (3000×g, 15 min, 22° C.), and supernatant passed through a 1.2-μm filter and stored at −20° C.

For each assay, 20 μM siRNA solutions were diluted in 9× volume of intestinal lavage and incubated at 37° C. for 0, 15, 30, 60, 180 and 360 min.

Example 5

Incubation in Mouse Liver Microsomes

In a standard liver microsome assay, to 10 μl of a 250 μM solution of siRNA were added 25 μl of mouse liver microsomes (GEntest 452701 Charge 11) at 20 mg protein/ml, 365 μl of 100 mM phosphate buffer (pH 7.4), 50 μl of UDPGA cofactor (24 mM in water), 50 μl of NADPH. Incubation was quenched by freezing at t=0 min and t=60 min.

Example 6

Incubation in Rat S12 Supernatant

For a standard rat S12 supernatant assay, 10 μl of a 250 μM solution of siRNA were added to 17 μl of rat liver S12 at 29.9 mg protein/ml, 373 μl of 100 mM phosphate buffer (pH 7.4), 50 μl of UDPGA cofactor (24 mM in water), 50 μl of NADPH. Incubation was quenched by freezing at t=0 min and t=60 min.

Example 7

Incubation in Mouse Serum

For a standard incubation in mouse serum, 20 M siRNA solutions were diluted in 9× volume of murine serum (Harlan nude mouse) and incubated at 37° C. for 0, 15, 30, 60, 180 and 360 min.

Example 8

Gel Electrophoresis Stability Assay

A 10 μL aliquot of incubation solution was taken immediately after shaking and shock-frozen on dry ice, the mixtures were incubated at 37° C. and aliquots were shock frozen at various time points. Aliquots were thawed in 30 μL (15 μL respectively) Loading Buffer (Elchrom Sc., Cham, Switzerland) and separated on a SF50 gels (Elchrom Sc., Cham, Switzerland) at 120 V, 8° C. for 240 min. Bands were stained with SYBR Gold (Molecular Probes) and picture were taken with a BIORAD ChemiDoc™ XRS system.

Example 9

Cell Culture

The mouse immortalized endothelial cell line MS1 (ATCC CRL-2279) was grown in DMEM high glucose (4.5 g/l) supplemented with L-Glutamine and 10% heat-inactivated FCS (AMIMED, Switzerland) on 1.5% Gelatine-coated culture dishes. MS1 cells were transfected in 24 well-format with siRNA using HiPerfect (QIAGEN) according to manufacturer procedure (tetraplicate, final siRNA concentration was 10 nM or as indicated).

Example 10

FACS Analysis

Non-transfected and siRNA transfected MS1 cells were analyzed by FACS for VEGFR2 levels. Briefly, cells were trypsinized from duplicate or triplicate wells, pooled for each conditions, then washed twice with PBS+10% FCS and incubated 10 minutes on ice prior addition of RPE-conjugated anti-VEGFR2 Ab (1 μg/$10^6$ cells; Avas 12α1, BD Pharmingen). RPE-labeled isotype IgG2α were used as FACS control (BD Pharmingen). FACS acquisition and analysis were performed on a FACScalibur using Cell Quest Software (Becton-Dickinson).

Example 11

Animal Studies

Female FVB mice (6 to 8 weeks old), were obtained from Charles River Laboratories (Les Oncins, France). Mice were identified via ear markings and kept in groups (6 animals per cage) under normal conditions and observed daily. Six mice were used per treatment group and all animal experiments were performed in strict adherence to the Swiss law for animal protection.

The reference chamber model has been described in publications (e.g. Wood J, Bold G, Buchdunger E, et al. PTK787/ZK 222584, a novel and potent inhibitor of vascular endothelial growth factor receptor tyrosine kinases, impairs vascular endothelial growth factor-induced responses and tumor growth after oral administration. Cancer Res 2000; 60:2178-89) In brief, porous tissue chambers made of perfluoro-alkoxy-Teflon (Teflon®-PFA, 21 mm×8 mm diameter, 550 μl volume) were filled with 0.8% agar (BBL® Nr. 11849, Becton Dickinson, Meylan, France) and 20 U/ml heparin, (Novo Nordisk A/S, Bagsvaerd, Denmark) supplemented with or without 3 μg/ml recombinant human VEGF and siRNAs as indicated. Solutions were maintained at 42° C. prior the filling procedure. Mice were anesthetized using 3% Isoflurane (Forene®, Abbott AG, Cham, Switzerland) inhalation. For subcutaneous implantation, a small skin incision was made at the base of the tail to allow the insertion of an implant trocar. The chamber was implanted under aseptic conditions through the small incision onto the back of the animal. The skin incision was closed by wound clips (Autoclip 9 mm Clay Adams). Depending on the required dose, siRNAs were diluted in "injectable quality grade" 0.9% saline solution then delivered to animals either i.p. (200 μL/dose) or p.o. by gavage (100 μL/dose). The mice were receiving the first dose 2 to 4 hours before implanting chambers; then treated daily for 2 days. If not otherwise indicated, mice were sacrificed three days after implantation, chambers excised and the vascularized fibrous tissue formed around each implant carefully removed. Body weight was used to monitor the general condition of the mice. Statistical analysis was done using one-way ANOVA followed by Dunnett test.

Example 12

B16 Melanoma Xenograft Model

The syngeneic B16/BL6 murine melanoma model, previously identified to be responsive to antiangiogenic therapy (e.g. LaMontagne K, Littlewood-Evans A, Schnell C, O'Reilly T, Wyder L, Sanchez T, Probst B, Butler J, Wood A, Liau G, Billy E, Theuer A, Hla T, Wood J. Antagonism of sphingosine-1-phosphate receptors by FTY720 inhibits angiogenesis and tumor vascularization. Cancer Res. 2006 Jan. 1; 66(1):221-31), was used to evaluate the antitumor activity of standard or modified siRNAs. Tumor cells (1 μL, 5×$10^4$/μL) were injected intradermally into the dorsal pinna of both ears of syngeneic female C57BL/6 mice. Measurements of primary tumor area ($mm^2$) were carried out on days 7, 14, and 21 after tumor cell inoculation using computer-assisted image analysis software (KS-400 3.0 imaging system, Zeiss) and a specifically designed macro. From days 7 to 21, mice were receiving siRNAs diluted in "injectable quality grade" 0.9% saline solution either i.p. (200 μL/dose) or p.o. by gavage (100 μL/dose) once a day. Mice were sacrificed on day 21, and cranial lymph node metastases were weighed and then frozen.

In these results, actual siRNA sequences and chemistries employed may be determined by reference to Table 3.

Wild-Type siRNAs are Degraded in Mouse Serum from Both 3'-Ends

Oligonucleotide degradation by nucleases is predominantly 3'-exonucleolytic. Modification of antisense oligonucleotides at their termini by the introduction of aromatic or lipophilic residues delays their nucleolytic degradation[17]. To verify whether this metabolic pathway would also be dominant for siRNA, we incubated at 37° C. a unmodified siRNA (wild-type siRNA) in mouse serum for up to 3 hours.

The unmodified siRNA sequence employed was pGl3-siRNA (see Table 3)

The mixtures were analyzed with Strong Anion Exchange HPLC at t=0 min., t=30 min, t=180 min.

Figure 1B:
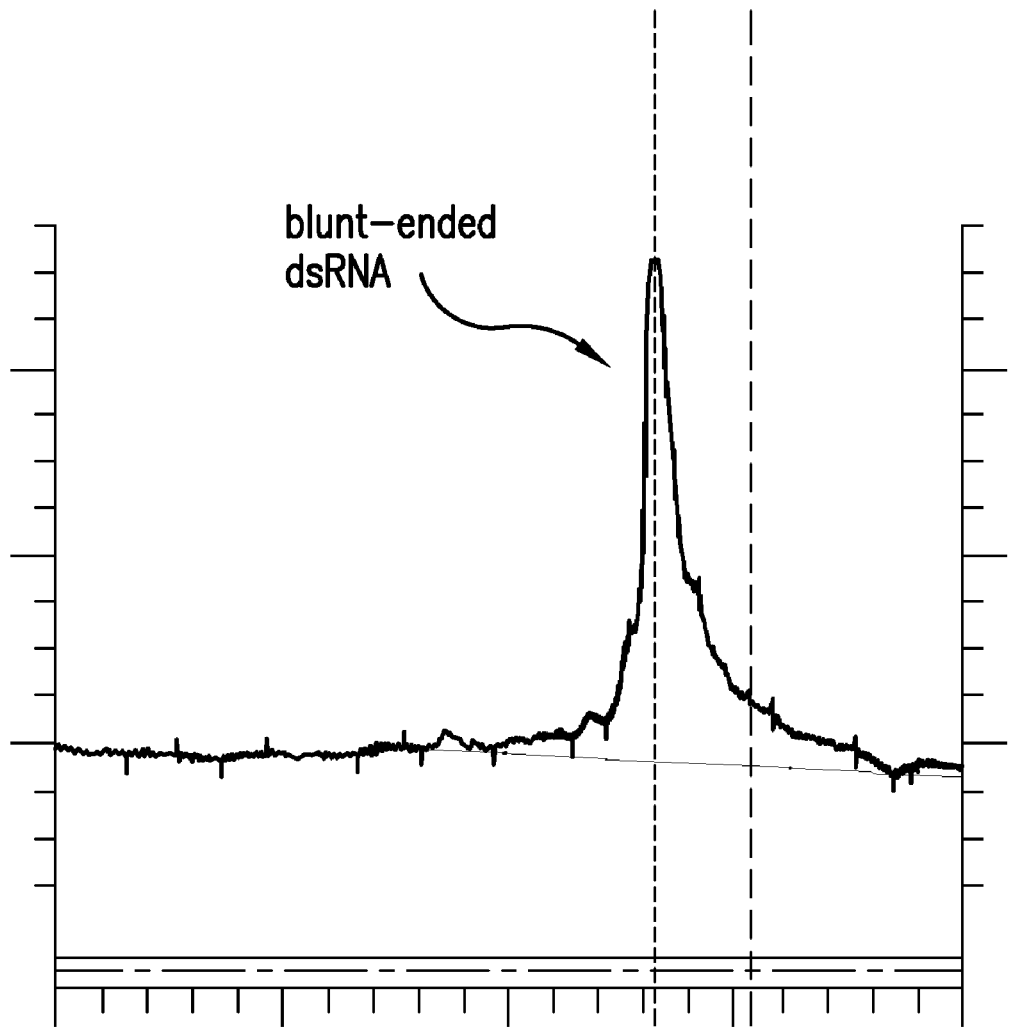
Figure 1C:
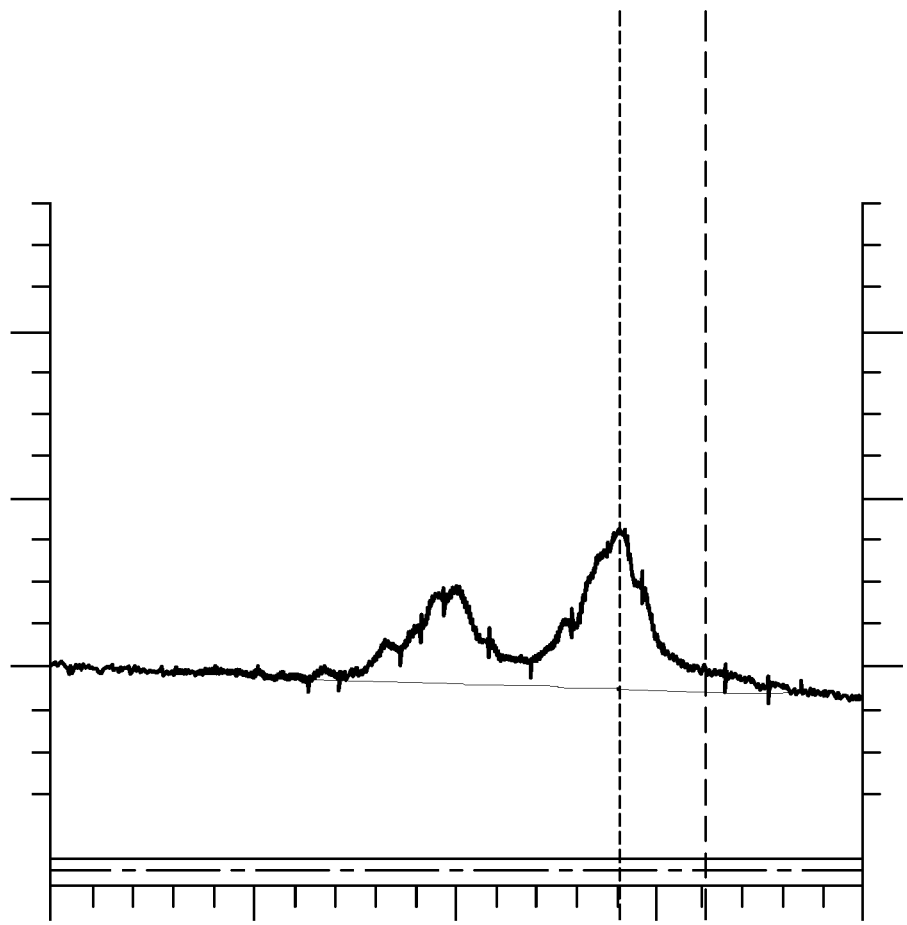
Figure 1E:
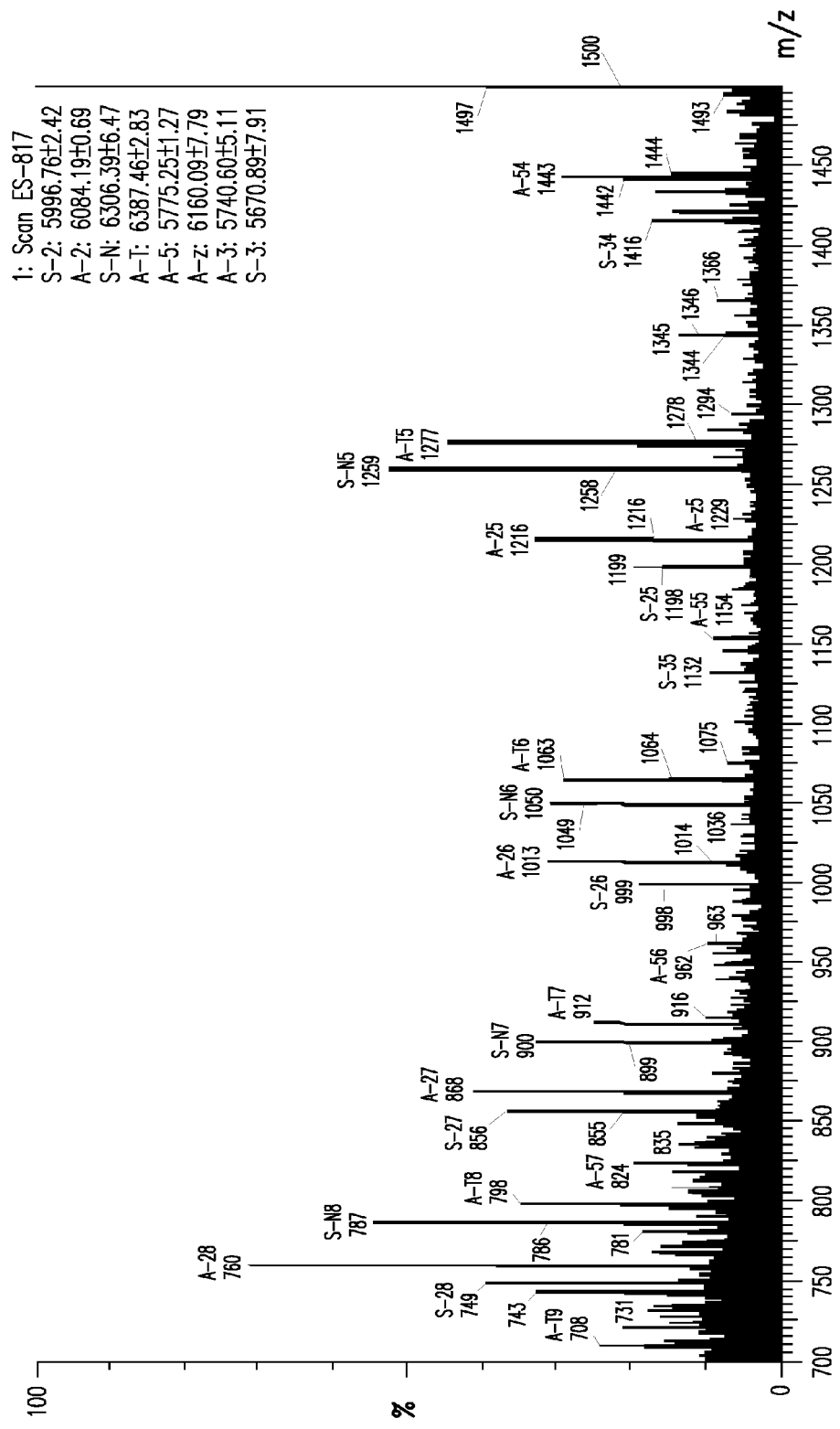

As shown in FIGS. 1a, 1b and 1c, at t=30 min, a well defined peak corresponding to blunt ended siRNA was observed. By t=3 h substantial degradation is observed. FIGS. 1d and 1e illustrate the metabolites identified by HPLC-ESI-MS analysis. This analysis revealed the presence of several metabolites corresponding to the loss of the 3' overhangs and of the 3'-terminal first base pairing ribonucleotide on both strands. Digestion of the 5'-terminal ribonucleotide of the guide strand was also observed.

FIG. 1 suggests the degradation pathway of unmodified siRNAs in serum. DNA overhangs are first digested, possibly by 3'-exonucleases. In the LC-MS, additional metabolites were also detected which correspond to the loss of the first base-pairing 3'-ribonucleotide of both strands and also the first 5'-base-pairing ribonucleotide of the guide strand.

Figure 2:
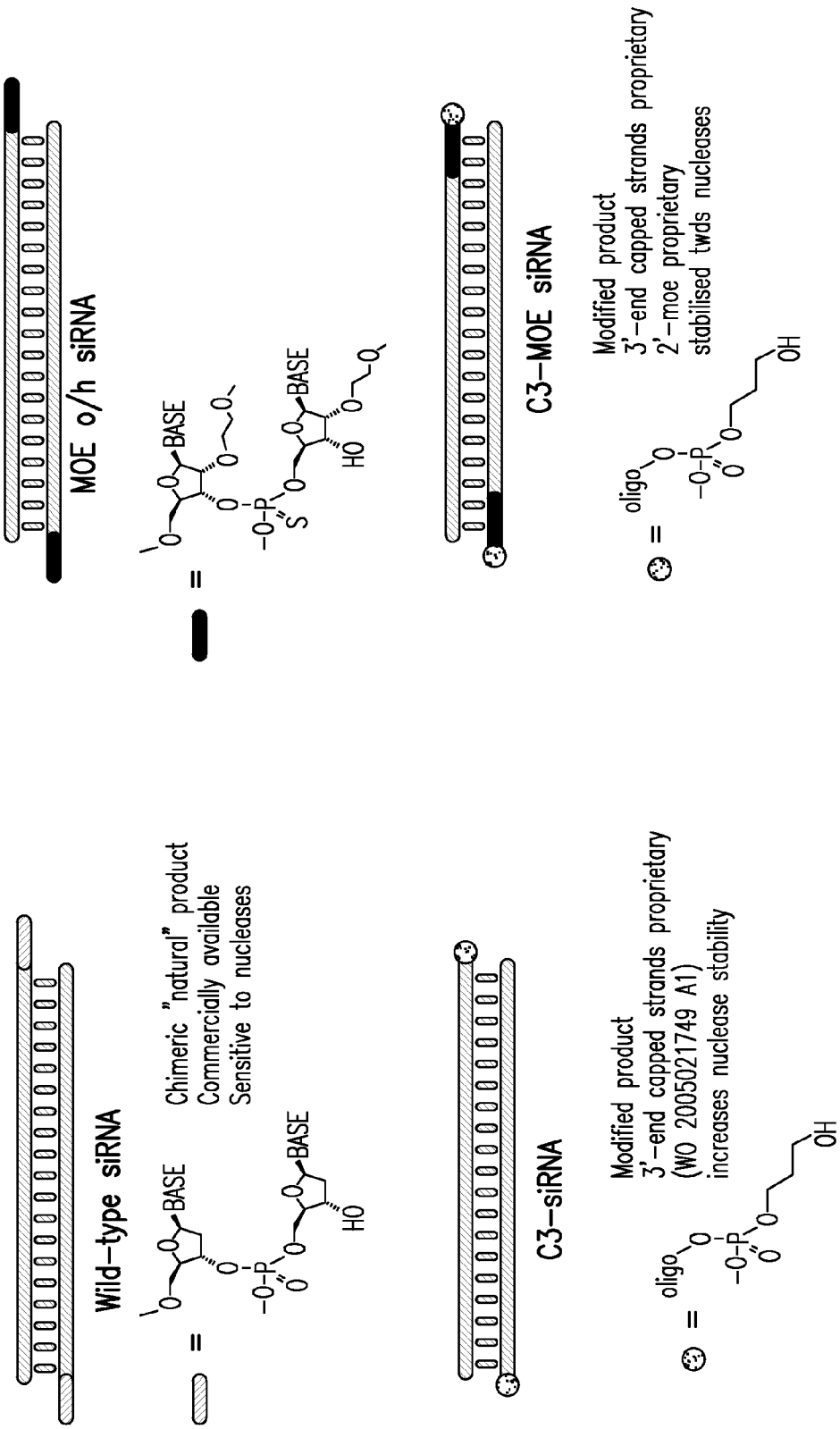
FIG. 2: illustration of four double-stranded RNA formats: wild-type (or unmodified) siRNA. MOE o/h siRNA, C3-siRNA and C3-MOE siRNA.

3'-Modified siRNAs are Stable Through the GI Tract siRNAs with 2'-methoxyethyl ribonucleotides overhangs (MOE o/h siRNA), blunt-ended siRNAs 3'-capped with a hydroxypropoxy phosphodiester moiety (C3-siRNA), and hydroxypropoxy phosphodiester 3'-capped siRNAs where the two first base paring nucleotide at 3'-end of each strand were modified by 2'-methoxyethyl ribonucleotides residues (C3-MOE siRNA) were synthesized. These compounds are illustrated schematically in FIG. 2.

Figure 3:
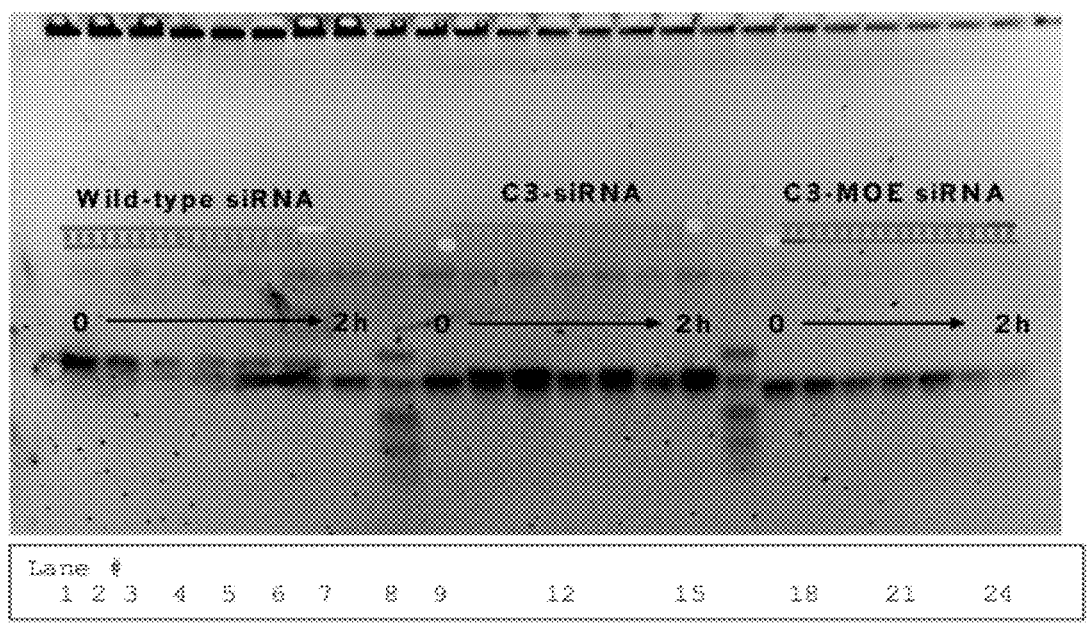
FIG. 3: Stability of siRNA in 3 different formats in mouse gastric acid. Samples were incubated at 37° C. in mouse gastric acid at a 2 micromolar concentration. Disappearance of parent compound was followed over a 2-6 hours period by quantifying the parent compound band.
Lane 1-7: wild-type siRNA in gastric acid at t=0, 5, 10, 15, 30, 60 and 120 min
Lane 8: ds RNA ladder (30, 21, 19, 16, 13, 10 bp)
Lane 9-15: C3 siRNA in gastric acid at t=0, 5, 10, 15, 30, 60 and 120 min
Lane 16: ds RNA ladder (30, 21, 19, 16, 13, 10 bp)
Lane 17-24: C3-MOE siRNA in gastric acid at t=0, 5, 10, 15, 30, 60 and 120 min

First siRNAs were incubated in mouse gastric acid for 2 h (FIG. 3). No degradation was observed in the cases of C3 siRNA and C3-MOE sRNA, while degradation of wild-type siRNA was observed after 30 minutes.

Figure 4:
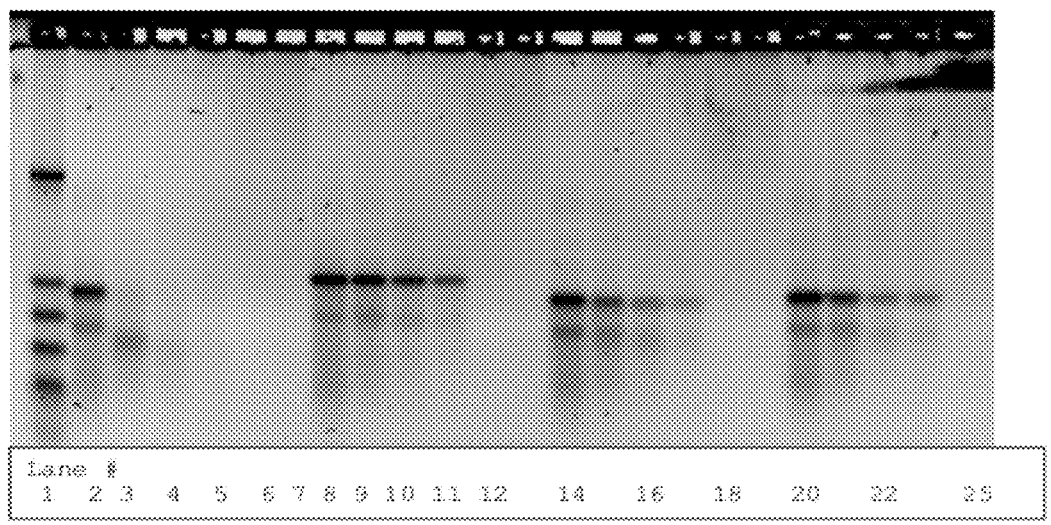
FIG. 4: Stability of siRNA in 4 different formats in intestinal lavage. Samples were incubated at 37° C. in liver microsomes at a 5 micromolar concentration.
(From Left to Right)
Lane 1: ds RNA ladder (30, 21, 19, 16, 13, 10 bp)
Lane 2-7: wild-type siRNA in intestinal lavage at t=0, 15, 30, 60, 180 and 360 min
Lane 8-13: moe o/h siRNA in intestinal lavage at t=0, 15, 30, 60, 180 and 360 min
Lane 14-19: C3 siRNA in intestinal lavage at t=0, 15, 30, 60, 180 and 360 min
Lane 20-25: C3-MOE siRNA in intestinal lavage at t=0, 15, 30, 60, 180 and 360 min

Stability in intestinal fluid obtained from intestinal lavage of rats revealed almost complete degradation of wild-type siRNA after 15 minutes whereas parent compound in the MOE o/h siRNA, C3-siRNA and C3-Moe siRNA were observed for 60 minutes. (FIG. 4)

Figure 5:
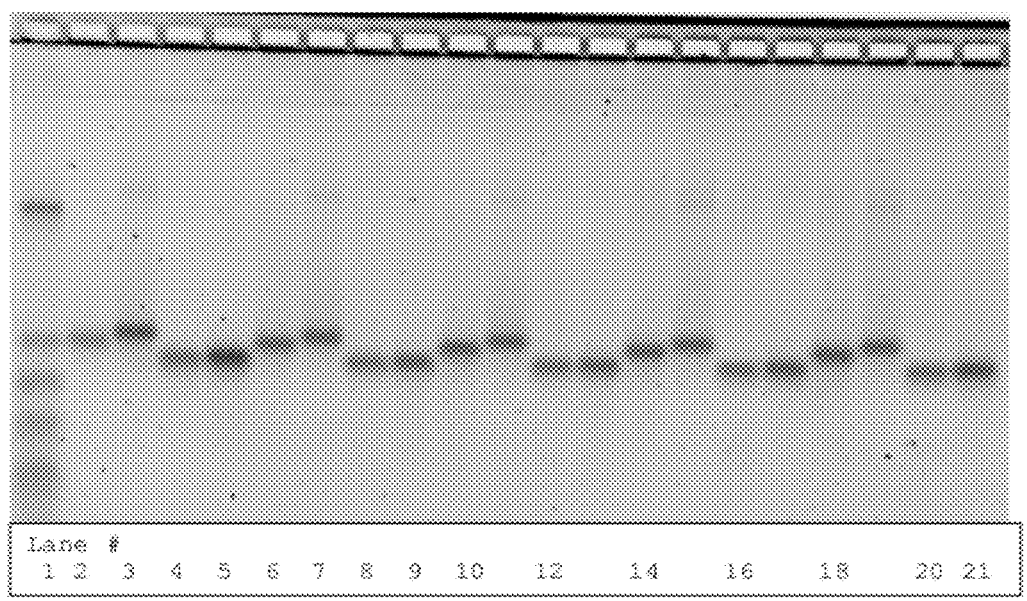
FIG. 5: Stability of siRNA in 4 different formats in liver microsomes. Samples were incubated at 37° C. in intestinal fluid from rat intestinal lavage at a 2 micromolar concentration.
(From Left to Right)
Lane 1: ds

Stability in liver was evaluated using a liver microsome assay and a S12 assay (representative of liver cytosolic enzymatic activity). Results are shown in FIG. 5. In both cases, no degradation was observed after 60 minutes of incubation.

Figure 6:
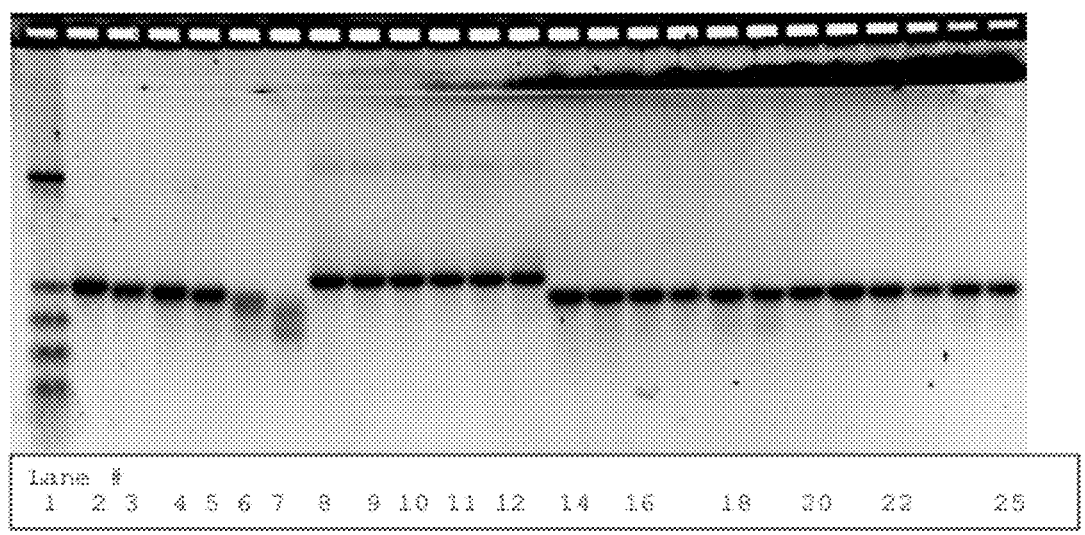
FIG. 6: Stability of siRNA in 4 different formats in mouse serum. Samples were incubated at 37° C. in mouse serum at a 2 micromolar concentration. Disappearance of parent compound was followed over a 6 hours period by quantifying the parent compound band.
(From Left to Right)
Lane 1: ds RNA ladder (30, 21, 19, 16, 13, 10 bp) RNA ladder (30, 21, 19, 16, 13, 10 bp)
Lane 2: wild-type siRNA untreated
Lane 3: moe o/h siRNA untreated
Lane 4: C3 siRNA untreated
Lane 5: C3-MOE siRNA untreated
Lane 6-9: same as 2-5 in liver microsomes t=0
Lane 10-13: same as 2-5 in liver microsomes t=60'
Lane 14-17: same as 2-5 in supernatant S12 t=0
Lane 18-21: same as 2-5 in supernatant S12 t=60'
Lane 2-7: wild-type siRNA in mouse serum at t=0, 15, 30, 60, 180 and 360 min
Lane 8-13: moe o/h siRNA in mouse serum at t=0, 15, 30, 60, 180 and 360 min
Lane 14-19: C3 siRNA in mouse serum at t=0, 15, 30, 60, 180 and 360 min
Lane 20-25: C3-MOE siRNA mouse serum at t=0, 15, 30, 60, 180 and 360 min

Finally, siRNAs were tested in mouse serum by incubation at 2 micromolar for up to 6 hours at 37° C. (results in FIG. 6). Parent compound stability was followed by gel electrophoresis. In the cases of modified siRNAs (C3 siRNA, C3-MOE siRNA of MOE o/h siRNA), no significant degradation was observed while the wild-type siRNA This study indicate that wild type (unmodified) siRNAs are metabolized in mouse gastric acid and in mouse serum. In case of 3'-ends modified siRNAs, no degradation was observed in the GI tract. Therefore it is likely that 3'-modified siRNAs will have a higher oral bioavailability than wild-type siRNAs Systemically Delivered 3'-Modified siRNAs are More Active in an In Vivo Growth Factor Induced Angiogenesis Mode[18].

Firstly, the ability of modified siRNAs (C3-siRNA and CE-MOE siRNA) to down regulate a target gene was checked in cellulo by measuring VEGFR2 surface level of MS1 cells transfected with anti-VEGFR2 siRNAs.

Pools of 2 anti VEGFR2 siRNAs as wild-type siRNAs, C3-siRNAs and C3-MOE siRNAs were administered intraperitoneally. Results are shown in FIG. 7. Pooled Wild type siRNAs reduced significantly the VEGF induced vascularization at the higher dose of 25 micrograms per mice per day. The same level of inhibition was observed at a 5-fold lower dose with C3-siRNA. In the case of the C3-MOE siRNAs pool, significant reduction of vascularized tissue weight was observed at all tested doses including the lowest 0.2 microgram per mouse per day.

Figure 8A:
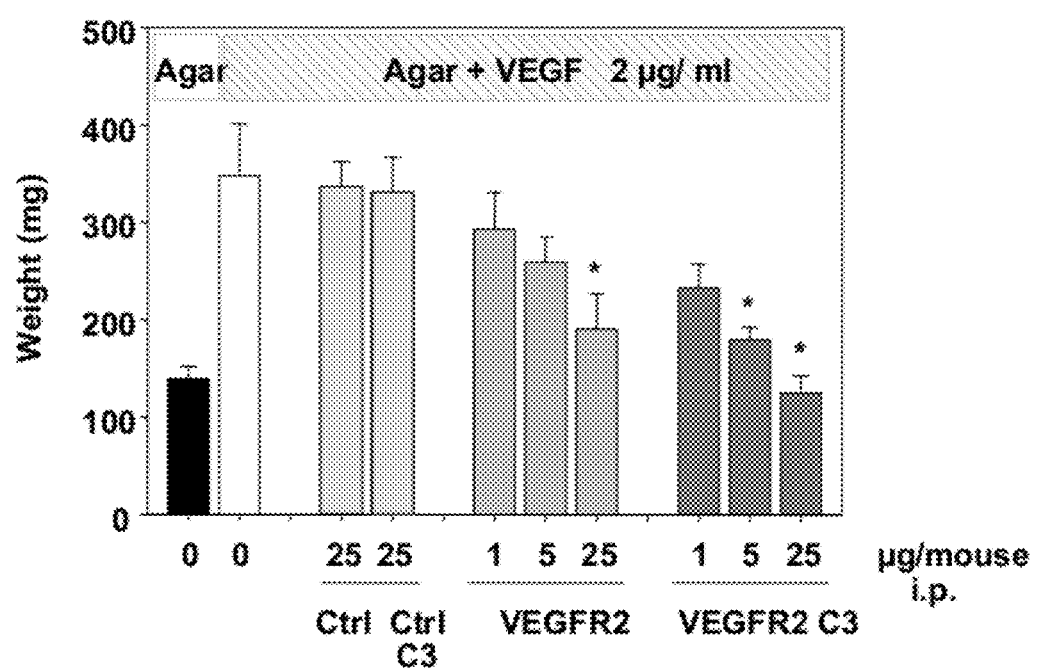
FIGS. 8a and 8b: In vivo testing of wild-type siRNA, C3-siRNA and C3-Moe siRNA in a growth factor induced angiogenesis "Agar Chamber" mouse model.
Figure 8B:
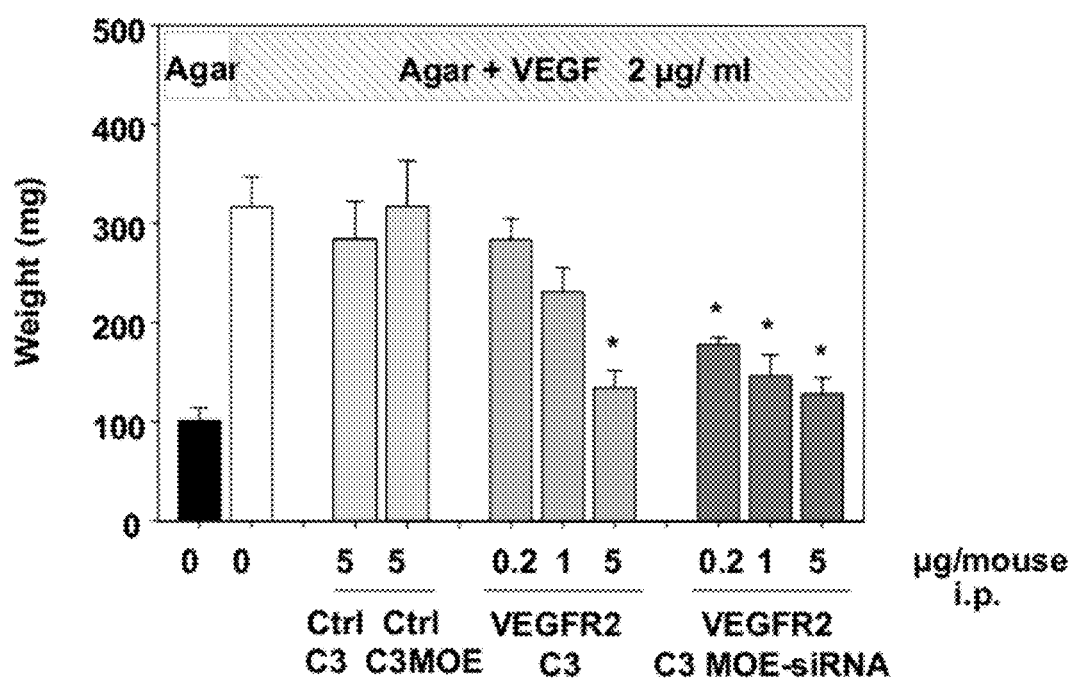

FIGS. 8a and 8b show that, when given intraperitoneally, both VEGFR2-C3 and C3-MOE siRNAs were active at below 1 microgram per mouse per day dose.

Figure 9A:
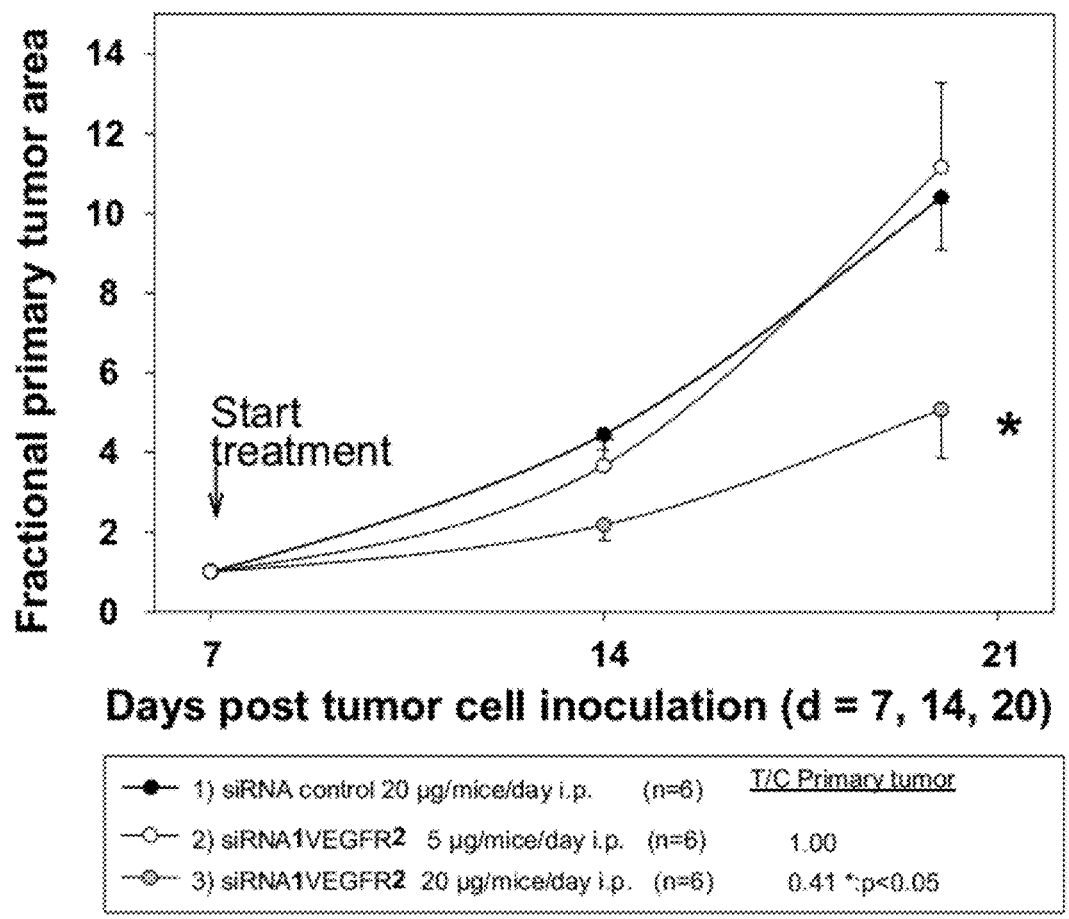
FIG. 9a shows that i.p. treatment with modified VEGFR2 siRNA significantly reduces tumour development.
Figure 9B:
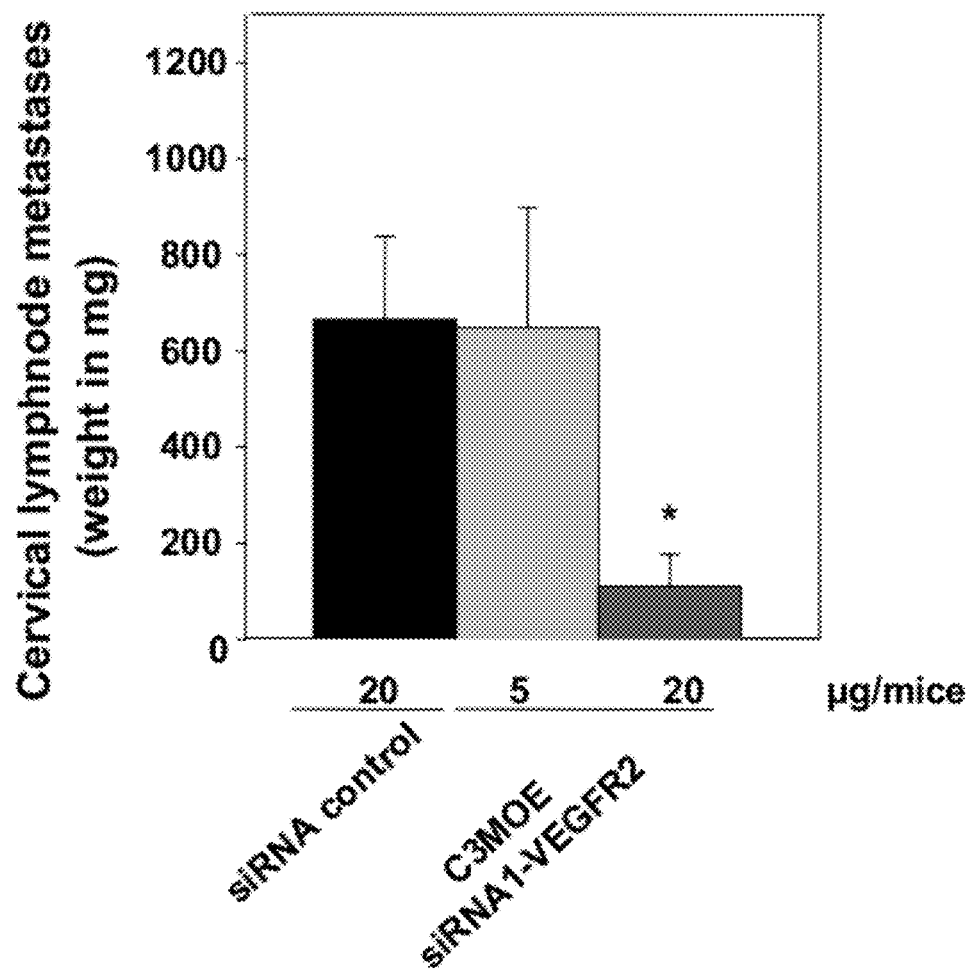
FIG. 9b also shows that i.p. injection of VEGFR2 siRNA at 20 ug per mouse results in significant inhibition of tumour growth.

In vivo testing of anti-VEGFR2C3-MOE siRNA given intraperitoneally (i.p.) in a B16 homograft melanoma tumor mouse model. FIG. 9a shows that i.p. treatment with modified VEGFR2-C3-MOE-siRNA significantly reduces tumour development. FIG. 9b also shows that i.p. injection of VEGFR2-C3-MOE-siRNA at 20 ug per mouse results in significant inhibition of tumour growth.

Oral Delivery of siRNA for Treatment of Angiogenic Disorders

Figure 10:
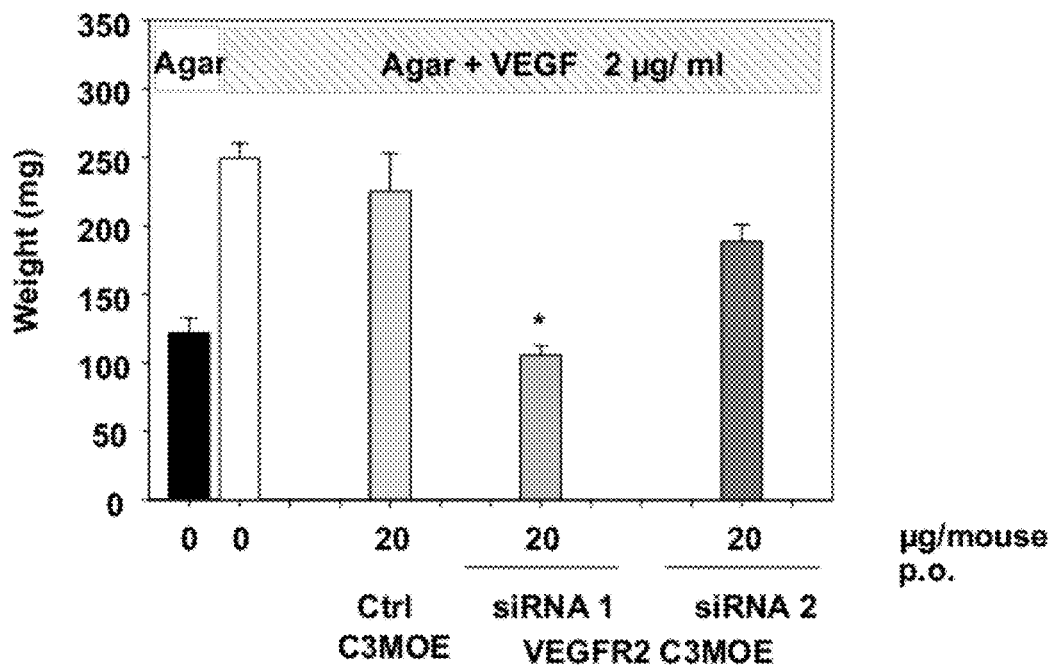
FIG. 10: In vivo testing of C3-MOE siRNA in a growth factor induced angiogenesis mouse model. anti-VEGFR2 siRNAs were given daily orally for three days at 20 micrograms per mouse per day.

FIG. 10 shows that given orally, at a dose of 20 micrograms per mouse per day, the VEGFR2-C3-MOE-siRNA1 reduced vascularization weight down to basal level (e.g. weight without growth factor induction). Actual siRNA sequences used are referred to in Table 3.

Figure 11A:
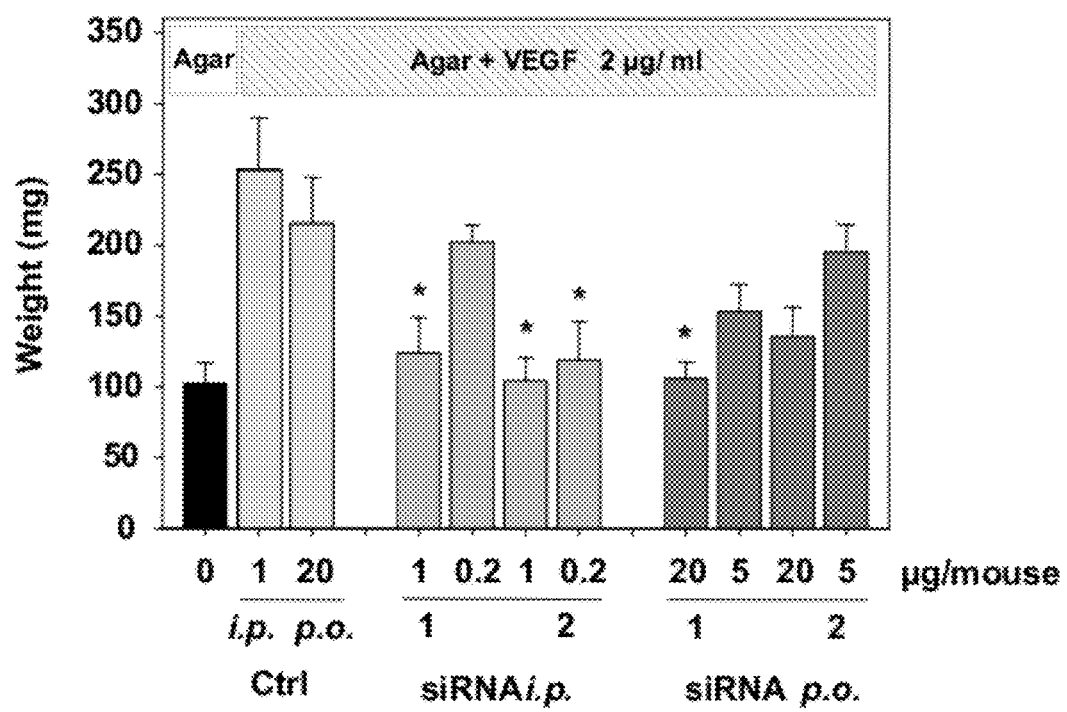
FIG. 11a: weight of excised tissue.
Figure 11B:
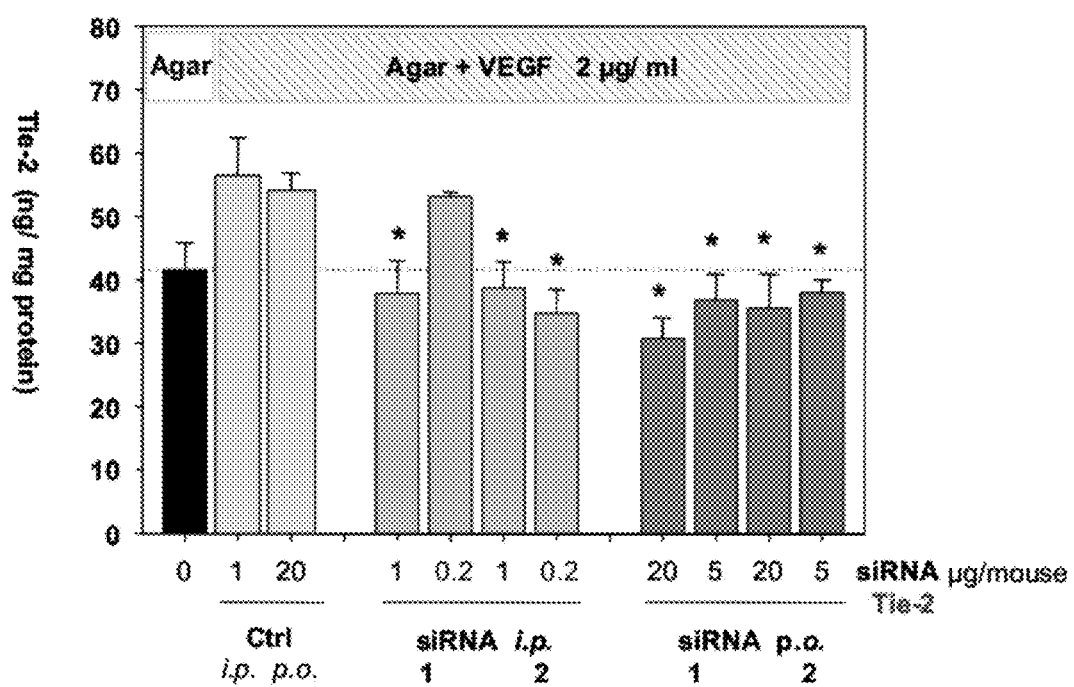
FIG. 11b: Tie2 protein knock-down

Anti Tie2 C3-MOE siRNAs were also tested in the growth factor induced angiogenesis model under both intraperitoneal and oral deliveries. FIG. 11a and 11b show that given orally, both C3-MOE siRNAs directed at Tie2 were active at 20 microgram per mouse per day. Actual siRNA sequences used may be determined by reference to Table 3.

The data shows that 3'-end modified siRNAs with or without additional internal modifications are able to demonstrate therapeutic effect at reasonable doses upon oral administration.

REFERENCES 1. a) Y. Tomari et al. *Genes and Development* 19 (2005), 517; b) P. Shankar et al. *JAMA* 11 (2005), 1367; c) Y. Dorsett et al. *Nature Reviews* 3 (2004), 318
2. a) P. D. Zamore et al. *Cell* 101, (2000), 25; b) S. M. Hammond et al. *Nature* 404 (2000), 293
3. a) G. Meister et al. *Molecular Cell* 15 (2004), 185.
4. S. M. Elbashir et al. *Genes Dev.* 15 (2001), 188.
5. S. J. Reich et al. *Molecular Vision* 9 (2003), 210.
6. a) Dorn et al. *Nucleic Acids Research* 32 (2004), e49; b) D. R. Thakker et al. *PNAS* 101 (2004), 17270; c) D. R. Thakker et al. *Molecular Psychiatry* 10 (2005), 714
7. V. Bitko et al. *Nature Medicine* 11 (2005), 50.
8. E. Song et al. *Nature Medicine* 9 (2003), 347.
9. D. A. Braasch et al. *Biochemistry* 42 (2003), 7967.
10. Harborth, Antisense Nucleic Acid Drug Devt, 2003
11. A. H. S. Hall et al. *Nucleic Acids Research* 32 (2004), 5991.
12. M. Amarzguioui et al. *Nucleic Acids Research* 31 (2003), 589.
13. F. Czauderna et al. *Nucleic Acids Research* 31 (2003), 2705.
14. T. Prakash et al. *Journal of Medicinal Chemistry* 48 (2005), 4247.
15. J. Elmen et al. *Nucleic Acids Research* 33 (2005), 439.
16. A. S. Boutorin, L. V. Guskova, E. M. Ivanova, N. D. Kobetz, V. F. Zafytova, A. S. Ryte, L. V. Yurchenko and V. V. Vlassov *FEBS Lett.* 254 (1989), p. 129
17. J. Wood et al. *Cancer Research* 60 (2000), 2178.
18. K. LaMontagne et al. *Cancer Res.* 66 (2006), 221.

We claim:

1. A short interfering ribonucleic acid (siRNA), said siRNA comprising two RNA strands that are complementary to each other over at least 15 nucleotides, wherein each strand is 49 nucleotides or less, and wherein the 3'-terminus of at least one strand comprises a modification at the 3' carbon, wherein the modification is:

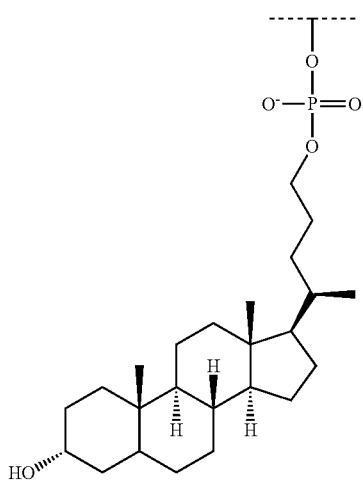

2. The siRNA according to claim 1, wherein the first two base-pairing nucleotides at the 3' end of each strand are modified.

3. The siRNA according to claim 1, wherein the first two base-pairing nucleotides at the 3' end of each strand are 2'-methoxyethyl ribonucleotides residues.

4. The siRNA according to claim 1, wherein each strand is 18 nucleotides.

5. The siRNA according to claim 1, wherein each strand is 19 nucleotides.

6. The siRNA according to claim 1, wherein both ends of the siRNA are blunt-ended.

7. The siRNA according to claim 1, having stability in a standard gastric acid assay that is greater than an unmodified siRNA with the same nucleotide sequence.

8. The siRNA according to claim 1, having stability in a standard serum assay is greater than an unmodified siRNA with the same nucleotide sequence.

9. The siRNA according to claim 1, having stability in a standard intestinal lavage assay that is greater than an unmodified siRNA with the same nucleotide sequence.

10. The siRNA according to claim 1, having an enhanced bioavailability compared to an unmodified siRNA of the same nucleotide sequence.

11. Pharmaceutical composition comprising the siRNA according to claim 1, and a pharmaceutically acceptable carrier.

12. The siRNA according to claim 1, wherein the first two base-pairing nucleotides at the 3' end of each strand are modified, wherein each modified nucleotide has an internucleoside linkage which is an amide linkage.

13. The siRNA according to claim 1, wherein the first two base-pairing nucleotides at the 3' end of each strand are modified, wherein each modified nucleotide is selected from among nucleotides having a modified internucleoside linkage selected from among phosphorothioate, phosphorodithioate, phosphoramidate, boranophosphonoate, and amide linkages.

14. The siRNA according to claim 1, comprising a 1 to 6 nucleotide overhang on at least one of the 5' end or 3' end.

15. The siRNA according to claim 1, for use as a medicament which is administered orally, topically, parenterally, by inhalation or spray, or rectally, or by percutaneous, subcutaneous, intravascular, intravenous, intramuscular, intraperitoneal, intrathecal or infusion technique.

16. A short interfering ribonucleic acid (siRNA), said siRNA comprising two RNA strands that are complementary to each other over at least 15 nucleotides, wherein each strand is 49 nucleotides or less, and wherein the 3'-terminus of each strand comprises a modification at the 3' carbon, wherein the modification is:

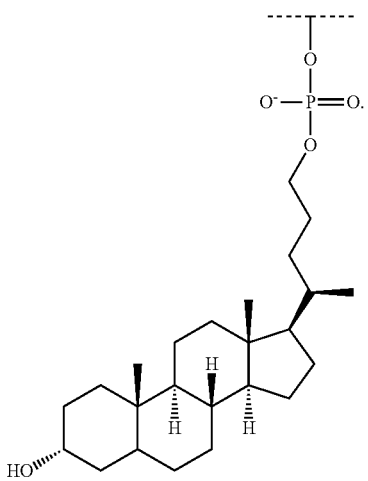

17. The siRNA according to claim 16, wherein each strand is 19 nucleotides.

18. The siRNA according to claim 16, wherein one end of the siRNA is blunt-ended.

19. The siRNA according to claim 16, wherein the two strands are fully complementary to each other over 19 nucleotides and wherein the siRNA is blunt-ended.

20. The siRNA according to claim 16, wherein at least one additional nucleotide is modified.

* * * * *